US012601742B2

(12) United States Patent
Podratz et al.

(10) Patent No.: US 12,601,742 B2
(45) Date of Patent: Apr. 14, 2026

(54) METHODS AND MATERIALS FOR TREATING ENDOMETRIAL CANCER BY ASSESSING COMBINATIONS OF MUTATIONS AND EXPRESSION LEVELS

(71) Applicants: Mayo Foundation for Medical Education and Research, Rochester, MN (US); UNIVERSITY OF IOWA RESEARCH FOUNDATION, Iowa City, IA (US)

(72) Inventors: Karl C. Podratz, Rochester, MN (US); Jesus Gonzalez Bosquet, Iowa City, IA (US)

(73) Assignees: Mayo Foundation for Medical Education and Research, Rochester, MN (US); University of Iowa Research Foundation, Iowa City, IA (US)

( * ) Notice: Subject to any disclaimer, the term of this patent is extended or adjusted under 35 U.S.C. 154(b) by 794 days.

(21) Appl. No.: 17/922,720

(22) PCT Filed: May 3, 2021

(86) PCT No.: PCT/US2021/030467
§ 371 (c)(1),
(2) Date: Nov. 1, 2022

(87) PCT Pub. No.: WO2021/222895
PCT Pub. Date: Nov. 4, 2021

(65) Prior Publication Data
US 2023/0176059 A1 Jun. 8, 2023

Related U.S. Application Data

(60) Provisional application No. 63/019,052, filed on May 1, 2020.

(51) Int. Cl.
*G01N 33/5755* (2026.01)

(52) U.S. Cl.
CPC ............................... *G01N 33/5755* (2026.01)

(58) Field of Classification Search
CPC ......... G01N 33/57442; G01N 2800/52; C12Q 2600/106; C12Q 2600/156; C12Q 2600/158; C12Q 2600/16; C12Q 1/6886; A61P 35/00
See application file for complete search history.

(56) References Cited

U.S. PATENT DOCUMENTS

2013/0210900 A1 8/2013 Vogelstein et al.
2018/0042929 A1 2/2018 Liu et al.

FOREIGN PATENT DOCUMENTS

WO WO 2008/109519 9/2008
WO WO 2012/071096 5/2012
WO WO-2016004387 A1 * 1/2016 .............. A61P 35/00

OTHER PUBLICATIONS

Cancer Genome Atlas Research Network (Nature 497(7447):67-73, 2013/ IDS reference #11 submitted Sep. 19, 2023) with Supplementary Information (SI), 1-84 (2013).*
Brooks et al., (CA: A Cancer Journal for Clinicians 69(4): 251-343, Jul. 2019).*
Remmerie et al. (International Journal of Molecular Sciences 19:1-22, published 13, Aug. 2018).*
Gonzalez-Bosquet et al. ECPPF stratification identifies occult high-risk subgroups in stage I, grade 1 or 2, <50% invasive endometrial cancer: Candidates for adjuvant therapy. Gynecologic Oncology 196:113-120, 2025.*
Gonzalez-Bosquet et al., "ECPPF (E2F1, CCNA2, POLE, PPP2R1A, FBXW7) stratification: Profiling high-risk subtypes of histomorphologically low-risk and treatment-insensitive endometrioid endometrial cancer," PLoS One, Dec. 2022, 17(12):e0278408, 16 pages.
Gonzalez-Bosquet et al., "Prognostic stratification of endometrial cancers with high microsatellite instability or no specific molecular profile," Front. Oncol., May 2023, 13:1105504, 12 pages.
Dinoi et al., "In search for biomarkers and potential drug targets for uterine serous endometrial cancer," J. Cancer Res. Clin. Oncol., Jun. 2021, 147(6):1647-1658.
Extended European Search Report in European Appln. No. 21797226. 4, dated Apr. 29, 2024, 10 pages.
Alvarez-Fernandez et al., "Therapeutic relevance of the PP2A-B55 inhibitory kinase MASTL/Greatwall in breast cancer," Cell Death Differ., May 2018; 25(5):828-40.
Bakkum-Gamez et al., "Efficacy of contemporary chemotherapy in stage IIIC endometrial cancer: a histologic dichotomy," Gynecol. Oncol., Mar. 2014, 132(3):578-84.
Bellucci et al., "Activation of p21 by HDAC inhibitors requires acetylation of H2A.Z," PLoS One, Jan. 2013, 8(1):e54102, 7 pages.
Bosse et al., "Loss of ARIDIA expression and its relationship with PI3K-Akt pathway alterations, TP53 and microsatellite instability in endometrial cancer," Mod. Pathol., Nov. 2013, 26(11):1525-35.
Bracken et al., "E2F target genes: unraveling the biology," Trends Biochem. Sci., Aug. 2004, 29(8):409-17.
Britton et al., "Molecular classification defines outcomes and opportunities in young women with endometrial carcinoma," Gynecol. Oncol., Jun. 2019, 153(3):487-495.

(Continued)

*Primary Examiner* — Alana Harris Dent
(74) *Attorney, Agent, or Firm* — Fish & Richardson P.C.

(57) ABSTRACT

This document relates to methods and materials for assessing and/or treating mammals (e.g., humans) having endometrial cancer. For example, methods and materials for identifying endometrial cancers likely to respond to a particular cancer treatment (e.g., a platinum based cancer therapy) are provided. This document also relates to materials and methods for using one or more cancer treatments to treat a mammal (e.g., a human) identified as likely to respond to a particular cancer treatment.

22 Claims, 30 Drawing Sheets
Specification includes a Sequence Listing.

(56) References Cited

OTHER PUBLICATIONS

BroadInstitute.com [online], "Cancer Cell Line Encyclopedia," available no later than Jan. 2021, retrieved on Aug. 1, 2023, retrieved from URL<https://sites.broadinstitute.org/ccle>, 6 pages.

Cancer Genome Atlas Research Network et al., "Integrated genomic characterization of endometrial carcinoma," Nature. Oct. 2013, 497(7447):67-73.

Cancer Genome Atlas Research Network, "Integrated genomic analyses of ovarian carcinoma," Nature, Dec. 2011, 474(7353):609-615.

Cao et al., "Fbxw7 Tumor Suppressor: A Vital Regulator Contributes to Human Tumorigenesis," Medicine (Baltimore), Feb. 2016, 95(7):e24, 10 pages.

Chen et al., "Wnt-induced deubiquitination FoxMl ensures nucleus beta-catenin transactivation," EMBO J., Mar. 2016, 35(6):668-84.

Chou, "Theoretical basis, experimental design, and computerized simulation of synergism and antagonism in drug combination studies," Pharmacol. Rev., Sep. 2006, 58(3):621-81.

Cremona et al., "Fbw7 and its counteracting forces in stem cells and cancer: Oncoproteins in the balance," Semin. Cancer Biol., Feb. 2016, 36:52-61.

Damia et al., "Platinum Resistance in Ovarian Cancer: Role of DNA Repair," Cancers (Basel), Jan. 2019, 11(1):119, 15 pages.

Fischer et al., "The p53-p21-Dream-CDE/CHR pathway regulates G2/M cell cycle genes," Nucleic Acids Res., Jan. 2016, 44(1):164-174.

Garrido et al., "Non-centrosomal TPX2-Dependent Regulation of the Aurora A Kinase: Functional Implications for Healthy and Pathological Cell Division," Front. Oncol., Apr. 2016, 6:88, 8 pages.

Gonzalez-Bosquet et al., "Analysis of chemotherapeutic response in ovarian cancers using publicly available high-throughput data," Cancer Res., Jul. 2014, 74(14):3902-3912.

Gonzalez-Bosquet et al., "Association of a novel endometrial cancer biomarker panel with prognostic risk, platinum insensitivity, and targetable therapeutic options," Plos One, Jan. 2021, 16(1):e0245664, 16 pages.

Gonzalez-Bosquet et al., "PP2A and E3 ubiquitin ligase deficiencies: Seminal biological drivers in endometrial cancer," Gynecol. Oncol., Jul. 2021, 162(1):182-189.

Haines et al., "Precision therapy for aggressive endometrial cancer by reactivation of protein phosphatase 2A," Cancer Res., Aug. 2019, 79(16):4009-4010.

He et al. [Retracted], "Identification of Aurora-A as a direct target of E2F3 during G2/M cell cycle progression," J Biol Chem., Nov. 2008, 283(45):31012-31020.

Hogberg et al., "Sequential adjuvant chemotherapy and radiotherapy in endometrial cancer-Results from two randomised studies," Eur. J. Cancer, Sep. 2010, 46(13):2422-2431.

Huber et al., "Orchestrating high-throughput genomic analysis with Bioconductor," Nat. Methods, Feb. 2015; 12(2):115-121.

Hutt et al., "The role of biomarkers in endometrial cancer and hyperplasia: a literature review," Acta Oncol., Mar. 2019, 58(3):342-352.

Khanna et al., "Clinical significance of cancerous inhibitor of protein phosphatase 2A in human cancers," Int. J. Cancer, Feb. 2016; 138(3):525-532.

Koo et al., "FOXM1: From cancer initiation to progression and treatment," Biochim. Biophys. Acta., 2012, 1819(1):28-37.

Laine et al., "Molecular pathways: harnessing E2F1 regulation for prosenescence therapy in p53-defective cancer cells," Clin. Cancer Res., Jul. 2014, 20(14):3644-3650.

Laine et al., "Senescence sensitivity of breast cancer cells is defined by positive feedback loop between CIP2A and E2F1," Cancer Discov., Feb. 2013, 3(2):182-197.

Li et al., "Cancerous inhibitor of protein phosphatase 2A regulates cisplatin resistance in ovarian cancer," Oncol. Lett., Jan. 2019, 17(1):1211-1216.

Li et al., "POLE mutations improve the prognosis of endometrial cancer via regulating cellular metabolism through AMF/AMFR signal transduction," BMC Med. Genet., Dec. 2019, 20(1):202, 13 pages.

McCubrey et al., "GSK-3 as potential target for therapeutic intervention in cancer," Oncotarget, May 2014, 5(10):2881-2911.

Mints et al., "Mitochondrial ribosomal protein S18-2 is highly expressed in endometrial cancers along with free E2F1," Oncotarget, Mar. 2016, 7(16):22150-2215.

Mori et al., "Expression of HER-2 affects patient survival and paclitaxel sensitivity in endometrial cancer," Br. J. Cancer, Sep. 2010, 103(6):889-898.

Nestal de Moraes et al., "Insights into a Critical Role of the FOXO3a-FOXMl Axis in DNA Damage Response and Genotoxic Drug Resistance," Curr. Drug Targets., Jan. 2016, 17(2):164-177.

PCT International Preliminary Report on Patentability in International Appln. No. PCT/US2021/030467, mailed on Nov. 10, 2022, 8 pages.

PCT International Search Report and Written Opinion in International Appln. No. PCT/US2021/030467, mailed on Sep. 10, 2021, 11 pages.

Poppy Roworth et al., "To live or let die—complexity within the E2F1 pathway," Mol. Cell. Oncol., Jan. 2015, 2(1):e970480, 11 pages.

Randall et al., "Randomized phase III trial of whole-abdominal irradiation versus doxorubicin and cisplatin chemotherapy in advanced endometrial carcinoma: a Gynecologic Oncology Group Study," J. Clin. Oncol., Jan. 2006, 24(1):36-44.

Saha et al., "Structural and sequential context of p53: A review of experimental and theoretical evidence," Prog. Biophys. Mo. Biol., Mar. 2015, 117(2-3):250-263.

Sangodkar et al., "All roads lead to PP2A: exploiting the therapeutic potential of this phosphatase," FEBS J., Oct. 2016; 283(6):1004-1024.

Shih et al., "Immunhistochemical expression of cyclins, cyclin-dependent kinases, tumor-suppressor gene products, Ki-67, and sex steroid receptors in endometrial carcinoma: postive staining for cyclin A as a poor prognostic indicator," Hum. Pathol., May 2003, 34(5):471-478.

Siegel et al., "Cancer statistics, 2018," CA Cancer J. Clin., Jan. 2018, 68(1):7-30.

Siegel et al., "Cancer statistics, 2019," CA Cancer J. Clin., Jan. 2019, 69(1):7-34.

Simon et al., "Analysis of Gene Expression Data Using BRB-Array Tools," Cancer Inform., Feb. 2007, 3:11-17.

Strebhardt, "Multifaceted polo-like kinases: drug targets and antitargets for cancer therapy," Nat. Rev. Drug Discov., 2010, 9:643-660.

Suzuki et al., "Cyclin A2 confers cisplatin resistance to endometrial carcinoma cells via up-regulation of an Akt-binding protein, periplakin," J Cell Mol Med, Sep. 2010, 14(9):2305-2317.

Talhouk et al., "Confirmation of ProMisE: A simple, genomics-based clinical classifier for endometrial cancer," Cancer, Jan. 2017, 123(5):802-813.

Talhouk et al., "New classification of endometrial cancers: the development and potential applications of genomic-based classification in research and clinical care," Gynecol. Oncol. Res. Pract., Dec. 2016, 3:14, 12 pages.

Taylor et al., "The highly recurrent PP2A Aα-subunit mutation P179R alters protein structure and impairs PP2A enzyme function to promote endometrial tumorigenesis," Cancer Res., Aug. 2019, 79(16):4242-4257.

Tortorella et al., "Uterine serous carcinoma: Reassessing effectiveness of platinum-based adjuvant therapy," Gynecol. Oncol., May 2018, 149(2):291-296.

Yeh et al., "FBXW7: a critical tumor suppressor of human cancers," Mol. Cancer, Aug. 2018, 17(1):115, 19 pages.

Yu et al., "CIP2A is overexpressed in human endometrioid adenocarcinoma and regulates cell proliferation, invasion and apoptosis," Pathol. Res. Prac., Feb. 2018, 214(2):233-239.

Zhao et al., "Landscape of somatic single-nucleotide and copy-number mutations in uterine serous carcinoma," Proc. Natl. Acad. Sci. U.S.A, Feb. 2013, 110(8):2916-2921.

(56)     References Cited

OTHER PUBLICATIONS

Zheng et al., "Arginine Methylation-Dependent Reader-Writer Interplay Governs Growth Control by E2F-1," Molecular Cell, Oct. 2013, 52:37-52.

* cited by examiner

Integrated p53-p21-DREAM and PI3K-AKT-FBW7 pathway

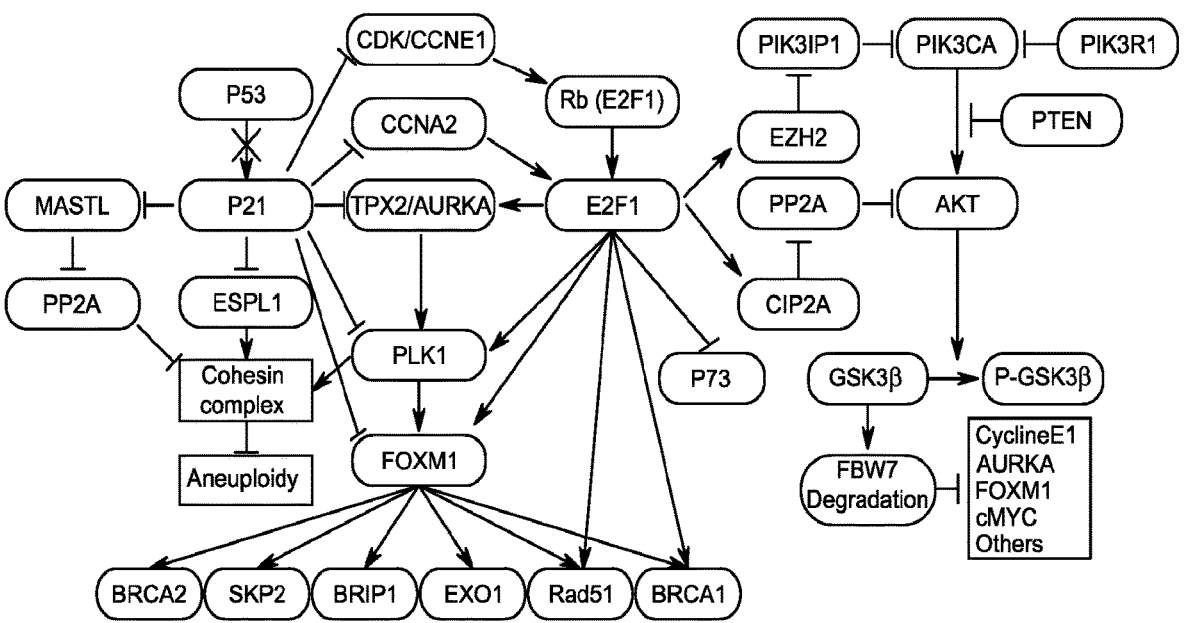

FIG. 1A

Oncogene expression by p53 status

| | mRNA expression | | |
|---|---|---|---|
| Oncogene | P53-mu | P53-WT | p-value |
| CDKN1A | 4.141 1.257) | 5.777 1.077) | <0.001 |
| CDK2 | 3.627 0.808) | 3.101 0.753) | <0.001 |
| CCNA2 | 2.756 0.894) | 2.030 1.066) | <0.001 |
| TPX2 | 4.394 0.808) | 3.044 1.003) | <0.001 |
| AURKA | 3.253 0.780) | 1.978 0.953) | <0.001 |
| PLK1 | 4.402 0.870) | 3.251 1.047) | <0.001 |
| ESPL1 | 2.080 0.836) | 0.678 1.106) | <0.001 |
| MASTL | 1.668 0.855) | 1.157 0.770) | <0.001 |
| E2F1 | 3.292 1.006) | 1.803 1.045) | <0.001 |
| CCNE1 | 4.207 1.343) | 2.302 1.218) | <0.001 |
| KIAA1524 | 2.245 (1.078) | 1.276 (1.142) | <0.001 |
| EZH2 | 2.834 0.711) | 2.318 0.694) | <0.001 |
| FOXM1 | 4.103 0.711) | 3.194 0.956) | <0.001 |
| Rad 51 | 1.782 0.797) | 1.227 1.008) | <0.001 |
| BRCA1 | 1.168 0.953) | 1.100 0.877) | 0.62 |
| TP73 | -0.382 (1.767) | 1.198 (1.571) | <0.001 |

FIG. 1B

Comparative oncogene expression

| | Correlation coefficients | | | |
|---|---|---|---|---|
| | P53-mu | | P53-WT | |
| Oncogene | E2F1 | CCNA2 | E2F1 | CCNA2 |
| AURKA | 0.433 | 0.632 | 0.739 | 0.872 |
| TPX2 | 0.576 | 0.585 | 0.757 | 0.905 |
| PLK1 | 0.602 | 0.421 | 0.83 | 0.69 |
| FOXM1 | 0.689 | 0.562 | 0.811 | 0.875 |
| ESPL1 | 0.627 | 0.428 | 0.81 | 0.779 |
| MASTL1 | 0.125 | 0.576 | 0.431 | 0.792 |
| EZH2 | 0.433 | 0.436 | 0.578 | 0.715 |
| CIP2A | 0.211 | 0.655 | 0.557 | 0.911 |
| BRCA1 | 0.274 | 0.549 | 0.625 | 0.859 |
| BRIP1 | 0.275 | 0.509 | 0.567 | 0.861 |
| EXO1 | 0.381 | 0.737 | 0.659 | 0.88 |
| BRCA2 | 0.108 | 0.667 | 0.509 | 0.818 |
| RAD51 | 0.47 | 0.619 | 0.79 | 0.851 |
| SKP2 | 0.347 | 0.662 | 0.485 | 0.822 |
| MRE11 | 0.148 | 0.582 | 0.135 | 0.577 |
| RAD50 | -0.103 | 0.481 | 0.026 | 0.464 |
| NBS1 | -0.020 | 0.639 | 0.051 | 0.599 |

FIG. 1C

Cox Proportional HR Survival Analysis

| Molecular Cohort[a] | HR | *P* Value | 5-y PFS, % | 95% PFS |
|---|---|---|---|---|
| *CCNA2-L* | 1.00 | ... | 87 | 80-95 |
| *CCNA2-H* | 3.68 | .0005 | 53 | 38-73 |
| *FBXW7*mu/*PPP2R1A*mu | 4.53 | .0002 | 42 | 21-81 |
| *POLE*-mu | 0.63 | .5525 | 85 | 66-100 |

[a] Overall comparison: log-rank test *P* value = $1.5 \times 10^{-5}$

FIG. 2C

Multivariate Analysis

| Molecular Cohort | HR | *P* Value | 95% CI |
|---|---|---|---|
| *CCNA2-L* (Ref) | 1.00 | ... | ... |
| *CCNA2-H* | 3.28 | .0016 | 1.57-6.85 |
| *FBXW7*mu/*PPP2R1A*mu | 4.00 | .0007 | 1.80-8.89 |
| *POLE*-mu | 0.61 | .5165 | 0.13-2.74 |
| Stage | 1.46 | .0042 | 1.13-1.89 |

FIG. 2D

Cox Proportional HR Survival Analysis

| Molecular Cohort[a] | HR | P Value | 5-y PFS, % | 95% PFS |
|---|---|---|---|---|
| CIP2A-L | 1.00 | ... | 92 | 86-98 |
| CIP2A-H | 5.34 | .0002 | 56 | 44-72 |
| FBXW7mu/PPP2R1Amu | 6.98 | .0001 | 42 | 21-81 |
| POLE-mu | 0.98 | .9770 | 85 | 66-100 |

[a] Overall comparison: log-rank test P value = $4 \times 10^{-6}$

FIG. 3C

Multivariate Analysis

| Molecular Cohort | HR | P Value | 95% CI |
|---|---|---|---|
| CIP2A-L (Ref) | 1.00 | ... | ... |
| CIP2A-H | 4.55 | .0010 | 1.85-11.20 |
| FBXW7mu/PPP2R1Amu | 6.02 | .0003 | 2.29-15.85 |
| POLE-mu | 0.91 | .9031 | 0.18-4.50 |
| Stage | 1.40 | .0119 | 1.08-1.81 |

FIG. 3D

Cox Proportional HR Survival Analysis

| Molecular Cohort[a] | HR | P Value | 5-y PFS, % | 95% PFS |
|---|---|---|---|---|
| CCNA2-L/E2F1-L (Ref) | 1.00 | ... | 92 | 87-99 |
| CCNA2-H/E2F1-H | 6.27 | .0001 | 53 | 40-70 |
| FBXW7-mu/PPP2R1A-mu | 7.41 | <.0001 | 42 | 21-81 |
| POLE-mu | 1.04 | .9650 | 85 | 66-100 |

[a] Overall comparison: log-rank test P value = $5.8 \times 10^{-7}$

FIG. 4C

Multivariate Analysis

| Molecular Cohort | HR | P Value | 95% CI |
|---|---|---|---|
| CCNA2-L/E2F1-L (Ref) | 1.00 | ... | ... |
| CCNA2-H/E2F1-H | 5.33 | .0003 | 2.16-13.13 |
| FBXW7-mu/PPP2R1A-mu | 6.46 | .0002 | 2.46-16.97 |
| POLE-mu | 0.96 | .9637 | 0.19-4.78 |
| Stage | 1.38 | .0170 | 1.06-1.80 |

FIG. 4D

ARK-2 treated with panobinostat

HEC-1B treated with panobinostat

ARK-2 treated with carboplatin w/o panobinostat

HEC-1B treated with carboplatin w/o panobnostat

ARK-2 treated with carboplatin w/o GSK2141795

HEC-1B treated with carboplatin w/o GSK2141795

Cox proportional HR survival analysis

| | HR | p-value | 95% CI | 5-year PFS | 90% PFS |
|---|---|---|---|---|---|
| Ref Group: *CCNA2-L* and *FBXW7*-mu and *PPP2R1A* | 1.00 | | | 87% | 79%, 96% |
| Group: CCNA2-H and/or FBXW7-mu and/or PPP2R1A-mu* | 4.71 | 0.000 | 2.08,10.63 | 53% | 37%, 74% |
| Group: P53-mu* | 2.97 | 0.011 | 1.28, 6.88 | 60% | 46%, 80% |
| Group: POLE-mu | 0.69 | 0.641 | 0.15, 3.26 | 85% | 66%, 100% |

\* Statistically significant

FIG. 9C

Cox proportional HR survival analysis

| | HR | p-value | 95% CI |
|---|---|---|---|
| Ref Group: *CCNA2-L* and *FBXW7*-mu and *PPP2R1A* | 1.00 | | |
| Group: CCNA2-H and/or FBXW7-mu and/or PPP2R1A-mu* | 4.36 | 0.000 | 1.92, 9.87 |
| Group: P53-mu | 1.98 | 0.131 | 0.82, 4.79 |
| Group: POLE-mu | 0.60 | 0.514 | 0.13, 2.82 |
| Stage* | 1.56 | 0.002 | 1.18, 2.05 |

\* Statistically significant

FIG. 9D

Cox proportional HR survival analysis

|  | HR | p-value | 95% CI | 5-year PFS | 90% PFS |
|---|---|---|---|---|---|
| Ref Group: CIP2A-L and FBXW7-wt and PPP2R1A-wt | 1.00 |  |  | 89% | 80%, 97% |
| Group: CIP2A-H and/or FBXW7-mu and/or PPP2R1A-mu* | 5.59 | 0.000 | 2.39,13.10 | 51% | 37%, 72% |
| Group: P53-mu* | 3.38 | 0.007 | 1.40, 8.16 | 60% | 46%, 80% |
| Group: POLE-mu | 0.79 | 0.767 | 0.16, 3.80 | 85% | 66%, 100% |

* Statistically significant

FIG. 10C

Cox proportional HR survival analysis

|  | HR | p-value | 95% CI |
|---|---|---|---|
| Ref Group: CIP2A-L and FBXW7-wt and PPP2R1A-wt | 1.00 |  |  |
| Group: CIP2A-H and/or FBXW7-mu and/or PPP2R1A-mu* | 5.16 | 0.000 | 2.20,12.13 |
| Group: P53-mu | 2.26 | 0.083 | 0.90, 5.70 |
| Group: POLE-mu | 0.68 | 0.631 | 0.14, 3.29 |
| Stage* | 1.55 | 0.002 | 1.18, 2.04 |

* Statistically significant

FIG. 10D

| Cohorts | HR (95% CI) | P |
|---|---|---|
| | | <0.001 |
| *CCNA2-L/E2F1-L/TP53wt* | Reference | |
| *POLE*mu | 1.11 (0,22, 5.74) | |
| *CCNA2-L/E2F1-L/TP53*mu | 1.65 (0.19, 14.11) | |
| *CCNA2-H/E2F1-H/TP53*mu | 5.50 (1.48, 20.51) | |
| *CCNA2-H/E2F1-H/TP53*wt | 7.56 (2.71, 21.13) | |
| *PPP2R1Amu/FBXW7*mu | 7.62 (2.42, 24.05) | |

FIG. 13E

| Characteristic | Adjusted HR (95% CI) | P |
|---|---|---|
| Stage | | 0.008 |
| I/II | Reference | |
| III | 1.55 (0.58, 4.13) | |
| IV | 5.22 (1.83, 14.91) | |
| ECPPF cohorts | | <0.001 |
| *CCNA2-L/E2F1-L* | Reference | |
| *CCNA2-H/E2F1-H* | 5.71 (2.23, 14.61) | |
| *PPP2R1Amu/FBXW7*mu | 7.87 (2.62, 23.63) | |

FIG. 13F

METHODS AND MATERIALS FOR TREATING ENDOMETRIAL CANCER BY ASSESSING COMBINATIONS OF MUTATIONS AND EXPRESSION LEVELS

CROSS-REFERENCE TO RELATED APPLICATIONS

This application is a National Stage application under 35 U.S.C. § 371 of International Application No. PCT/US2021/030467, having an International Filing Date of May 3, 2021, which claims the benefit of U.S. Patent Application Ser. No. 63/019,052, filed on May 1, 2020. The disclosure of the prior application is considered part of (and is incorporated by reference in) the disclosure of this application.

SEQUENCE LISTING

This application contains a Sequence Listing that has been submitted electronically as an ASCII text file named "07039-1956WO1_ST25.txt." The ASCII text file, created on Jun. 2, 2021, is 3,559 bytes in size. The material in the ASCII text file is hereby incorporated by reference in its entirety.

BACKGROUND

1. Technical Field

This document relates to methods and materials for assessing and/or treating mammals (e.g., humans) having endometrial cancer. For example, methods and materials provided herein can be used to determine whether or not endometrial cancer is likely to respond to a particular cancer treatment (e.g., a platinum based cancer therapy). Also provided are materials and methods for using one or more cancer treatments to treat a mammal (e.g., a human) identified as likely to respond to a particular cancer treatment.

2. Background Information

An estimated 61,880 new cases and 12,160 deaths are predicted to be attributable to endometrial cancers (EC) in the United States this calendar year (Siegel et al., *CA Cancer J Clin.;* 69(1):7-34 (2019)). While the number of new cases continues to increase annually, alarming is the 1.9% increase per annum in the age-adjusted annual mortality during the past decade (Siegel et al., *CA Cancer J Clin.;* 68(1):7-30 (2018)). A need exists to reverse this trajectory. Standard treatment for high-risk endometrial cancer (EC) is definitive surgery followed by systemic platinum-based chemotherapy (PbCT) and/or radiotherapy. Sensitivity to PbCT positively correlates with deficiencies in the homologous recombination (HR) pathway (Damia et al., *Cancers;* 11(1):E119 (2019)). However, recognizing the majority of EC are HR proficient, a search for more tailored molecular-based therapy is paramount.

SUMMARY

This document provides methods and materials related to assessing and/or treating endometrial cancer. In some cases, this document provides methods and materials for determining whether or not a mammal (e.g., a human) having endometrial cancer is likely to respond to a particular cancer treatment (e.g., a platinum based cancer therapy), and, optionally, administering to the mammal one or more cancer treatments selected based, at least in part, on whether or not the mammal is likely to respond to a particular cancer treatment. For example, a sample (e.g., a sample containing one or more cancer cells) obtained from a mammal having endometrial cancer can be assessed to determine if the mammal is likely to respond to a particular cancer treatment based, at least in part, on the presence or absence of one or more (e.g., one, two, three, four, five, six, seven, eight, nine, or more) genetic markers or phenotypes (e.g., one or more mutations in one or more nucleic acids or increased level of expression of one or more nucleic acids encoding a polypeptide) in the sample.

As demonstrated herein, the presence of one or more mutations in a F-box/WD repeat-containing protein 7 (FBXW7) nucleic acid, the presence of one or more mutations in a protein phosphatase 2A subunit (PPP2R1A) nucleic acid, and overexpression of a cyclin-A2 (CCNA2) nucleic acid (e.g., resulting in increased level of nucleic acid encoding a CCNA2 polypeptides) can be used to identify endometrial cancer patients as having PbCT resistance. Also as demonstrated herein, the presence of one or more mutations in a FBXW7 nucleic acid, the presence of one or more mutations in a PPP2R1A nucleic acid, and overexpression of a cancerous inhibitor of protein phosphatase 2A (CIP2A) nucleic acid (e.g., resulting in an increased level of nucleic acid encoding a CIP2A polypeptide) can be used to identify endometrial cancer patients as having PbCT resistance. These results demonstrate that the presence or absence of one or more genetic markers or phenotypes (e.g., the presence or absence of one or more mutations in one or more nucleic acids and/or the presence or absence of increased level of expression of one or more nucleic acids encoding a polypeptide) in a sample from a mammal having endometrial cancer can used to determine PbCT responsiveness of that mammal.

Having the ability to identify a mammal having endometrial cancer as being likely to respond to a particular cancer treatment based, at least in part, on the presence or absence of one or more genetic markers and/or phenotypes provides a unique and unrealized opportunity to provide an individualized approach in selecting effective cancer therapies.

In general, one aspect of this document features methods for assessing a mammal having endometrial cancer. The methods can include, or consist essentially of, (a) detecting (a-i) a presence or absence of a mutation in nucleic acid encoding a F-box/WD repeat-containing protein 7 (FBW7) polypeptide or nucleic acid regulating expression of the FBW7 polypeptide, (a-ii) a presence or absence of a mutation in nucleic acid encoding a protein phosphatase 2A subunit (PPP2R1A) polypeptide or nucleic acid regulating expression of the PPP2R1A polypeptide, and (a-iii) a presence or absence of an increased level of expression of nucleic acid encoding a cyclin-A2 (CCNA2) polypeptide in a sample from the mammal; (b) classifying the mammal as not being likely to respond to a platinum based cancer therapy if (b-i) the presence of the mutation of (a-i) is detected, (b-ii) the presence of the mutation of (a-ii) is detected, and (b-iii) the presence of the increased level is detected; and (c) classifying the mammal as being likely to respond to the platinum based cancer therapy if (c-i) the absence of the mutation of (a-i) is detected, (c-ii) the absence of the mutation of (a-ii) is detected, and (c-iii) the absence of the increased level of the expression of the nucleic acid encoding the CCNA2 polypeptide is detected. The mammal can be a human. The sample can include cancer cells of the endometrial cancer. The method also can include detecting (a-iv) a presence or absence of a mutation in nucleic acid encoding a DNA polymerase epsilon catalytic subunit A (POLE) polypeptide or nucleic acid regulating expression of the POLE polypeptide, and (a-v) a presence or absence of a mutation in nucleic acid encoding a p53 polypeptide or nucleic acid regulating expression of the p53 polypeptide. For example, the method can include detecting (i) the presence of the mutation of (a-i), (ii) the presence of the mutation of (a-ii), (iii) the presence of the increased level of expression of the nucleic acid encoding the CCNA2 polypeptide, (iv) the presence of the mutation of (a-iv), and (v) the presence of the mutation of (a-v). Such a method can include classifying the mammal as not being likely to respond to the platinum based cancer therapy. For example, the method can include detecting (i) the absence of the mutation of (a-i), (ii) the absence of the mutation of (a-ii), (iii) the absence of the increased level of expression of the nucleic acid encoding the CCNA2 polypeptide, (iv) the absence of the mutation of (a-iv), and (v) the absence of the mutation of (a-v). Such a method can include classifying the mammal as being likely to respond to the platinum based cancer therapy. The method also can include detecting (a-iv) a presence or absence of a mutation in nucleic acid encoding a POLE polypeptide or nucleic acid regulating expression of the POLE polypeptide, and (a-v) a presence or absence of an increased level of expression of nucleic acid encoding a transcription factor E2F1 (E2F1) polypeptide in a sample from the mammal. For example, the method can include detecting (i) the presence of the mutation of (a-i), (ii) the presence of the mutation of (a-ii), (iii) the presence of the increased level of expression of the nucleic acid encoding the CCNA2 polypeptide, (iv) the presence of the mutation of (a-iv), and (v) the presence of the increased level of expression of the nucleic acid encoding the E2F1 polypeptide. Such a method can include classifying the mammal as not being likely to respond to the platinum based cancer therapy. For example, the method can include detecting (i) the absence of the mutation of (a-i), (ii) the absence of the mutation of (a-ii), (iii) the absence of the increased level of expression of the nucleic acid encoding the CCNA2 polypeptide, (iv) the absence of the mutation of (a-iv), and (v) the absence of the increased level of expression of the nucleic acid encoding the E2F1 polypeptide. Such a method can include classifying the mammal as being likely to respond to the platinum based cancer therapy.

In another aspect, this document features methods for assessing a mammal having endometrial cancer where the methods can include, or consist essentially of, (a) detecting (a-i) a presence or absence of a mutation in nucleic acid encoding a FBW7 polypeptide or nucleic acid regulating expression of the FBW7 polypeptide, (a-ii) a presence or absence of a mutation in nucleic acid encoding a PPP2R1A polypeptide or nucleic acid regulating expression of the PPP2R1A polypeptide, and (a-iii) a presence or absence of an increased level of expression of nucleic acid encoding a cancerous inhibitor of protein phosphatase 2A (CIP2A) polypeptide in a sample from the mammal; (b) classifying the mammal as not being likely to respond to a platinum based cancer therapy if (b-i) the presence of the mutation of (a-i) is detected, (b-ii) the presence of the mutation of (a-ii) is detected, and (b-iii) the presence of the increased level of expression of the nucleic acid encoding the CIP2A polypeptide is detected; and (c) classifying the mammal as being likely to respond to the platinum based cancer therapy if (c-i) the absence of the mutation of (a-i) is detected, (c-ii) the absence of the mutation of (a-ii) is detected, and (c-iii) the absence of the increased level of expression of the nucleic acid encoding the CIP2A polypeptide is detected. The mammal can be a human. The sample can include cancer cells of the endometrial cancer. The method also can include detecting (a-iv) a presence or absence of a mutation in nucleic acid encoding a POLE polypeptide or nucleic acid regulating expression of the POLE polypeptide, and (a-v) a presence or absence of a mutation in nucleic acid encoding a p53 polypeptide or nucleic acid regulating expression of the p53 polypeptide. For example, the method can include detecting (i) the presence of the mutation of (a-i), (ii) the presence of the mutation of (a-ii), (iii) the presence of the increased level of expression of the nucleic acid encoding the CIP2A polypeptide, (iv) the presence of the mutation of (a-iv), and (v) the presence of the mutation of (a-v). Such a method can include classifying the mammal as not being likely to respond to the platinum based cancer therapy. For example, the method can include detecting (i) the absence of the mutation of (a-i), (ii) the absence of the mutation of (a-ii), (iii) the absence of the increased level of expression of the nucleic acid encoding the CIP2A polypeptide, (iv) the absence of the mutation of (a-iv), and (v) the absence of the mutation of (a-v). Such a method can include classifying the mammal as being likely to respond to the platinum based cancer therapy.

In another aspect, this document features methods for treating a mammal having endometrial cancer where the methods can include, or consist essentially of, (a) detecting (a-i) a mutation in nucleic acid encoding a FBW7 polypeptide or nucleic acid regulating expression of the FBW7 polypeptide, (a-ii) a mutation in nucleic acid encoding a PPP2R1A polypeptide or nucleic acid regulating expression of the PPP2R1A polypeptide, and (a-iii) an increased level of expression of nucleic acid encoding a CCNA2 polypeptide in a sample obtained from the mammal; and (b) administering a cancer treatment to the mammal, where the cancer treatment is not a platinum based cancer therapy. The method also can include detecting (a-iv) a mutation in nucleic acid encoding a POLE polypeptide or nucleic acid regulating expression of the POLE polypeptide, and (a-v) a mutation in nucleic acid encoding a p53 polypeptide or nucleic acid regulating expression of the p53 polypeptide. The method also can include detecting (a-iv) a mutation in nucleic acid encoding a POLE polypeptide or nucleic acid regulating expression of the POLE polypeptide, and (a-v) an increased level of expression of nucleic acid encoding a E2F1 polypeptide in a sample from the mammal. The mammal can be a human. The sample can include cancer cells of the endometrial cancer. The cancer treatment can include surgery. The cancer treatment can include radiation treatment.

In another aspect, this document features methods for treating cancer where the methods can include, or consist essentially of, administering a cancer treatment to a mammal identified as having (i) a mutation in nucleic acid encoding a FBW7 polypeptide or nucleic acid regulating expression of the FBW7 polypeptide, (ii) a mutation in nucleic acid encoding a PPP2R1A polypeptide or nucleic acid regulating expression of the PPP2R1A polypeptide, and (iii) an increased level of expression of nucleic acid encoding a CCNA2 polypeptide in a sample obtained from the mammal, where the cancer treatment is not a platinum based cancer therapy. The mammal also can be identified as having (iv) a mutation in nucleic acid encoding a POLE polypeptide or nucleic acid regulating expression of the POLE polypeptide, and (v) a mutation in nucleic acid encoding a p53 polypeptide or nucleic acid regulating expression of the p53 polypeptide. The mammal also can be identified as having (iv) a mutation in nucleic acid encoding a POLE polypeptide or nucleic acid regulating expression of the POLE polypeptide, and (v) an increased level of expression of nucleic acid encoding a E2F1 polypeptide in a sample from the mammal. The mammal can be a human. The sample can include cancer cells of the endometrial cancer. The cancer treatment can include surgery. The cancer treatment can include radiation treatment.

In another aspect, this document features methods for treating a mammal having endometrial cancer where the methods can include, or consist essentially of, (a) detecting (a-i) an absence of a mutation in nucleic acid encoding a FBW7 polypeptide or nucleic acid regulating expression of the FBW7 polypeptide, (a-ii) an absence of a mutation in nucleic acid encoding a PPP2R1A polypeptide or nucleic acid regulating expression of the PPP2R1A polypeptide, and (a-iii) an absence of an increased level of expression of nucleic acid encoding a CCNA2 polypeptide in a sample obtained from the mammal; and (b) administering a platinum based cancer therapy to the mammal. The method also can include detecting (a-iv) an absence of a mutation in nucleic acid encoding a POLE polypeptide or nucleic acid regulating expression of the POLE polypeptide, and (a-v) an absence of a mutation in nucleic acid encoding a p53 polypeptide or nucleic acid regulating expression of the p53 polypeptide. The method also can include detecting (a-iv) an absence of a mutation in nucleic acid encoding a POLE polypeptide or nucleic acid regulating expression of the POLE polypeptide, and (a-v) an absence of an increased level of expression of nucleic acid encoding a E2F1 polypeptide in a sample from the mammal. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof.

In another aspect, this document features methods for treating endometrial cancer where the methods can include, or consist essentially of, administering a platinum based cancer therapy to a mammal identified as lacking (i) a mutation in nucleic acid encoding a FBW7 polypeptide or nucleic acid regulating expression of the FBW7 polypeptide, (ii) a mutation in nucleic acid encoding a PPP2R1A polypeptide or nucleic acid regulating expression of the PPP2R1A polypeptide, and (iii) an increased level of expression of nucleic acid encoding a CCNA2 polypeptide in a sample obtained from the mammal. The mammal also can be identified as lacking (iv) a mutation in nucleic acid encoding a POLE polypeptide or nucleic acid regulating expression of the POLE polypeptide, and (v) a mutation in nucleic acid encoding a p53 polypeptide or nucleic acid regulating expression of the p53 polypeptide. The mammal also can be identified as lacking (iv) a mutation in nucleic acid encoding a POLE polypeptide or nucleic acid regulating expression of the POLE polypeptide, and (v) an increased level of expression of nucleic acid encoding a E2F1 polypeptide in a sample from the mammal. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof.

In another aspect, this document features methods for treating a mammal having endometrial cancer where the methods can include, or consist essentially of, (a) detecting (a-i) a mutation in nucleic acid encoding a FBW7 polypeptide or nucleic acid regulating expression of the FBW7 polypeptide, (a-ii) a mutation in nucleic acid encoding a PPP2R1A polypeptide or nucleic acid regulating expression of the PPP2R1A polypeptide, and (a-iii) an increased level of expression of nucleic acid encoding a CIP2A polypeptide in a sample obtained from the mammal; and (b) administering a cancer treatment to the mammal, where the cancer treatment is not a platinum based cancer therapy. The method also can include detecting (a-iv) a mutation in nucleic acid encoding a POLE polypeptide or nucleic acid regulating expression of the POLE polypeptide, and (a-v) a mutation in nucleic acid encoding a p53 polypeptide or nucleic acid regulating expression of the p53 polypeptide. The mammal can be a human. The sample can include cancer cells of the endometrial cancer. The cancer treatment can include surgery. The cancer treatment can include radiation treatment.

In another aspect, this document features methods for treating cancer where the methods can include, or consist essentially of, administering a cancer treatment to a mammal identified as having (i) a mutation in nucleic acid encoding a FBW7 polypeptide or nucleic acid regulating expression of the FBW7 polypeptide, (ii) a mutation in nucleic acid encoding a PPP2R1A polypeptide or nucleic acid regulating expression of the PPP2R1A polypeptide, and (iii) an increased level of expression of nucleic acid encoding a CIP2A polypeptide in a sample obtained from the mammal, where the cancer treatment is not a platinum based cancer therapy. The mammal also can be identified as having (iv) a mutation in nucleic acid encoding a POLE polypeptide or nucleic acid regulating expression of the POLE polypeptide, and (v) a mutation in nucleic acid encoding a p53 polypeptide or nucleic acid regulating expression of the p53 polypeptide. The mammal can be a human. The sample can include cancer cells of the endometrial cancer. The cancer treatment can include surgery. The cancer treatment can include radiation treatment.

In another aspect, this document features methods for treating a mammal having endometrial cancer where the methods can include, or consist essentially of, (a) detecting (a-i) an absence of a mutation in nucleic acid encoding a FBW7 polypeptide or nucleic acid regulating expression on of the FBW7 polypeptide, (a-ii) an absence of a mutation in nucleic acid encoding a PPP2R1A polypeptide or nucleic acid regulating expression of the PPP2R1A polypeptide, and (a-iii) an absence of an increased level of expression of nucleic acid encoding a CIP2A polypeptide in a sample obtained from the mammal; and (b) administering a platinum based cancer therapy to the mammal. The method also can include detecting (a-iv) an absence of a mutation in nucleic acid encoding a POLE polypeptide or nucleic acid regulating expression of the POLE polypeptide, and (a-v) an absence of a mutation in nucleic acid encoding a p53 polypeptide or nucleic acid regulating expression of the p53 polypeptide. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof.

In another aspect, this document features methods for treating endometrial cancer where the methods can include, or consist essentially of, administering a platinum based cancer therapy to a mammal identified as lacking (i) a mutation in nucleic acid encoding a FBW7 polypeptide or nucleic acid regulating expression of the FBW7 polypeptide, (ii) a mutation in nucleic acid encoding a PPP2R1A polypeptide or nucleic acid regulating expression of the PPP2R1A polypeptide, and (iii) an increased level of expression of nucleic acid encoding a CIP2A polypeptide in a sample obtained from the mammal. The mammal also can be identified as lacking (iv) a mutation in nucleic acid encoding a POLE polypeptide or nucleic acid regulating expression of the POLE polypeptide, and (v) a mutation in nucleic acid encoding a p53 polypeptide or nucleic acid regulating expression of the p53 polypeptide. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof.

In another aspect, this document features methods for treating a mammal having endometrial cancer where the methods can include, or consist essentially of, (a) detecting (a-i) a mutation in nucleic acid encoding a FBW7 polypeptide or nucleic acid regulating expression of the FBW7 polypeptide, (a-ii) a mutation in nucleic acid encoding a PPP2R1A polypeptide or nucleic acid regulating expression of the PPP2R1A polypeptide, and (a-iii) an increased level of expression of nucleic acid encoding a CCNA2 polypeptide in a sample obtained from the mammal; (b) administering a platinum based cancer therapy to the mammal; and (c) administering a histone deacetylase inhibitor to the mammal. The method also can include detecting (a-iv) a mutation in nucleic acid encoding a POLE polypeptide or nucleic acid regulating expression of the POLE polypeptide, and (a-v) a mutation in nucleic acid encoding a p53 polypeptide or nucleic acid regulating expression of the p53 polypeptide. The method also can include detecting (a-iv) a mutation in nucleic acid encoding a POLE polypeptide or nucleic acid regulating expression of the POLE polypeptide, and (a-v) an increased level of expression of nucleic acid encoding a E2F1 polypeptide in a sample from the mammal. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof. The histone deacetylase inhibitor can be panobinostat, trichostatin A, trapoxin B, phenylbutyrate, valproic acid, vorinostat, belinostat, LAQ824, entinostat, tacedinaline, mocetinostat, or any combinations thereof.

In another aspect, this document features methods for treating endometrial cancer where the methods can include, or consist essentially of, administering a platinum based cancer therapy and a histone deacetylase inhibitor to a mammal identified as having (i) a mutation in nucleic acid encoding a FBW7 polypeptide or nucleic acid regulating expression of the FBW7 polypeptide, (ii) a mutation in nucleic acid encoding a PPP2R1A polypeptide or nucleic acid regulating expression of the PPP2R1A polypeptide, and (iii) an increased level of expression of nucleic acid encoding a CCNA2 polypeptide in a sample obtained from the mammal. The mammal also can be identified as having (iv) a mutation in nucleic acid encoding a POLE polypeptide or nucleic acid regulating expression of the POLE polypeptide, and (v) a mutation in nucleic acid encoding a p53 polypeptide or nucleic acid regulating expression of the p53 polypeptide. The mammal also can be identified as having (iv) a mutation in nucleic acid encoding a POLE polypeptide or nucleic acid regulating expression of the POLE polypeptide, and (v) an increased level of expression of nucleic acid encoding a E2F1 polypeptide in a sample from the mammal. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof. The histone deacetylase inhibitor can be panobinostat, trichostatin A, trapoxin B, phenylbutyrate, valproic acid, vorinostat, belinostat, LAQ824, entinostat, tacedinaline, mocetinostat, or any combinations thereof.

In another aspect, this document features methods for treating a mammal having endometrial cancer where the methods can include, or consist essentially of, (a) detecting (a-i) a mutation in nucleic acid encoding a FBW7 polypeptide or nucleic acid regulating expression of the FBW7 polypeptide, (a-ii) a mutation in nucleic acid encoding a PPP2R1A polypeptide or nucleic acid regulating expression of the PPP2R1A polypeptide, and (a-iii) an increased level of expression of nucleic acid encoding a CIP2A polypeptide in a sample obtained from the mammal; (b) administering a platinum based cancer therapy to the mammal; and (c) administering a histone deacetylase inhibitor to the mammal. The method also can include detecting (a-iv) a mutation in nucleic acid encoding a POLE polypeptide or nucleic acid regulating expression of the POLE polypeptide, and (a-v) a mutation in nucleic acid encoding a p53 polypeptide or nucleic acid regulating expression of the p53 polypeptide. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof. The histone deacetylase inhibitor can be panobinostat, trichostatin A, trapoxin B, phenylbutyrate, valproic acid, vorinostat, belinostat, LAQ824, entinostat, tacedinaline, mocetinostat, or any combinations thereof.

In another aspect, this document features methods for treating endometrial cancer where the methods can include, or consist essentially of, administering a platinum based cancer therapy and a histone deacetylase inhibitor to a mammal identified as having (i) a mutation in nucleic acid encoding a FBW7 polypeptide or nucleic acid regulating expression of the FBW7 polypeptide, (ii) a mutation in nucleic acid encoding a PPP2R1A polypeptide or nucleic acid regulating expression of the PPP2R1A polypeptide, and (iii) an increased level of expression of nucleic acid encoding a CIP2A polypeptide in a sample obtained from the mammal. The mammal also can be identified as having (iv) a mutation in nucleic acid encoding a POLE polypeptide or nucleic acid regulating expression of the POLE polypeptide, and (v) a mutation in nucleic acid encoding a p53 polypeptide or nucleic acid regulating expression of the p53 polypeptide. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof. The histone deacetylase inhibitor can be panobinostat, trichostatin A, trapoxin B, phenylbutyrate, valproic acid, vorinostat, belinostat, LAQ824, entinostat, tacedinaline, mocetinostat, or any combinations thereof.

In another aspect, this document features methods for treating a mammal having endometrial cancer where the methods can include, or consist essentially of, (a) detecting (a-i) a mutation in nucleic acid encoding a FBW7 polypeptide or nucleic acid regulating expression of the FBW7 polypeptide, (a-ii) a mutation in nucleic acid encoding a PPP2R1A polypeptide or nucleic acid regulating expression of the PPP2R1A polypeptide, and (a-iii) an increased level of expression of nucleic acid encoding a CCNA2 polypeptide in a sample obtained from the mammal; (b) administering a platinum based cancer therapy to the mammal; and 9 10

(c) administering an AKT inhibitor to the mammal. The method also can include detecting (a-iv) a mutation in nucleic acid encoding a POLE polypeptide or nucleic acid regulating expression of the POLE polypeptide, and (a-v) a mutation in nucleic acid encoding a p53 polypeptide or nucleic acid regulating expression of the p53 polypeptide. The method also can include detecting (a-iv) a mutation in nucleic acid encoding a POLE polypeptide or nucleic acid regulating expression of the POLE polypeptide, and (a-v) an increased level of expression of nucleic acid encoding a E2F1 polypeptide in a sample from the mammal. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof. The AKT inhibitor can be GSK2141795, GSK2110183, GSK 690693, VQD-002, perifosine, miltefosine, MK-2206, AZD5363, ipatasertib, triciribine, or any combinations thereof.

In another aspect, this document features methods for treating endometrial cancer where the methods can include, or consist essentially of, administering a platinum based cancer therapy and an AKT inhibitor to a mammal identified as having (i) a mutation in nucleic acid encoding a FBW7 polypeptide or nucleic acid regulating expression of the FBW7 polypeptide, (ii) a mutation in nucleic acid encoding a PPP2R1A polypeptide or nucleic acid regulating expression of the PPP2R1A polypeptide, and (iii) an increased level of expression of nucleic acid encoding a CCNA2 polypeptide in a sample obtained from the mammal. The mammal also can be identified as having (iv) a mutation in nucleic acid encoding a POLE polypeptide or nucleic acid regulating expression of the POLE polypeptide, and (v) a mutation in nucleic acid encoding a p53 polypeptide or nucleic acid regulating expression of the p53 polypeptide. The mammal also can be identified as having (iv) a mutation in nucleic acid encoding a POLE polypeptide or nucleic acid regulating expression of the POLE polypeptide, and (v) an increased level of expression of nucleic acid encoding a E2F1 polypeptide in a sample from the mammal. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof. The AKT inhibitor can be GSK2141795, GSK2110183, GSK 690693, VQD-002, perifosine, miltefosine, MK-2206, AZD5363, ipatasertib, triciribine, or any combinations thereof.

In another aspect, this document features methods for treating a mammal having endometrial cancer where the methods can include, or consist essentially of, (a) detecting (a-i) a mutation in nucleic acid encoding a FBW7 polypeptide or nucleic acid regulating expression of the FBW7 polypeptide, (a-ii) a mutation in nucleic acid encoding a PPP2R1A polypeptide or nucleic acid regulating expression of the PPP2R1A polypeptide, and (a-iii) an increased level of expression of nucleic acid encoding a CIP2A polypeptide in a sample obtained from the mammal; (b) administering a platinum based cancer therapy to the mammal; and (c) administering an AKT inhibitor to the mammal. The method also can include detecting (a-iv) a mutation in nucleic acid encoding a POLE polypeptide or nucleic acid regulating expression of the POLE polypeptide, and (a-v) a mutation in nucleic acid encoding a p53 polypeptide or nucleic acid regulating expression of the p53 polypeptide. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof. The AKT inhibitor can include GSK2141795, GSK2110183, GSK 690693, VQD-002, perifosine, miltefosine, MK-2206, AZD5363, ipatasertib, triciribine, or any combinations thereof.

In another aspect, this document features methods for method for treating endometrial cancer where the methods can include, or consist essentially of, administering a platinum based cancer therapy and an AKT inhibitor to a mammal identified as having (i) a mutation in nucleic acid encoding a FBW7 polypeptide or nucleic acid regulating expression of the FBW7 polypeptide, (ii) a mutation in nucleic acid encoding a PPP2R1A polypeptide or nucleic acid regulating expression of the PPP2R1A polypeptide, and (iii) an increased level of expression of nucleic acid encoding a CIP2A polypeptide in a sample obtained from the mammal. The mammal also can be identified as having (iv) a mutation in nucleic acid encoding a POLE polypeptide or nucleic acid regulating expression of the POLE polypeptide, and (v) a mutation in nucleic acid encoding a p53 polypeptide or nucleic acid regulating expression of the p53 polypeptide. The mammal can be a human. The sample can include cancer cells of the endometrial cancer. The platinum based cancer therapy can be cisplatin, carboplatin, oxaliplatin, nedaplatin, triplatin tetranitrate, phenanthriplatin, picoplatin, satraplatin, or any combinations thereof. The AKT inhibitor can include GSK2141795, GSK2110183, GSK 690693, VQD-002, perifosine, miltefosine, MK-2206, AZD5363, ipatasertib, triciribine, or any combinations thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 1A-1C. FIG. 1A) Integrated schematic of the p53-p21-CDE/CHR and PIK3CA-AKT-FBW7 pathways in EC. FIG. 1B) Comparative analysis of the mRNA expression of oncogenes regulated directly or indirectly by the p53-p21-CDE/CHR pathway in p53 mutant (N=62) versus wild type EC (N=149) (excluding POLE mutants). FIG. 1C) Correlation coefficient analysis to delineate relationships between differentially expressed oncogenes in p53 mutated (N=62) and wild type (N=149) EC (excluding POLE mutants) as a function of mRNA expression of E2F1 and CCNA2 oncogenes.

FIGS. 2A-2D. FIG. 2A) Molecular classification differentiates four cohorts according to POLE mutations (POLE-mu), FBXW7 and/or PPP2R1A mutations (FBXW7-mu/PPP2R1A-mu), high CCNA2 expression (CCNA2-H) and low CCNA2 expression (CCNA2-L). FIG. 2B) Progression-free survival as a function of time according to molecular cohorts. FIG. 2C) Cox proportional model analysis of the molecular classification cohorts using CCNA2-L as the reference. FIG. 2D) Multivariate analysis including the configured panel cohorts, age, grade, histology, myometrial invasion, p53 status and stage.

FIGS. 3A-3D. FIG. 3A) Molecular classification differentiates four cohorts according to POLE mutations (POLE-mu), FBXW7 and/or PPP2R1A mutations (FBXW7-mu/PPP2R1A-mu), high CIP2A expression (CIP2A-H) and low CIP2A expression (CIP2A-L). FIG. 3B) Progression-free survival as a function of time according to molecular cohorts. FIG. 3C) Cox proportional model analysis of the molecular classification cohorts using CIP2A-L as the reference. FIG. 3D) Multivariate analysis including the configured panel cohorts, age, grade, histology, myometrial invasion, p53 status and stage.

FIGS. 4A-4D. FIG. 4A) Molecular classification differentiates four cohorts according to POLE mutations (POLE-mu), FBXW7 and/or PPP2R1A mutations (FBXW7-mu/PPP2R1A-mu), high CCNA2 and E2F1 expression (CCNA2-H/E2F1-H) and low CCNA2 and E2F1 expression (CCNA2-L/E2F1-L). FIG. 4B) Progression-free survival as a function of time according to molecular cohorts. FIG. 4C) Cox proportional model analysis of the molecular classification cohorts using CCNA2-L/E2F1-L as the reference. FIG. 4D) Multivariate analysis including the configured panel, age, grade, histology, myometrial invasion, p53 status and stage.

FIGS. 9A-9D. FIG. 9A) Endometrial cancer (N=239) stratified according to specimens having POLE mutations, P53 mutations, CCNA2 high expression and/or FBXW7 mutations and/or PPP2R1A mutations, and CCNA2 low expression and wild type FBXW7 and PPP2R1A. P53 mutants were incorporated within the CCNA2 high/FBXW7 mu/PPP2R1A-mu or the CCNA2 low/FBXW7-wt/PPP2R1A-wt cohorts. The percent of patients with recurrence per subgroup is noted in parenthesis. FIG. 9B) Progression-free survival (PFS) by group. FIG. 9C) Cox proportional model analysis of the molecular classification cohorts using CCNA2-L, PPP2R1A-wt, and FBXW7-wt as the reference. FIG. 9D) Multivariate analysis including the configured panel cohorts, age, grade, histology, myometrial invasion, and stage.

FIGS. 10A-10D. FIG. 10A) Endometrial cancer (N=239) stratified according to specimens having POLE mutations, P53 mutations, CIP2A high expression and/or FBXW7 mutations and/or PPP2R1A mutations, and CIP2A low expression and wild type FBXW7 and PPP2R1A. P53 mutants were incorporated within the CIP2A high/FBXW7-mu/PPP2R1A-mu or the CIP2A low/FXW7-wt/PPP2R1A-wt cohorts. The percent of patients with recurrence per subgroup is noted in parenthesis. FIG. 10B) PFS by group. FIG. 10C) Cox proportional model analysis of the molecular classification cohorts to using CIP2A-L, PPP2R1A-wt, and FBXW7-wt as the reference. FIG. 10D) Multivariate analysis including the configured panel cohorts, age, grade, histology, myometrial invasion, and stage.

FIGS. 13A-13F. Molecular Profile and Clinical Outcomes. FIG. 13A) Integrated schematic of the CCNA2-E2F1-CIP2A axis and PI3K-AKT-GSK3β-FBW7 pathway. FIG. 13B) ECPPF classification differentiates molecular distinct subgroups among 192 cases with endometrioid endometrial cancer: POLE mutants (-mu), PPP2R1A-mu, FBXW7-mu, CCNA2-H/E2F1-H, and CCNA2-L/E2F1-L; latter 2 stratified per TP53-mu and TP53-wt (wild type). FIG. 13C) Progression-free survival (PFS) as a function of time according to 4 primary ECPPF molecular cohorts. FIG. 13D) PFS as a function of time according to ECPPF molecular cohorts with CCNA2-H/E2F1-H and CCNA2-L/E2F1-L stratified per TP53-mu and TP-wt. FIG. 13E) Cox proportional hazards model with hazard ratios (HR) for 6 stratified molecular cohorts with CCNA2-L/E2F1-L as the reference. FIG. 13F) Multivariate analysis including age, grade, myometrial invasion, stage, mutant TP53, PIK3CA, PTEN, PIK3R1, KRAS, ARID1A, CTNNB1, BRAC1, BRCA2, BRIP1, EXO1, and Rad51, CIP2A expression and ECPPF panel.

FIG. 14A) Excluding POLE-mu cases, distribution of recurrences, stage, myometrial invasion >50%, TP-mu, mutant homologous recombination genes (HR-mu), and high microsatellite instability (MSI-H) illustrated according to increasing quantitative sum of CCNA2 and E2F1 log$_2$ mRNA expression (CA2+E2F) as depicted in the heatmap; CIP2A, FOXM1, SKP 2, PARP1, and HR and cell cycle gene mRNA expression illustrated as a function of increasing expression of CA2+E2F. FIG. 14B) Accruing treatment failures as a function of the expression sum of CCNA2 and E2F1 (CA2+E2F).

FIG. 15A) Progression-free survival (PFS) among 85 stage I, grade (G) 1/2, ≤50% myometrial invasion (MI) cases according to ECPPF molecular low-risk [MLR (N=56); CA2+E2F≤4.75, PPP2R1A wild type (wt) and FBXW7-wt] and molecular high-risk [MHR (N=29); CA2+E2F≥4.75 and/or PPP2R1A mutant (mu) and/or FBXW7-mu]. FIG. 15B) PFS amid 122 stage I/II, G1/2<75% MI and G3<50% MI cases stratified according to ECPPF risk cohorts CA2+E2F<4.75 (N=75), CA2+E2F≥4.75 (N=29) and PPP2R1A-mu/FBXW7-mu (N=18). FIG. 15C) PFS among 28 stage I, G 1/2, ≤50% MI harboring CTNNB1-mu stratified according to ECPPF MLR (N=19) and MHR (N=9). FIG. 15D) PFS among 42 stages III/IV and stages I/II, G2>75% MI, and G3>50% MI stratified according ECPPF MLR (N=22) and MHR (N=20). FIG. 15E) PFS among 30 stage III/IV cases stratified according to ECPPF MLR (N=16) and MHR (N=14).

FIG. 16A) Excluding POL-Emu cases, 34 (of the commonest) HRmu detected among 164 endometrioid endometrial cancers. FIG. 16B) Prevalence of HRmu according to stage, NSMP (no specific molecular profile), TP53mu, MI (myometrial invasion), MSI [microsatellite instability high (H), low (L)], grade and ECPPF. FIG. 16C) Progression-free survival (PFS) among 34 HRmu cases stratified according to traditional low-risk [stage I grade (G) 1/2 (N=16)] and high-risk [stages I G3, II, III and IV (N=18)]. FIG. 16D) PFS among 34 HRmu cases stratified according to stage and ECPPF molecular low and high risk (MLR and MHR, respectively).

DETAILED DESCRIPTION

Figures 2A, 2B:
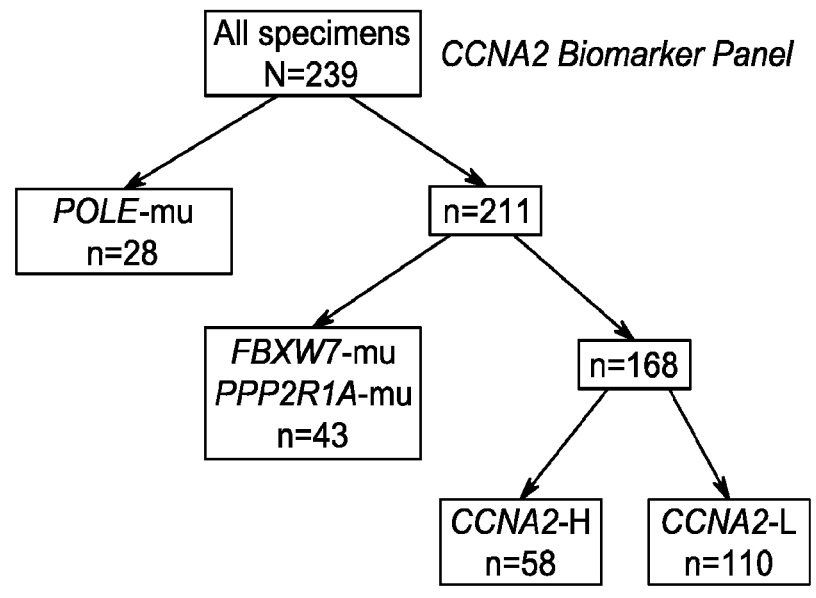

This document provides methods and materials involved in assessing and/or treating mammals (e.g., humans) having endometrial cancer. In some cases, the methods and materials provided herein can be used to determine whether or not a mammal having endometrial cancer is likely to respond to a particular cancer treatment (e.g., a platinum based cancer therapy). For example, a sample (e.g., a sample containing one or more cancer cells) obtained from a mammal having endometrial cancer can be assessed for the presence or absence of one or more mutations in one or more nucleic acids to determine whether or not the mammal is likely to respond to a platinum based cancer therapy. In some cases, a sample (e.g., a sample containing one or more cancer cells) obtained from a mammal having endometrial cancer can be assessed for the presence or absence of increased level of expression of one or more nucleic acids encoding a polypeptide to determine whether or not the mammal is likely to respond to a platinum based cancer therapy. In some cases, the methods and materials provided herein also can include administering one or more cancer treatments to a mammal having endometrial cancer to treat the mammal (e.g., one or more cancer treatments selected based, at least in part, on whether or not the mammal is likely to respond to a particular cancer treatment such as a platinum based cancer therapy).

A mammal (e.g., a human) having endometrial cancer can be assessed to determine whether or not the cancer is likely to respond to a particular cancer treatment (e.g., a platinum based cancer therapy) by detecting the presence or absence of one or more mutations in one or more nucleic acids and/or the presence or absence of increased level of expression of one or more nucleic acids encoding a polypeptide in a sample (e.g., a sample containing one or more cancer cells) obtained from the mammal. As described herein, the presence of one or more mutations in one or more nucleic acids and the presence of increased level of expression of one or more nucleic acids encoding a polypeptide in a sample obtained from the mammal can be used to determine whether or not that mammal is likely to respond to a particular cancer treatment (e.g., a platinum based cancer therapy).

Any appropriate mammal having endometrial cancer can be assessed and/or treated as described herein. Examples of mammals that can have endometrial cancer and can be assessed and/or treated as described herein include, without limitation, humans, non-human primates (e.g., monkeys), dogs, cats, horses, cows, pigs, sheep, mice, and rats. In some cases, a mammal can be a female mammal. In some cases, a mammal can have a disease or condition that increases the amount of estrogen (e.g., but not the level of progesterone) in the body such as polycystic ovary syndrome, obesity, and diabetes. In some cases, a mammal can have an ovarian tumor (e.g., an ovarian tumor that secretes estrogen). In some cases, a mammal can have taken or can be taking one or more hormone therapies (e.g., a hormone therapy for breast cancer such as tamoxifen). In some cases, a mammal can have a colon cancer syndrome (e.g., hereditary nonpolyposis colorectal cancer (HNPCC)). For example, a female human having endometrial cancer can be assessed and/or treated as described herein.

When assessing and/or treating a mammal (e.g., a human) having endometrial cancer as described herein, the endometrial cancer can be any type of endometrial cancer. An endometrial cancer can be any stage of endometrial cancer (e.g., stage I, stage II, stage III, or stage IV). An endometrial cancer can be any grade of endometrial cancer (e.g., grade 1, grade 2, or grade 3). In some cases, an endometrial cancer can be a primary cancer (e.g., a localized primary cancer). In some cases, an endometrial cancer can have metastasized.

In some cases, the methods described herein can include identifying a mammal (e.g., a human) as having endometrial cancer. Any appropriate method can be used to identify a mammal as having endometrial cancer. For example, physical examination (e.g., a pelvic examination), imaging techniques (e.g., transvaginal ultrasound, hysteroscopy, X-ray, computerized tomography (CT) scanning, and positron emission tomography (PET) scanning), sampling the vaginal fluid pool, and biopsy techniques can be used to identify a mammal (e.g., a human) as having endometrial cancer.

In some cases, a mammal (e.g., a human) having endometrial cancer can be identified as likely to respond to a particular cancer treatment (e.g., a platinum based cancer therapy) based, at least in part, on the presence or absence of one or more (e.g., one, two, three, four, five, or more) mutations in one or more (e.g., one, two, three, four, five, or more) nucleic acids in a sample (e.g., a sample containing one or more cancer cells) obtained from the mammal. The term "mutation" as used herein with respect to nucleic acid refers to a modification in the nucleic acid sequence as compared to a wild type nucleic acid for a particular species. A mutation can be any type of mutation including, without limitation, an insertion of one or more nucleotides, a deletion of one or more nucleotides, an insertion of one or more nucleotides in combination with a deletion of one or more nucleotides (an INDEL), a substitution of one or more nucleotides, and combinations thereof. A mutation can be in a coding or a non-coding region (e.g., exons, introns, untranslated sequences, sequences upstream of the transcription start site of a mRNA, sequences downstream of the transcription termination site of a mRNA, and sequences regulating expression of a polypeptide). In some cases, a mutation in a nucleic acid can cause altered (e.g., increased or decreased) polypeptide expression. In some cases, a mutation in a nucleic acid can result in premature termination of the coding sequence through the introduction of a stop codon within the coding frame. In some cases, a mutation can be a frame-shift mutation. A nucleic acid that can include one or more mutations can be any appropriate nucleic acid. Examples of nucleic acids that can include one or more mutations in a sample from a mammal having endometrial cancer include, without limitation, a POLE nucleic acid (e.g., nucleic acid encoding a POLE polypeptide), a p53 nucleic acid (e.g., nucleic acid encoding a p53 polypeptide), a FBXW7 nucleic acid (e.g., nucleic acid encoding a FBW7 polypeptide), a PPP2R1A nucleic acid (e.g., nucleic acid encoding a PPP2R1A polypeptide), PTEN nucleic acid (e.g., nucleic acid encoding a PTEN polypeptide), PIK3CA nucleic acid (e.g., nucleic acid encoding a PIK3CA polypeptide), PIK3R1 nucleic acid (e.g., nucleic acid encoding a PIK3R1 polypeptide), KRAS nucleic acid (e.g., nucleic acid encoding a KRAS polypeptide), ARID1A nucleic acid (e.g., nucleic acid encoding a ARID1A polypeptide), and CTNNB1 nucleic acid (e.g., nucleic acid encoding a CTNNB1 polypeptide). In some cases, a mutation in a POLE nucleic acid can be in exon 9 of a POLE nucleic acid. In some cases, a mutation in a POLE nucleic acid can be as described elsewhere (see, e.g., Li et al., BMC Med Genetics 20:202 (2019)). In some cases, a mutation in ap53 nucleic acid can be a hot spot mutation. Examples of mutations in ap53 nucleic acid include, without limitation, R175, G245, R248, R249, R273, and R282. In some cases, a mutation in ap53 nucleic acid can be as described elsewhere (see, e.g., Saha et al., *Prog Biophys Mol Biol* 117(2-3):250 (2015)). In some cases, a mutation in a FBXW7 nucleic acid can be a hot spot mutation. Examples of mutations in a FBXW7 nucleic acid include, without limitation, R505, R465, R479, R278, R367, G423, and 5582. In some cases, a mutation in a FBXW7 nucleic acid can be as described elsewhere (see, e.g., Yeh et al., *Mol Cancer* 17:115 (2018)). In some cases, a mutation in a PPP2R1A nucleic acid can be a hot spot mutation. Examples of mutations in a PPP2R1A nucleic acid include, without limitation, P179, R183, and 5256. In some cases, a mutation in a PPP2R1A nucleic acid can be as described elsewhere (see, e.g., Taylor et al., *Cancer Res* 79(16):4242 (2019)). In some cases, a mutation in a nucleic acid sequence in a sample from a mammal having endometrial cancer can be as described in Example 1.

Any appropriate method can be used to detect the presence or absence of one or more mutations in a nucleic acid within a sample (e.g., a sample containing one or more cancer cells) obtained from a mammal (e.g., a human). For example, sequencing (e.g., PCR-based sequencing), DNA hybridization, restriction enzyme digestion methods, heteroduplex analysis, denaturing gradient gel electrophoresis, DNA microarray technology, single strand conformational polymorphism, allele specific oligonucleotides, and protein truncation test can be used to identify the presence or absence of one or more mutations in a nucleic acid. In some cases, the presence or absence of one or more mutations a nucleic acid within a sample from a mammal having endometrial cancer can be determined as described in Example 1.

In some cases, a mammal (e.g., a human) having endometrial cancer can be identified as likely to respond to a particular cancer treatment (e.g., a platinum based cancer therapy) based, at least in part, on the presence of increased level of expression of one or more (e.g., one, two, three, four, five, or more) nucleic acids encoding a polypeptide in a sample (e.g., a sample containing one or more cancer cells) obtained from the mammal. The term "increased level" as used herein with respect to a level of expression of a nucleic acid encoding a polypeptide refers to any level that is greater than a reference level of expression of that nucleic acid. The term "reference level" as used herein with respect to expression of a nucleic acid refers to the level of expression of that nucleic acid typically observed in a sample (e.g., a control sample) from one or more comparable mammals (e.g., humans of comparable age) that do not have endometrial cancer. Control samples can include, without limitation, comparable samples from mammals that do not have endometrial cancer. Examples of nucleic acids that can have increased levels of expression in a sample from a mammal having endometrial cancer include, without limitation, CCNA2 nucleic acid (e.g., nucleic acid encoding a CCNA2 polypeptide), CIP2A nucleic acid (e.g., nucleic acid encoding a CIP2A (KIAA1524) polypeptide), E2F1 nucleic acid (e.g., nucleic acid encoding a E2F1 polypeptide), FOXM1 nucleic acid (e.g., nucleic acid encoding a FOXM1 polypeptide), EXO1 nucleic acid (e.g., nucleic acid encoding a EXO1 polypeptide), BRIP1 nucleic acid (e.g., nucleic acid encoding a BRIP1 polypeptide), Rad51 nucleic acid (e.g., nucleic acid encoding a Rad51 polypeptide), and BRCA2 nucleic acid (e.g., nucleic acid encoding a BRCA2 polypeptide). In some cases, an increased level of expression of one or more nucleic acids encoding a polypeptide can be a level that is at least 2 (e.g., at least 5, at least 10, at least 15, at least 20, or at least 25) fold greater relative to a reference level of expression of that nucleic acid. In some cases, when control samples have an undetectable level of expression of a nucleic acid, an increased level can be any detectable level of expression of that nucleic acid. It will be appreciated that levels from comparable samples are used when determining whether or not a particular level is an increased level. In some cases, a nucleic acid having an increased level of expression in a sample from a mammal having endometrial cancer can be as set forth in Table 2 and/or Table 3. In some cases, a nucleic acid having an increased level of expression in a sample from a mammal having endometrial cancer can be as described in Example 1.

Any appropriate method can be used to detect the presence or absence of an increased level of expression of one or more nucleic acids encoding a polypeptide within a sample (e.g., a sample containing one or more cancer cells) obtained from a mammal (e.g., a human). In some cases, a level of expression of one or more nucleic acids encoding a polypeptide within a sample can be determined by detecting the presence, absence, or level of the polypeptide in the sample. For example, immunoassays (e.g., immunohistochemistry (IHC) techniques and western blotting techniques), mass spectrometry techniques (e.g., proteomics-based mass spectrometry assays or targeted quantification-based mass spectrometry assays), enzyme-linked immunosorbent assays (ELISAs), and radio-immunoassays can be used to determine the presence, absence, or level of a polypeptide in a sample. In some cases, a level of expression of one or more nucleic acids encoding a polypeptide within a sample can be determined by detecting the presence, absence, or level of mRNA encoding the polypeptide in the sample. For example, polymerase chain reaction (PCR)-based techniques such as quantitative RT-PCR techniques, gene expression panel (e.g., next generation sequencing (NGS) such as RNA-seq), in situ hybridization, and Nanostring technology can be used to determine the presence, absence, or level of mRNA encoding the polypeptide in the sample. In some cases, the presence or absence of an increased level of expression of one or more nucleic acids encoding a polypeptide within a sample from a mammal having endometrial cancer can be determined as described in Example 1.

In some cases, a mammal (e.g., a human) having endometrial cancer can be identified as not being likely to respond to a particular cancer treatment (e.g., a platinum based cancer therapy) based, at least in part, on the presence of one or more mutations in a FBXW7 nucleic acid, the presence of one or more mutations in a PPP2R1A nucleic acid, and the presence of an increased level of expression of nucleic acid encoding a CCNA2 polypeptide in a sample (e.g., a sample containing one or more cancer cells) obtained from the mammal. For example, a mammal having endometrial cancer can be identified as not being likely to respond to a platinum based cancer therapy based, at least in part, on the presence of one or more mutations in a p53 nucleic acid, the presence of one or more mutations in a FBXW7 nucleic acid, the presence of one or more mutations in a PPP2R1A nucleic acid, and the presence of an increased level of expression of nucleic acid a CCNA2 polypeptide in a sample obtained from the mammal. In some cases, a mammal having endometrial cancer can be identified as being not likely to respond to a platinum based cancer therapy based, at least in part, on the presence of one or more mutations in a FBXW7 nucleic acid, the presence of one or more mutations in a PPP2R1A nucleic acid, the presence of an increased level of expression of nucleic acid encoding a CCNA2 polypeptide, and the presence of an increased level of expression of nucleic acid encoding a E2F1 polypeptide in a sample obtained from the mammal.

In some cases, a mammal (e.g., a human) having endometrial cancer can be identified as not being likely to respond to a particular cancer treatment (e.g., a platinum based cancer therapy) based, at least in part, on the presence of one or more mutations in a FBXW7 nucleic acid, the presence of one or more mutations in a PPP2R1A nucleic acid, and the presence of an increased level of expression of nucleic acid encoding a CIP2A polypeptide in a sample (e.g., a sample containing one or more cancer cells) obtained from the mammal. For example, a mammal having endometrial cancer can be identified as not being likely to respond to respond to a platinum based cancer therapy based, at least in part, on the presence of one or more mutations in a p53 nucleic acid, the presence of one or more mutations in a FBXW7 nucleic acid, the presence of one or more mutations in a PPP2R1A nucleic acid, and the presence of an increased level of expression of nucleic acid encoding a CIP2A polypeptide in a sample obtained from the mammal.

Any appropriate sample from a mammal (e.g., a human) having endometrial cancer can be assessed as described herein (e.g., for the presence or absence of one or more mutations in one or more nucleic acids and/or the presence or absence of an increased level of expression of one or more nucleic acids encoding a polypeptide). In some cases, a sample can be a biological sample. In some cases, a sample can contain one or more cancer cells. In some cases, a sample can contain one or more biological molecules (e.g., nucleic acids such as DNA and RNA, polypeptides, carbohydrates, lipids, hormones, and/or metabolites). Examples of samples that can be assessed as described herein include, without limitation, tissue samples (e.g., uterine tissue samples, endometrial biopsy samples), fluid samples (e.g., whole blood, serum, plasma, urine, vaginal pool, and saliva), and cellular samples (e.g., Pap smear samples and Tao brush samples). A sample can be a fresh sample or a fixed sample (e.g., a formaldehyde-fixed sample or a formalin-fixed sample). In some cases, a sample can be a processed sample (e.g., an embedded sample such as a paraffin or OCT embedded sample). In some cases, one or more biological molecules can be isolated from a sample. For example, nucleic acid (e.g., DNA and RNA such as messenger RNA (mRNA)) can be isolated from a sample and can be assessed as described herein. For example, one or more polypeptides can be isolated from a sample and can be assessed as described herein.

In some cases, a mammal (e.g., a human) having endometrial cancer and assessed as described herein (e.g., to determine whether or not the cancer is likely to respond to a particular cancer treatment based, at least in part, on the presence or absence of one or more mutations in one or more nucleic acids and/or the presence or absence of an increased level of expression of one or more nucleic acids encoding a polypeptide) can be administered or instructed to self-administer one or more (e.g., one, two, three, four, five, or more) cancer treatments, where the one or more cancer treatments are effective to treat the cancer within the mammal. For example, a mammal having endometrial cancer can be administered or instructed to self-administer one or more cancer treatments selected based, at least in part, on whether or not the mammal is likely to respond to a platinum based cancer therapy (e.g., based, at least in part, on the presence or absence of one or more mutations in a nucleic acid and/or the presence or absence of an increased level of expression of one or more nucleic acids encoding a polypeptide). A cancer treatment can include any appropriate cancer treatment. In some cases, a cancer treatment can include administering one or more cancer drugs (e.g., chemotherapeutic agents, targeted cancer drugs, immunotherapy drugs, and hormones) to a mammal in need thereof. Examples of cancer drugs that can be administered to a mammal having endometrial cancer can include, without limitation, cisplatin, carboplatin, oxaliplatin, nedaplatin, triplatin tetranitrate, phenanthriplatin, picoplatin, satraplatin, panobinostat, trichostatin A, trapoxin B, phenylbutyrate, valproic acid, vorinostat, belinostat, LAQ824, entinostat, tacedinaline, mocetinostat, GSK2141795, GSK2110183, VQD-002, perifosine, miltefosine, MK-2206, AZD5363, ipatasertib, pembrolizumab (e.g., KEYTRUDA®), lenvatinib mesylate (e.g., LENVIMA®), paclitaxel, megestrol acetate, progesterone therapy (e.g., cyclic or continuous progestin therapy), one or more compounds that can increase p21 polypeptide expression and/or p21 polypeptide activity, one or more compounds that can inhibit CCNA2 polypeptide expression and/or CCNA2 polypeptide activity, one or more compounds that can inhibit E2F1 polypeptide expression and/or E2F1 polypeptide activity, one or more compounds that can inhibit CIP2A polypeptide expression and/or CIP2A polypeptide activity, one or more compounds that can increase PP2A polypeptide expression and/or PP2A polypeptide activity, one or more compounds that can inhibit AKT polypeptide expression and/or AKT polypeptide activity, one or more compounds that can inhibit Rad 51 polypeptide expression and/or Rad51 polypeptide activity, one or more compounds that can inhibit EXO1 expression and/or EXO1 activity, and combinations thereof. In some cases, a cancer treatment can include surgery. Examples of surgeries that can be performed on a mammal having endometrial cancer to treat the mammal include, without limitation, hysterectomy (removal of the uterus), salpingo-oophorectomy (removal of the uterus, fallopian tubes, and ovaries), regional sentinel lymph node sampling, lymphadenectomy, and cytoreduction for stage IV disease. In some cases, a cancer treatment can include radiation treatment. For example, a cancer treatment can include radiation treatment and administering one or more cancer drugs where the radiation treatment is administered before and/or after administering one or more cancer drugs.

When treating a mammal (e.g., a human) having endometrial cancer and identified as not being likely to respond to one or more platinum based cancer therapies as described herein (e.g., based, at least in part, on the presence of one or more mutations in a nucleic acid and/or the presence of an increased level of expression of one or more nucleic acids encoding a polypeptide), the mammal can be administered or instructed to self-administer one or more (e.g., one, two, three, four, five, or more) alternative cancer treatments (e.g., one or more cancer treatments that are not a platinum based cancer therapy). For example, a mammal having cancer and identified as having the presence of one or more mutations in a FBXW7 nucleic acid, having the presence of one or more mutations in a PPP2R1A nucleic acid, and having the presence of an increased level of expression of nucleic acid encoding a CCNA2 polypeptide in a sample (e.g., a sample containing one or more cancer cells) obtained from the mammal can be administered or instructed to self-administer one or more alternative cancer treatments that are not platinum based cancer therapies. For example, a mammal having cancer and identified as having the presence of one or more mutations in a FBXW7 nucleic acid, having the presence of one or more mutations in a PPP2R1A nucleic acid, and having the presence of an increased level of expression of nucleic acid encoding a CIP2A polypeptide in a sample (e.g., a sample containing one or more cancer cells) obtained from the mammal can be administered or instructed to self-administer one or more alternative cancer treatments that are not platinum based cancer therapies. Examples of alternative cancer treatments that are not a platinum based cancer therapy include, without limitation, administering one or more cancer drugs (e.g., chemotherapeutic agents, targeted cancer drugs, immunotherapy drugs, and hormones) other than a platinum based cancer therapy to a mammal in need thereof. Examples of cancer drugs that are not a platinum based cancer therapy and that can be administered to a mammal having endometrial cancer and identified as not being likely to respond to a platinum based cancer therapy can include, without limitation, panobinostat, trichostatin A, trapoxin B, phenylbutyrate, valproic acid, vorinostat, belinostat, LAQ824, entinostat, tacedinaline, mocetinostat, GSK2141795, GSK2110183, VQD-002, perifosine, miltefosine, MK-2206, AZD5363, ipatasertib, pembrolizumab (e.g., KEYTRUDA®), lenvatinib mesylate (e.g., LENVIMA®), megestrol acetate, progesterone therapy (e.g., cyclic or continuous progestin therapy), compounds that can increase p21 polypeptide expression and/or p21 polypeptide activity, compounds that can inhibit CCNA2 polypeptide expression and/or CCNA2 polypeptide activity, compounds that can inhibit E2F1 polypeptide expression and/or E2F1 polypeptide activity, compounds that can inhibit CIP2A polypeptide expression and/or CIP2A polypeptide activity, compounds that can increase PP2A polypeptide expression and/or PP2A polypeptide activity, one or more compounds that can inhibit AKT polypeptide expression and/or AKT polypeptide activity, one or more compounds that can inhibit Rad 51 polypeptide expression and/or Rad51 polypeptide activity, one or more compounds that can inhibit EXO1 expression and/or EXO1 activity, and combinations thereof. In some cases, an alternative cancer drug can be a HDACi. Examples of HDACis include, without limitation, panobinostat, trichostatin A, trapoxin B, phenylbutyrate, valproic acid, vorinostat, belinostat, LAQ824, entinostat, tacedinaline, and mocetinostat. In some cases, an alternative cancer drug can be an AKT inhibitor. Examples of AKT inhibitors include, without limitation, GSK2141795, GSK2110183, GSK 690693, VQD-002, perifosine, miltefosine, MK-2206, AZD5363, ipatasertib, and triciribine. In some cases, an alternative cancer treatment can include surgery. Examples of surgeries that can be performed on a mammal having endometrial cancer include, without limitation, hysterectomy (removal of the uterus), salpingo-oophorectomy (removal of the uterus, fallopian tubes, and ovaries), regional sentinel lymph node sampling, lymphadenectomy, and cytoreduction for stage IV disease. In some cases, an alternative cancer treatment can include radiation treatment. For example, an alternative cancer treatment can include radiation treatment and administering one or more cancer drugs where the radiation treatment is administered before and/or after administering one or more cancer drugs.

When treating a mammal (e.g., a human) having endometrial cancer and identified as not being likely to respond to one or more platinum based cancer therapies as described herein (e.g., based, at least in part, on the presence of one or more mutations in a nucleic acid and/or the presence of an increased level of expression of one or more nucleic acids encoding a polyp eptide), the mammal can be administered or instructed to self-administer (a) one or more (e.g., one, two, three, four, five, or more) platinum based cancer therapies and (b) one or more (e.g., one, two, three, four, five, or more) alternative cancer drugs (e.g., one or more cancer drugs that are not a platinum based cancer therapy). For example, a mammal having endometrial cancer and identified as not being likely to respond to one or more platinum based cancer therapies as described herein can be administered a platinum based cancer therapy (e.g., carboplatin) and also can be administered one or more HDACi (e.g., panobinostat). For example, a mammal having endometrial cancer and identified as not being likely to respond to one or more platinum based cancer therapies as described herein can be administered a platinum based cancer therapy (e.g., carboplatin) and also can be administered one or more AKT inhibitors (e.g., GSK2141795). In some cases, the one or more platinum based cancer therapies can be administered together with the one or more alternative cancer treatments (e.g., in a composition containing one or more platinum based cancer therapies and containing one or more alternative cancer drugs that are not a platinum based cancer therapy). In some cases, the one or more platinum based cancer therapies can be administered independent of the one or more alternative cancer drugs. When the one or more platinum based cancer therapies are administered independent of the one or more alternative cancer drugs, the one or more alternative cancer drugs can be administered first, and the one or more platinum based cancer therapies administered second, or vice versa.

When treating a mammal (e.g., a human) having endometrial cancer and identified as being likely to respond to one or more platinum based cancer therapies as described herein (e.g., based, at least in part, on the absence of one or more mutations in a nucleic acid and/or the absence of an increased level of expression of one or more nucleic acids encoding a polypeptide), the mammal can be administered or instructed to self-administer one or more (e.g., one, two, three, four, five, or more) platinum based cancer therapies. For example, a mammal having cancer and identified as lacking one or more mutations in a FBXW7 nucleic acid sequence, lacking one or more mutations in a PPP2R1A nucleic acid, and lacking an increased level of expression of nucleic acid encoding a CCNA2 polypeptide in a sample (e.g., a sample containing one or more cancer cells) obtained from the mammal can be administered or instructed to self-administer one or more platinum based cancer therapies. For example, a mammal having cancer and identified as lacking one or more mutations in a FBXW7 nucleic acid, lacking one or more mutations in a PPP2R1A nucleic acid, and lacking an increased level of expression of nucleic acid encoding a CIP2A polypeptide in a sample (e.g., a sample containing one or more cancer cells) obtained from the mammal can be administered or instructed to self-administer one or more platinum based cancer therapies. Examples of platinum based cancer therapy include, without limitation, cisplatin, carboplatin, oxaliplatin, nedaplatin, triplatin tetranitrate, phenanthriplatin, picoplatin, and satraplatin.

In some cases, when treating a mammal (e.g., a human) having endometrial cancer as described herein, the treatment can be effective to treat the cancer. For example, the number of cancer cells present within a mammal can be reduced using the materials and methods described herein. In some cases, the size (e.g., volume) of one or more tumors present within a mammal can be reduced using the materials and methods described herein. For example, the materials and methods described herein can be used to reduce the size of one or more tumors present within a mammal having endometrial cancer by, for example, 10, 20, 30, 40, 50, 60, 70, 80, 90, 95, or more percent. In some cases, the size (e.g., volume) of one or more tumors present within a mammal does not increase.

In some cases, when treating a mammal (e.g., a human) having endometrial cancer as described herein, the treatment can be effective to improve survival of the mammal. For example, the methods and materials described herein can be used to improve disease-free survival (e.g., relapse-free survival). For example, the methods and materials described herein can be used to improve progression-free survival. For example, the materials and methods described herein can be used to improve the survival of a mammal having endometrial cancer by, for example, 10, 20, 30, 40, 50, 60, 70, 80, 90, 95, or more percent. For example, the materials and methods described herein can be used to improve the survival of a mammal having endometrial cancer by, for example, at least 6 months (e.g., about 6 months, about 8 months, about 10 months, about 1 year, about 1.5 years, about 2 years, about 2.5 years, or about 3 years).

In some cases, when treating a mammal (e.g., a human) having endometrial cancer as described herein, the treatment can be effective to reduce one or more symptoms of the cancer. Examples of symptoms of endometrial cancer include, without limitation, vaginal bleeding (e.g., vaginal bleeding after menopause), bleeding between menstrual periods, pelvic pain, bladder dysfunction, ascites, gastrointestinal dysfunction, and lower extremity edema. For example, the materials and methods described herein can be used to reduce one or more symptoms within a mammal having endometrial cancer by, for example, 10, 20, 30, 40, 50, 60, 70, 80, 90, 95, or more percent.

The invention will be further described in the following examples, which do not limit the scope of the invention described in the claims.

EXAMPLES

Example 1: Novel Biomarker Panel for Endometrial Cancer Identifies Prognostic Risk, Platinum Insensitivity and Innovative Targeted Therapeutic Options Methods The Cancer Genome Atlas TCGA (cancergenome.nih.gov) data was obtained and analyzed as described elsewhere (see, e.g., Gonzalez et al., *Cancer Res.;* 74(14):3902-3912 (2014)). TCGA comprehensive genomic information includes copy number variation, single-nucleotide polymorphisms, miRNA expression, gene expression, and DNA methylation data, as well as clinical and outcome information. Data from TCGA were downloaded, normalized, formatted, and organized for integration and analysis with other biological datasets in accordance with TCGA data-sharing agreements. Somatic mutations and gene expression data were recorded.

Mutation Analysis

Somatic mutation detection, calling, annotation, and validation from TCGA were done as described elsewhere (see, e.g., Cancer Genome Atlas Research Network, *Nature;* 4 74(7353):609-615 (2011)). Somatic mutation information resulting from exome sequencing with the Illumina Genome Analyzer DNA Sequencing GAIIx or HiSeq 2000 platforms (Illumina Inc) was downloaded and formatted for analysis. Mutation information was downloaded as level 3 or validated somatic mutations.

Of the 239 EC tumors included in this study, 18,388 unique genes with 138,838 validated somatic mutations were identified, including frame-shift insertions and deletions, in-frame insertions or deletions, and missense, nonsense, nonstop, and splice-site mutations. Silent mutations were excluded from the analysis. The number of mutations for each selected gene was recorded for each patient.

Gene Expression

Gene expression data were downloaded from TCGA data repository as level 3 RNA sequence data created by Illumina RNA Sequencer HiSeq 2000 platforms (Illumina Inc) and annotated with the hg19 version of the human genome. Normalized and log-transformed gene expression data from these endometrial tumors were available for analysis. Analyses were performed with R statistical packages for statistical computing and graphics and Bioconductor packages as open-source software for bioinformatics. For the front end, Biometric Research Branch Array Tools, an integrated package for visualization and statistical analysis that uses Excel (Microsoft Corp), was used.

In Vitro Assessments

HEC-1B (Type I) and ARK-2 (Type II), platinum-insensitive EC cell lines, were used in this study. Both cell lines were cultured in DMEM (Dulbecco's Modified Eagle's Medium) media containing 10% FBS, 100 μg/mL streptomycin, 100 units/mL penicillin, and 2 mM L-glutamine. Cells were maintained in incubator at 37° C. in an atmosphere containing 5% $CO_2$.

Carboplatin, panobinostat (HDAC10 inhibitor), and GSK2141795 (AKT inhibitor) were all purchased from APExBio (Boston, USA).

Real-Time PCR

Total RNA was isolated using RNeasy® plus mini kit (Qiagen). cDNA was synthesized using Reverse Transcription kit (Applied Biosystems). Real-time PCR was performed using the Cyber Green Master Mix (Thermo) on LightCycler® 480 (Roche). The sequences of primers for the analyzed genes are detailed in Table 1.

TABLE 1

Real-time PCR primer
sequences for designated genes

| Gene | Forward sequence (5'-3') | SEQ ID | Reverse sequence (5'-3') | SEQ ID |
|------|--------------------------|--------|--------------------------|--------|
| P21 | TGTCACTGTCTTGTAC CCTTG | 1 | GGCGTTTGGAGTGGTA GAA | 2 |
| P53 | GCCATCTACAAGCAGT CACAG | 3 | TCATCCAAATACTCCA CACGC | 4 |
| CCNA2 | CTGCATTTGGCTGTGA ACTAC | 5 | ACAAACTCTGCTACTT CTGGG | 6 |
| CCNE1 | TCTTGAGCAACACCCT CTTC | 7 | TTCTTGTGTCGCCATA TACCG | 8 |
| E2F1 | TCTCCGAGGACACTGA CAG | 9 | ATCACCATAACCATCT GCTCTG | 10 |
| CIP2A | AGTCAGTACAAAGCCG TGAAG | 11 | ATAGTCGTGTGAGTTT CTGTCC | 12 |
| EXO1 | GCCATAATTACAGAGG ACTCGG | 13 | TTCCGTGAATACATCC CCAAG | 14 |
| FOXM1 | ACCGCTACTTGACATT GGAC | 15 | GGGAGTTCGGTTTTGA TGGTC | 16 |
| GAPDH | ACATCGCTCAGACACC ATG | 17 | TGTAGTTGAGGTCAAT GAAGGG | 18 |

MTT Assay and Synergy Assessment

Three thousand cells/well were seeded in triplicate in 96-well plates and cells were treated with increasing concentrations of panobinostat, GSK2141795, and carboplatin for 72 hours, respectively. CellTiter 96® Aqueous One Solution Cell Proliferation Assay was performed according to the manual to assess the half maximum inhibitory concentration (IC50). Constant ratio studies were carried out to investigate the combinatory effect of carboplatin with panobinostat and GSK2141795 in both HEC-1B and ARK-2 cell lines.

Statistical Analysis

For each candidate gene surveyed, the TCGA-quantitated expression levels of the corresponding mRNA were annotated for each of the 239 specimens. Comparisons between groups were evaluated with the $\chi^2$ test for nominal variables and the 2-sample t test for continuous variables. Correlations were quantified by using Pearson correlation coefficients. All calculated P values were 2 sided.

Progression Free Survival (PFS) Analysis

Statistical methods for survival data were used to analyze PFS, defined as the time from surgery to recurrence of disease. Patients with no evidence of disease at the end of their follow-up were treated as censored observations in the analysis. Comparisons between Kaplan-Meier survival curves were performed with the log-rank test. For association with survival, all clinical-pathological variables were assessed with Cox proportional hazard regression. All variables associated with survival with a univariate p-value≤0.05 were included in an initial multivariate regression model. Those variables with the smallest contribution effect to the model were excluded from the model, with a backward elimination technique based on AIC (Akaike Information Criterion: a measure of the quality of the model for a given dataset). Hazard-ratios were reported along with 95% confidence intervals (CI). Analyses were performed using R environment for statistical computing and graphics.

Results

Study Tumor Characteristics

Clinicopathologic characteristics in the study population (N=239) included 47 (26 stage 3/4) uterine serous carcinomas (USC) and 192 endometrioid EC (EEC) including 72 grade 1 (4 stage 3/4), 73 grade 2 (10 stage 3/4) and 47 grade 3 (16 stage 3/4). Molecular characteristics include POLE-mu detected in 28 specimens (11.7%), p53-mu in 70 (29.3%), microsatellite instability-high (MSI-H) in 67 (28%) and estimated copy number variation low (CNVL) determined via 239–(POLE-mu+p53-mu+MSI-H) in 92 (38.5%). P53-mu was identified in 41 (87.2%) USC and 29 (15.1%) EEC including 4.2% in grade 1, 12.3% in grade 2 and 36.5% in grade 3. At least one mutation in PIK3CA, PTEN or PIK3R1 occurred in 84% of the specimens; 59% had a mutation in more than one of these genes. Recognizing POLE-mu is associated with ultramutated status and superior outcomes (see, e.g., Cancer Genome Atlas Research Network, *Nature;* 497(7447):67-73 (2013)), POLE-mutants were not included in the subsequent molecular analyses except to use as a standard for comparing favorable outcomes. Thus, the study population consisted of 62 p53-mu and 149 p53-wt specimens.

Comparative Assessment of Oncogene Expression in p53-Mu and p53-Wt

To assess the validity of the proposed downstream network of p53-mu-dependent gene alterations in FIG. 1A, the mean mRNA expression level of the proposed gene network in p53-mu and p53-wt EC excluding POLE-mu specimens were compared. Assessment of CDKN1A (p21) expression in p53-mu compared to p53-wt EC demonstrates a differential consistent with the failure of mutant p53 to induce CDKN1A (p21) (FIG. 1B). Multiple genes harboring CDE/CHR p21 repressive site in their promoter regions including CDK2, CCNA2, AURKA, TPX2, PLK1, FOXM1, ESPL1 and MASTL are significantly up regulated in p53-mu compared to p53-wt EC. The lack of suppression of CDK2 and marked overexpression of CCNE1 and E2F1 portend the observed augmentation of multiple cell cycle (i.e., AURKA, TPX2, PLK1) and other genes (i.e., FOXM1, Rad 51, and CIP2A (KIAA1524)) harboring E2F1 transcriptional activating sites. By contrast, the E2F1 apoptotic target TP73 was suppressed in p53-mu tumors.

Oncogenes Expression Correlation with CCNA2 and E2F1

The correlation between reference oncogenes (E2F1 and CCNA2) and multiple direct or downstream targets of E2F1 in p53-mu and p53-wt EC was examined (FIG. 1C). Correlation coefficients for the reference genes in p53-mu tumors were similarly positive with regard to cell cycle genes but the positivity was substantially higher for CCNA2 than E2F1 for MASTL1, CIP2A and HR pathway genes. Unexpected was the high positive correlation observed in p53-wt EC between CCNA2 and all assessed direct and downstream E2F1 targets and HR pathway genes including the MRN complex (MRE11, Rad50 and NBS1). These observations suggested a potential role for CCNA2 in the carcinogenesis of p53-mu and a subset of p53-wt tumors.

Comparative Expression of Oncogenes as Function of p53-Mu and CCNA2 Expression

Figure 3A:
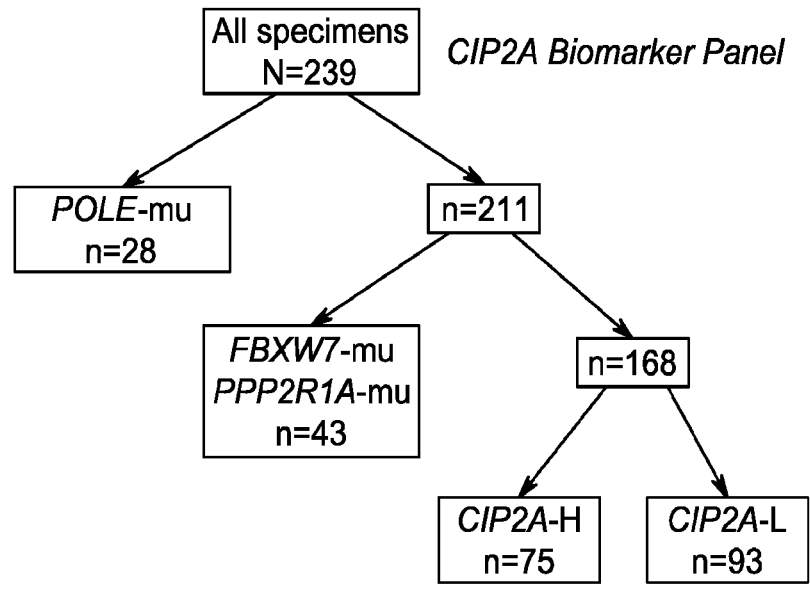

The expression of multiple upregulated oncogenes in p53-mu EC was assessed in p53-wt EC with high CCNA2 expression. The upper quartile of annotated CCNA2 mRNA expression levels among P53-wt specimens (≥2.60) was designated as "high" expression (CCNA2-H). Assessment of the expression of multiple CCNA2/E2F1 target and HR pathway genes in p53-wt CCNA2-H and p53-mu EC demonstrated equivalency or higher expression of the majority of assessed genes in p53-wt CCNA2-H compared to p53-mu specimens (Table 2). Also noted is the upregulation of FOXM1, CIP2A and multiple HR genes in both p53-mu and p53-wt CCNA2-H EC compared to p53-wt with low CCNA2 expression (CCNA2-L).

judged per Cox proportional HRs of 5.34 and 6.98 for CIP2A-H-mu and PPP2R1A-mu/FBXW7-mu, respectively (FIG. 3C). Moreover, adjusting for age, grade, histology, MI, p53 status and stage, independent significance was associated with CIP2A-H-mu (p=0.001), PPP2R1A-mu/FBXW7-mu (p=0.0003) and stage (p=0.0119) (FIG. 3D).

TABLE 2

Comparative assessment of the expression of multiple pathway-specific genes in p53 wild type/CCNA2-high versus p53 mutant versus p53 wild type/CCNA2-L specimens.

| Gene | Cohort A TP53 mutants Mean (SD) | Cohort B CCNA2-High Mean (SD) | Cohort C CCNA2-LOW Mean (SD) | Cohort A vs B Cohen's $d^\dagger$ | P | Cohort B vs C Cohen's $d^\dagger$ | P |
|---|---|---|---|---|---|---|---|
| | | P53-p21-CDK2-E2F1/CCNA2 pathway | | | | | |
| CDKN1A | 4.141 (1.257) | 5.648 (1.070) | 5.826 (1.080) | −1.271 | <0.001 | −0.165 | 0.37 |
| CDK2 | 3.627 (0.808) | 3.867 (0.529) | 2.811 (0.608) | −0.337 | 0.10 | 1.797 | <0.001 |
| E2F1 | 3.292 (1.006) | 2.703 (0.938) | 1.462 (0.868) | 0.602 | 0.004 | 1.398 | <0.001 |
| CCNA2 | 2.756 (0.894) | 3.276 (0.569) | 1.557 (0.793) | −0.665 | 0.001 | — | — |
| | | E2F1/CCNA2 targets | | | | | |
| CCNE1 | 4.207 (1.343) | 2.876 (1.085) | 2.084 (1.199) | 1.067 | <0.001 | 0.678 | <0.001 |
| AURKA | 3.253 (0.780) | 2.920 (0.738) | 1.621 (0.765) | 0.436 | 0.03 | 1.715 | <0.001 |
| TPX2 | 4.394 (0.808) | 4.117 (0.654) | 2.637 (0.791) | 0.369 | 0.07 | 1.957 | <0.001 |
| PLK1 | 4.402 (0.870) | 4.234 (0.811) | 2.877 (0.872) | 0.198 | 0.33 | 1.585 | <0.001 |
| FOXM1 | 4.103 (0.800) | 4.229 (0.653) | 2.801 (0.733) | −0.163 | 0.40 | 2.003 | <0.001 |
| EZH2 | 2.834 (0.711) | 2.898 (0.528) | 2.098 (0.620) | −0.098 | 0.63 | 1.340 | <0.001 |
| CIP2A | 2.245 (1.078) | 2.435 (0.690) | 0.835 (0.956) | −0.201 | 0.32 | 1.794 | <0.001 |
| | | Homologous recombination pathway genes | | | | | |
| MER11 | 0.975 (0.885) | 1.264 (0.537) | 0.624 (0.755) | −0.377 | 0.06 | 0.912 | <0.001 |
| RAD50 | 1.940 (0.753) | 2.461 (0.680) | 2.021 (0.603) | −0.719 | <0.001 | 0.704 | <0.001 |
| NBS1 | 2.473 (0.987) | 2.987 (0.644) | 2.340 (0.836) | −0.593 | 0.004 | 0.820 | <0.001 |
| BRCA1 | 1.168 (0.953) | 1.947 (0.744) | 0.778 (0.691) | −0.889 | <0.001 | 1.656 | <0.001 |
| BRIP1 | −0.354 (1.027) | 0.276 (0.805) | −1.151 (0.808) | −0.667 | 0.001 | 1.767 | <0.001 |
| EXO1 | 1.092 (0.919) | 1.509 (0.705) | 0.023 (1.027) | −0.496 | 0.02 | 1.563 | <0.001 |
| BRCA2 | −1.146 (1.355) | −0.395 (0.877) | −2.310 (1.200) | −0.631 | 0.002 | 1.708 | <0.001 |
| RAD51 | 1.782 (0.797) | 2.275 (0.679) | 0.829 (0.807) | −0.655 | 0.002 | 1.867 | <0.001 |

$^\dagger$Cohen's d = Absolute value of the difference in group means divided by the pooled standard deviation; higher the value the greater the difference between groups: ≥0.2/<0.5 small, ≥0.5/<0.8 medium and ≥0.8 large. Cohort A, N = 62; Cohort B, N = 41; Cohort C, N = 108

Clinical Outcomes According to EC Classifications

The molecular schematic suggested the high expression of FOXM1 observed with upregulated CCNA2 expression in p53-mu and p53-wt (FIG. 1A) combined with anticipated restricted proteosomal degradation of FOXM1 due to PPP2R1A-mu or FBXW7-mu would unfavorably impact survival. Accordingly, the study population was segregated into four cohorts including POLE-mu, PPP2R1A-mu/FBXW7-mu, CCNA2-H and CCNA2-L (FIG. 2A). PFS analysis for POLE mutants was as reported elsewhere (see, e.g., Cancer Genome Atlas Research Network, *Nature;* 497(7447):67-73 (2013)), but the CCNA2-H and PPP2R1A-mu/FBXW7-mu cohorts had substantially disparate outcomes compared to the CCNA2-L cohort (FIG. 2B). Cox proportional HR survival analysis using CCNA2-L as reference assigned significance for CCNA2-H (HR 3.68; p=0.0005) and PPP2R1A-mu/FBXW7-mu (HR 4.53; p=0.0002) (FIG. 2C). Adjusting for age, histology, grade, myometrial invasion (MI), p53 mutation status and stage, independent significance (PFS) was associated with CCNA2-H (p=0.0016), PPP2R1A-mu/FBXW7-mu (p=0.0007) and stage (p=0.0042) (FIG. 2D).

Figure 3B:
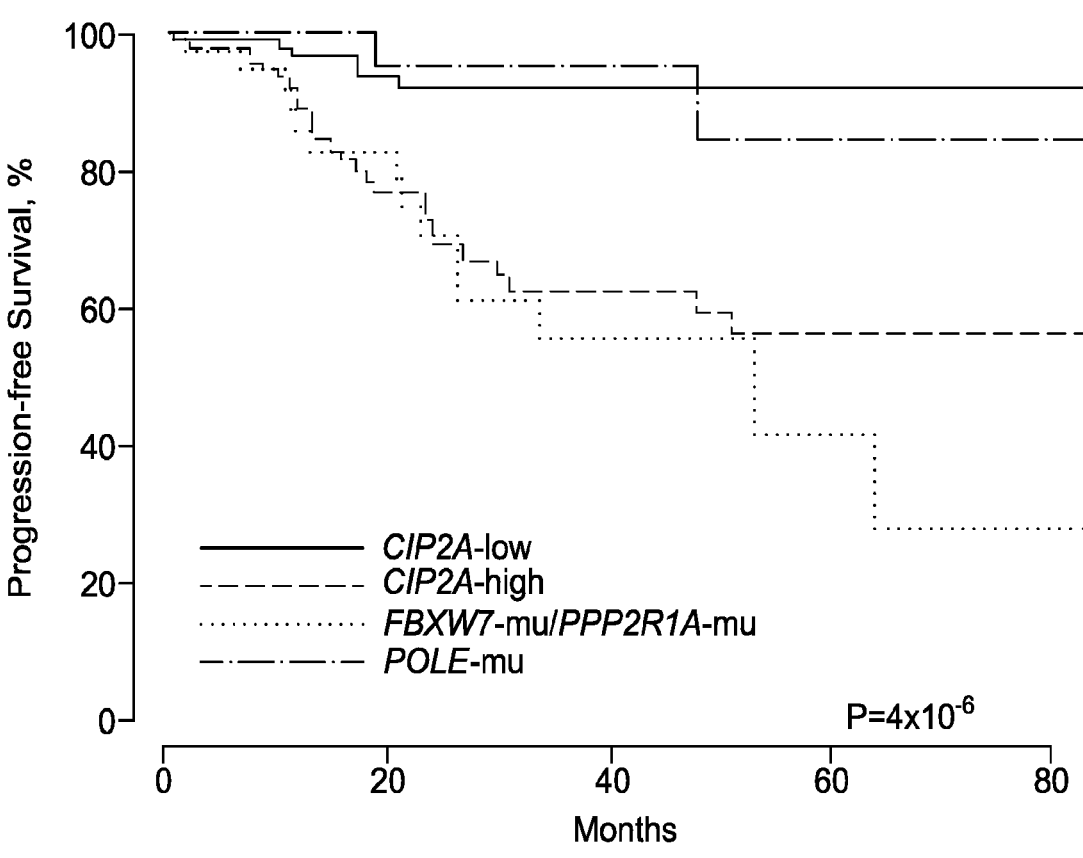
Figure 4A:
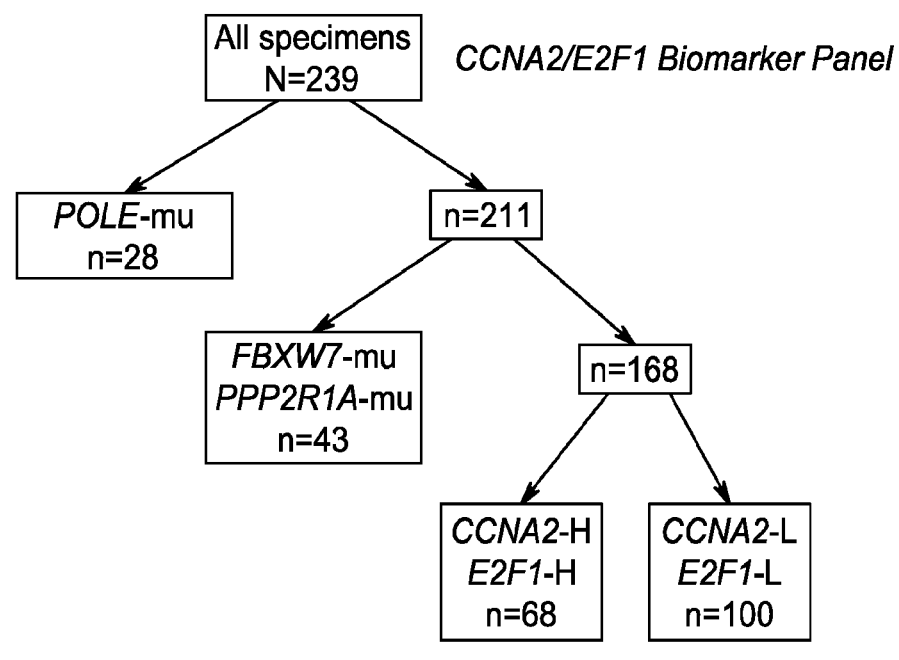
Figure 4B:
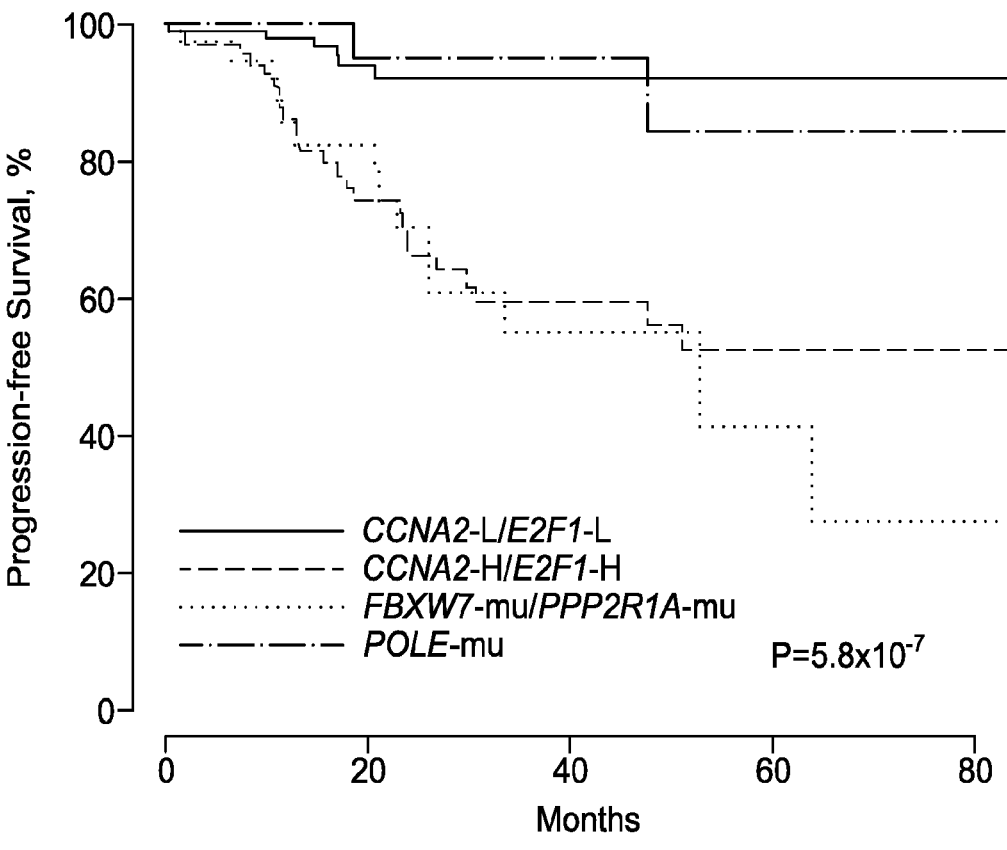

CCNA2 expression was replaced with CIP2A (CCNA2: CIP2A correlation coefficient 0.893) expression. Stratifying the molecular panel into POLE-mu, PPP2R1A-mu/FBXW7-mu, CIP2A-H and CIP2A-L (FIG. 3A) produced correspondingly significant discriminatory outcomes (FIG. 3B) as Recognizing the seminal role of CCNA2 in regulating E2F1 and indirectly CIP2A and FOXM1 in both p53-mu and p53-wt EC, it was postulated that "high" expression of either CCNA2 or E2F1 with more modest expression of the other would further discriminate outcomes. Slightly more restrictive levels for CCNA2 (≥2.75) and E2F1 (≥2.75) expression were used. This allowed stratifying EC into four molecular-based distinguishable cohorts (FIG. 4A) associated with distinct long-term PFS outcomes (FIG. 4B). Using the lower expression cohort for CCNA2 and E2F1 (CCNA2-L/E2F1-L) as the reference, Cox proportional survival analysis designated significant HRs for both the FBXW7-mu/PPP2R1A-mu and CCNA2-H/E2F1-H cohorts (FIG. 4C). Adjusting for age, grade, histology, MI, stage and p53 status, Cox proportional survival analysis demonstrated independent significance for CCNA2-H/E2F1-H (HR 5.33; p=0.0003), FBXW7-mu/PPP2R1A-mu (HR 6.46; p=0.0002) and stage (HR 1.38; p=0.017) (FIG. 4D).

Recurrences in Traditional "Low-Risk" and "High-Risk" EC According to Biomarker Panel Cohorts

Figure 5:
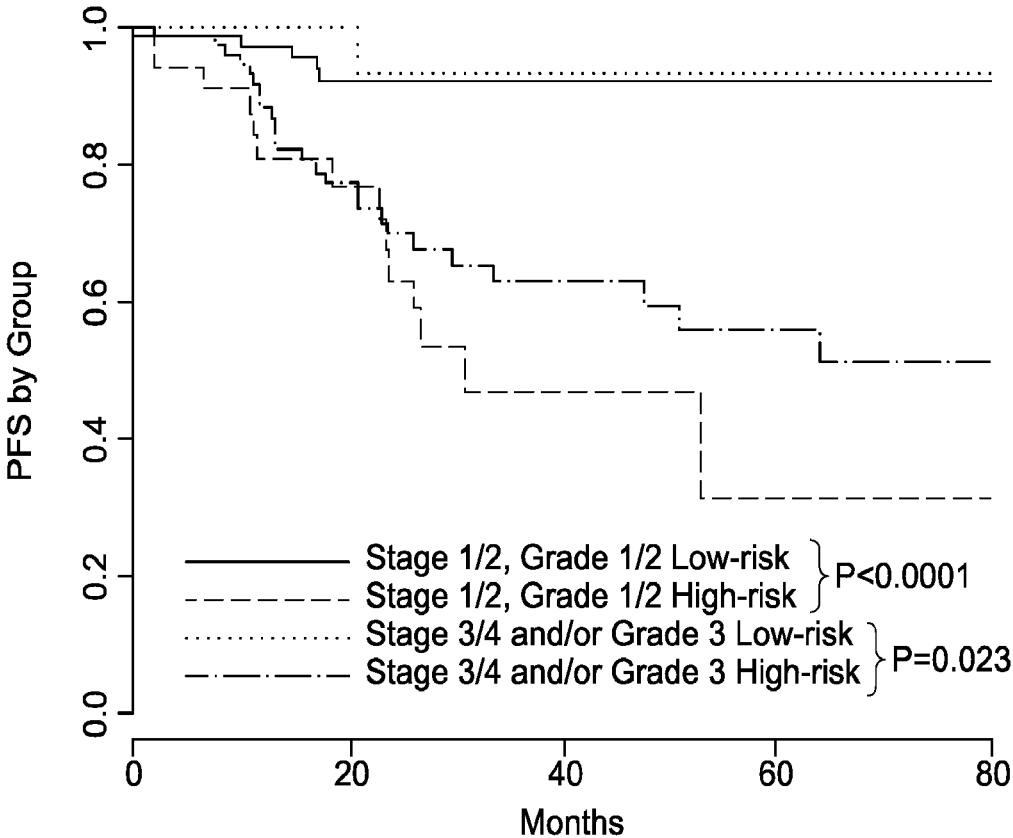
FIG. 5. Progression-free survival comparing stage 1/2, grade 1/2 EC with biomarker profile low-risk (N=75) to stage 1/2, grade 1/2 EC with biomarker profile high-risk (N=35) and stage 3/4 and/or grade 3 EC with biomarker profile low-risk (N=25) to stage 3/4 and/or grade 3 EC with biomarker profile high-risk (N=76). Low-risk is defined as CCNA2-L, E2F1-L, FBXW7-wt and PPP2R1A-wt and high-risk as CCNA2-H and/or E2F1-H and/or FBXW7-mu and/or PPP2R1A-mu.

Contemporary adjuvant therapy for "low-risk" EC (stage 1 or 2, grade 1 or 2) is generally very limited. These "low-risk" EC significantly (p<0.0001) stratified according to molecular panel cohorts; the estimated 5-year PFS for "low-risk" EC with the low-risk biomarker profile (CCNA2-L/E2F1-L/FBXW7-wt/PPP2R1A-wt) (N=75) was 92% compared to 31% for the "low-risk" EC with the high-risk biomarker profile (CCNA2-H/E2F1-H and/or FBXW7-mu/PPP2R1A-mu) (N=35) (FIG. 5). By contrast "high-risk" EC (stage 3 or 4 and/or grade 3) are frequently managed with adjuvant platinum-based chemotherapy (PbCT). Stratified by biomarker panel profiles, "high-risk" patients with the low-risk biomarker profile (N=25) appear to respond favorably to contemporary therapy (estimated 5-year PFS 93%) compared to those with the high-risk biomarker profile (N=76) (estimated 5-year PFS 56%) (p=0.023) (FIG. 5).

Clinical Outcomes in MSI-H and CNVL EC According to Biomarkers

The PFS associated with MSI-H (excluding POLE-mu) and CNVL according to CCNA2-L/E2F1-L/FBXW7-wt/PPP2R1A-wt versus CCNA2-H/E2F1-H and/or FBXW7-mu/PPP2R1A-mu was assessed. The biomarker panel cohorts separate both MSI-H (estimated 5-year PFS 95% and 42%, respectively) and CNVL (estimated 3-year PFS 92% and <50%, respectively) into two diverse prognostic subgroups (FIG. 6 and FIG. 7) suggesting an inclusive applicability for the molecular biomarker classification panel.

HR Pathway Gene Expression as Function of Adverse Biomarkers

Figure 8A:
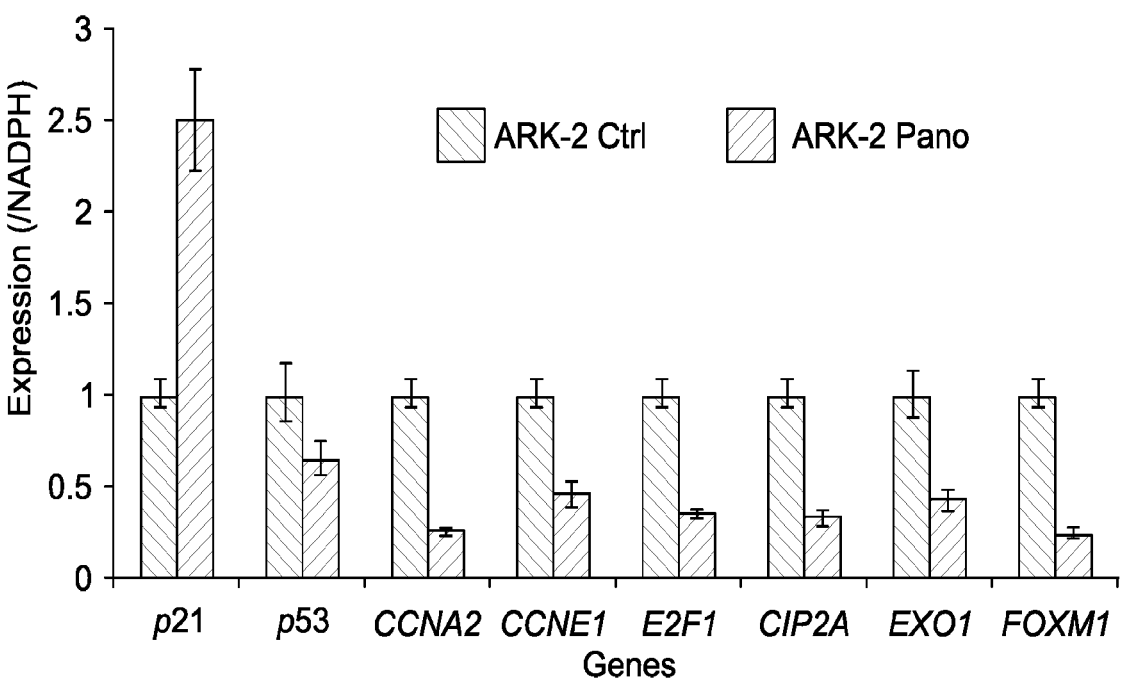
FIGS. 8A-8F. In vitro assessment of ARK-2 and HEC-1B cell lines response to MAC and AKT inhibitors. Following 24 hour exposure to panobinostat (HDACi) or vehicle, target-specific gene expression determined via qPCR in ARK-2 (FIG. 8A) and HEC-1B (FIG. 8B) cell lines. Cell viability assays in AKR-2 (FIG. 8C) and HEC-1B (FIG. 8D) cell lines following exposure to panobinostat or carboplatin alone and in combination were assessed to determine synergism. Cell viability assays were conducted in ARK-2 (FIG. 8E) and HEC-1B (FIG. 8F) cell lines following exposure to GSK2141795 (AKTi) or carboplatin and in combination to assess synergism.
Figure 8B:
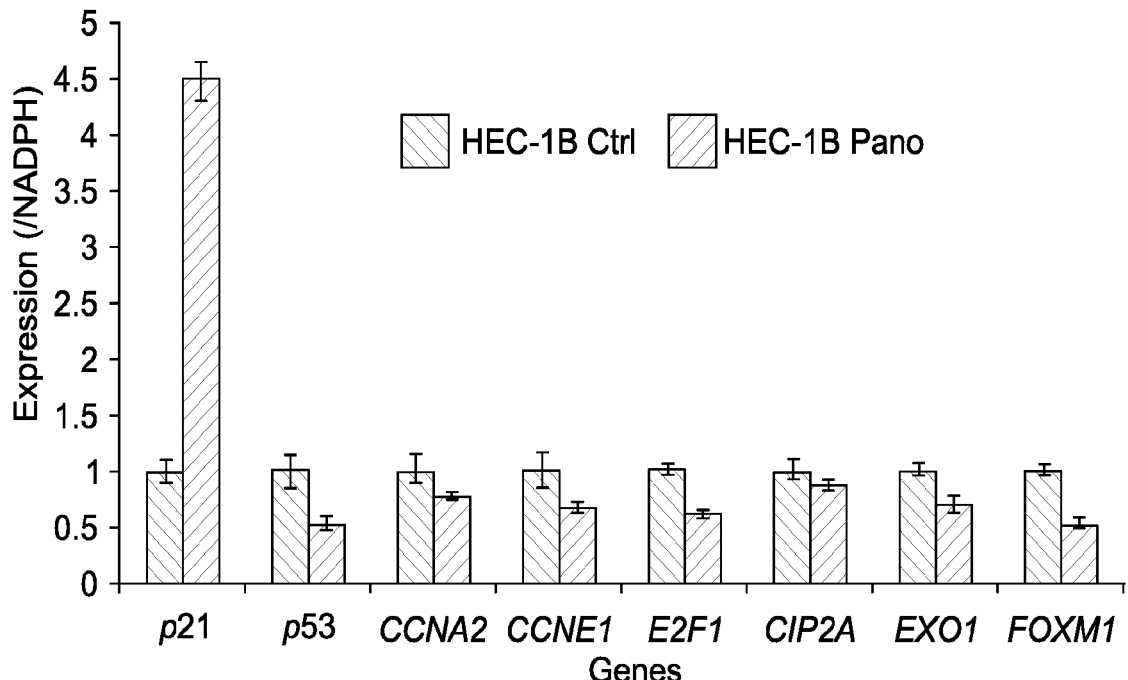
Figure 8C:
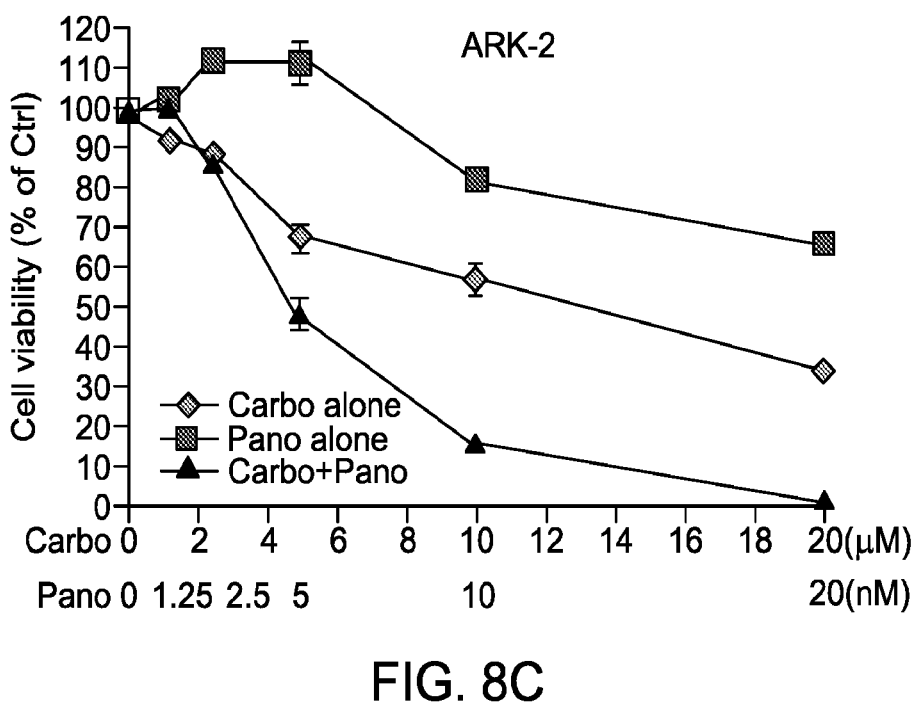
Figure 8D:
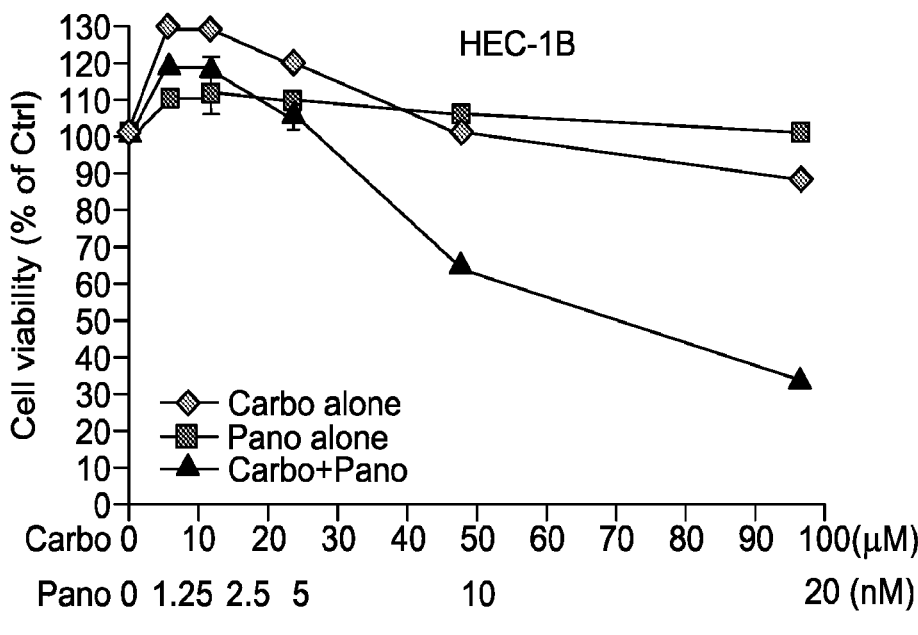

Compared to the CCNA2-L/E2F1-L cohort, the CCNA2-H/E2F1-H cohort demonstrates an increase in FOXM1 transcription. Moreover, the expression of CIP2A (KIAA1524) and the genes in the HR pathway (EXO1, BRIP1, Rad51, BRCA1, and BRCA2) reportedly induced by FOXM1 are upregulated in both the CCNA2-H/E2F1-H and FBXW7-mu/PPP2R1A-mu cohorts compared to the CCNA2-L/E2F1-L cohort (Table 3).

tivity. ARK-2 and HEC-1B cell lines exposed to varying concentrations of carboplatin and panobinostat demonstrated synergism (FIGS. 8C and D). These observations suggest suppression of FOXM1 and HR pathway components might enhance platinum sensitivity in high-risk HR proficient EC.

Figure 8E:
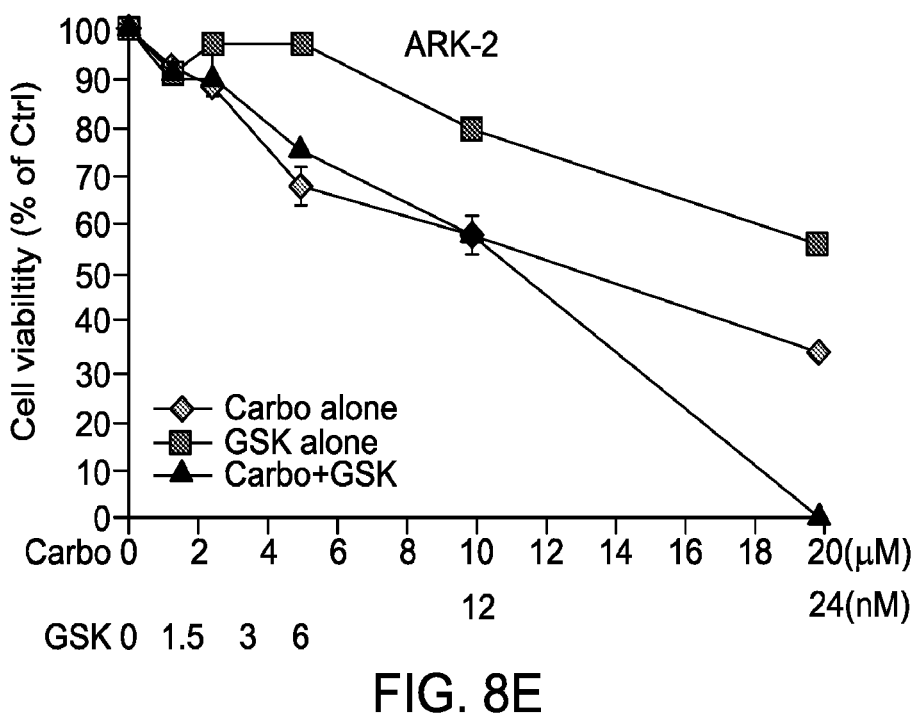
Figure 8F:
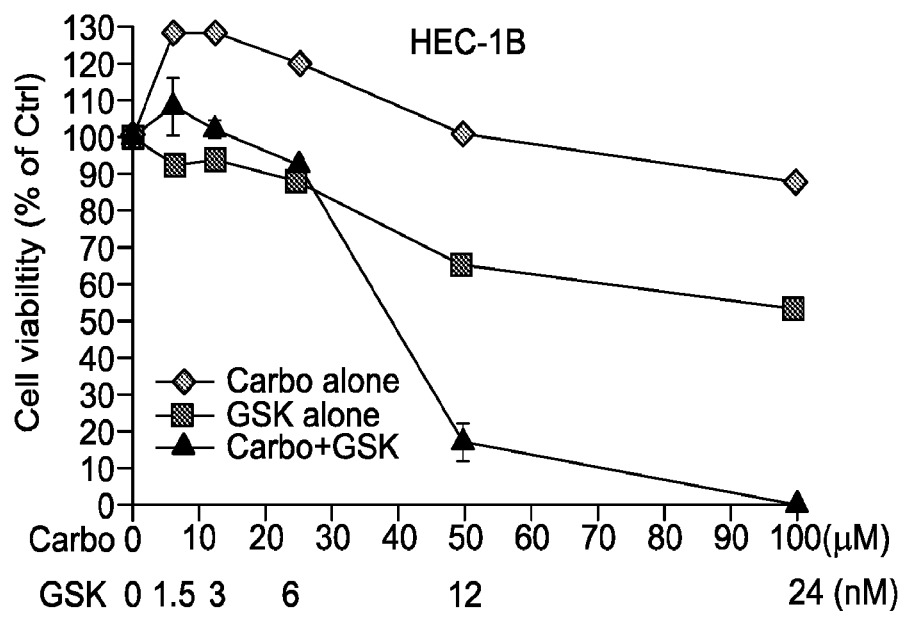

Considering AKT is activated in the greater majority of EC and lacks modulation in the presence of PPP2R1A-mu or unregulated CIP2A, the merits of inhibiting AKT in ARK-2 and HEC-1B cell lines alone and in combination with carboplatin was assessed. Simultaneous exposure of both cell lines to GSK2141795 (AKTi) and carboplatin demonstrated synergism (FIGS. 8E and F) suggesting the down regulation of the PI3K-AKT-FBW7 pathway as an additional potential strategy for enhancing platinum sensitivity in high-risk HR proficient EC.

Example 2: Platinum Based Cancer Drugs in Combination Therapies for Endometrial Cancer Methods Experiments were performed as described in Example 1.

Results

CCNA2 Panel

Figure 9A:
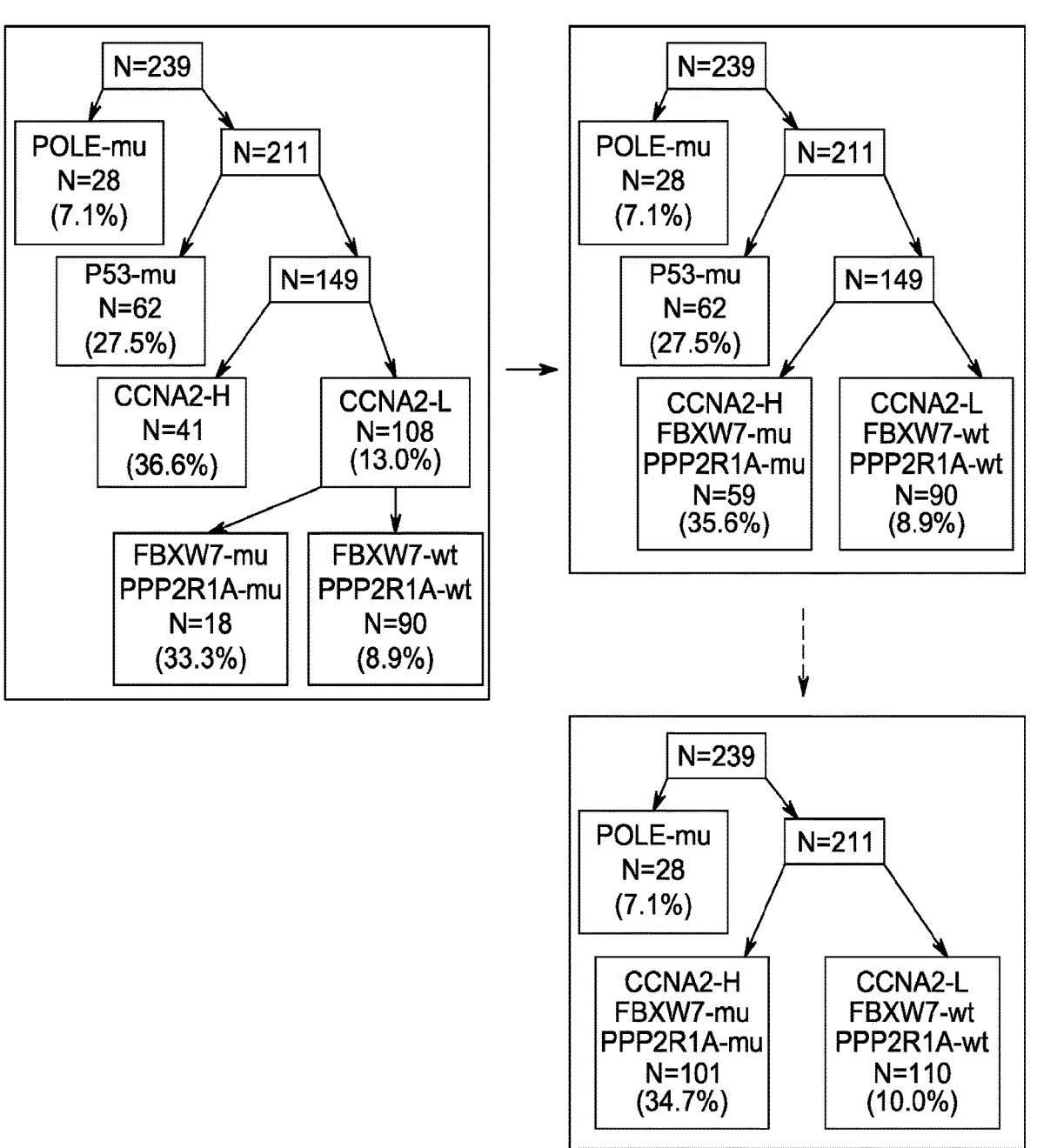

Mutations in FBXW7 and/or PPP2R1A were further stratified in specimens having CCNA2-L or CCNA2-H, and specimens with FBXW7 or PPP2R1A mutations were incorporated with CCNA2-H (FIG. 9A). Of the endometrial cancer patients having CCNA2-L/FBXW7-wt/PPP2R1A-wt specimens (N=26), 2 (7.7%) experienced recurrence of disease, and of the patients having CCNA2-H and/or

TABLE 3

Annotated expression of CIP2A, FOXM1 and multiple HR pathway genes as a function of molecular panel cohorts (excluding POLE-mu); CCNA2-L/E2F1-L (cohort A), CCNA2-H/E2F1-H (cohort B) and FBXW7-mu/PPP2R1A-mu (cohort C).

| Gene | mRNA Expression | | | Cohort A vs B | | Cohort A vs C | |
|---|---|---|---|---|---|---|---|
| | Cohort A Mean (SD) | Cohort B Mean (SD) | Cohort C Mean (SD) | Cohen's $d^\dagger$ | P | Cohen's $d^\dagger$ | P |
| CIP2A | 0.934 (0.958) | 2.477 (0.882) | 1.567 (1.251) | −1.662 | <0.001 | −0.600 | 0.001 |
| FOXM1 | 2.832 (0.721) | 4.340 (0.700) | 3.534 (0.898) | −2.112 | <0.001 | −0.903 | <0.001 |
| EXO1 | 0.015 (1.039) | 1.437 (0.807) | 0.764 (0.918) | −1.494 | <0.001 | −0.746 | <0.001 |
| RAD51 | 0.829 (0.775) | 2.138 (0.723) | 1.512 (0.950) | −1.735 | <0.001 | −0.822 | <0.001 |
| BRIP1 | −1.109 (0.890) | 0.052 (0.915) | −0.643 (0.961) | −1.289 | <0.001 | −0.511 | 0.006 |
| BRCA1 | 0.735 (0.778) | 1.665 (0.744) | 1.153 (0.941) | −1.216 | <0.001 | −0.504 | 0.007 |
| BRCA2 | −2.236 (1.295) | −0.686 (1.106) | −1.546 (1.365) | −1.268 | <0.001 | −0.524 | 0.005 |
| SKP2 | 1.926 (0.742) | 2.938 (0.738) | 2.276 (0.793) | −1.366 | <0.001 | −0.462 | 0.01 |
| MER11 | 0.663 (0.752) | 1.200 (0.716) | 0.738 (0.862) | −0.728 | <0.001 | −0.096 | 0.60 |

Induction of p21 and Repression of Panel-Specific Targets

The molecular schematic (FIG. 1A) predicts CDKN1A (p21) induction in p53-mu tumors would repress multiple oncogenes with downstream suppression of corresponding targets. ARK-2 (USC with p53-mu, FBXW7-wt and PPP2R1A-wt) and HEC-1B (p53-mu, FBXW7-mu, PPP2R1A-mu) platinum-insensitive cell lines, were exposed to panobinostat, an HDAC10 inhibitor, and qPCR expression of targeted genes analyzed. Increased expression of CDKN1A (p21) with down regulation of CCNA2, E2F1, CIP2A, FOXM1 and EXO1 was observed in both cell lines (FIGS. 8A and B).

Figure 9B:
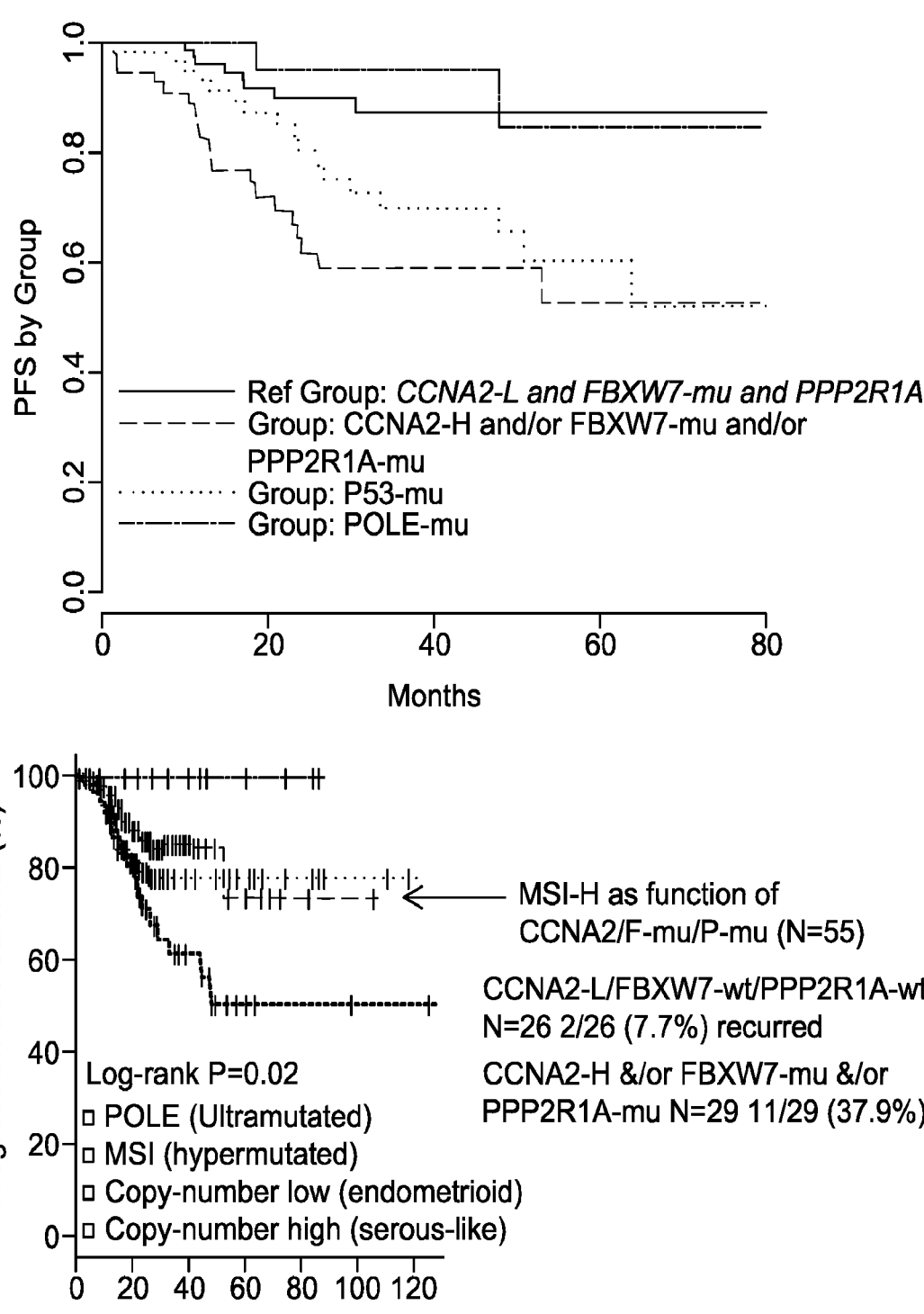

Synergism with HDAC or AKT Inhibitors and Carboplatin in Platinum Insensitive Cell Lines The down regulation of FOXM1 and HR pathway EXO1 with panobinostat in platinum insensitive cell lines suggested the potential for HDACi enhancing platinum sensi- FBXW7-mu and/or PPP2R1A-mu specimens (N=29), 11 (37.9%) experienced recurrence of disease (FIG. 9B). Cox proportional HR survival analysis using CCNA2-L and FBXW7-wt as reference assigned significance for CCNA2-H and/or FBXW7-mu and/or PPP2R1A-mu (HR 4.71; p=0.000) and p53-mu (HR 2.97; p=0.011) (FIG. 9C). Adjusting for age, histology, grade, myometrial invasion (MI), and stage, independent significance (PFS) was associated with CCNA2-H and/or FBXW7-mu and/or PPP2R1A-mu (p=0.000) and stage (p=0.002) (FIG. 9D).

These results demonstrate that a level of CCNA2 expression, the presence of one or more POLE mutations, the presence of one or more FBXW7 mutations, the presence of one or more PPP2R1A mutations, and, optionally, the presence of one or more p53 mutations can be used to determine whether or not patients having endometrial cancer are likely to respond to PbCT.

CIP2A Panel

Figure 10A:
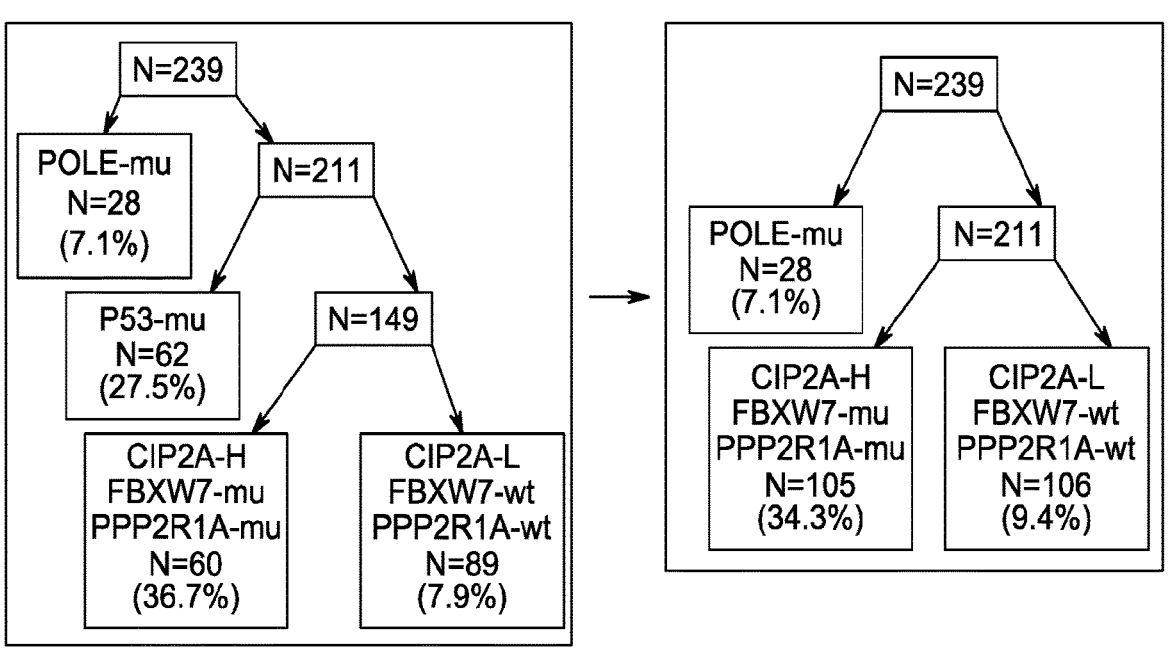
Figure 10B:
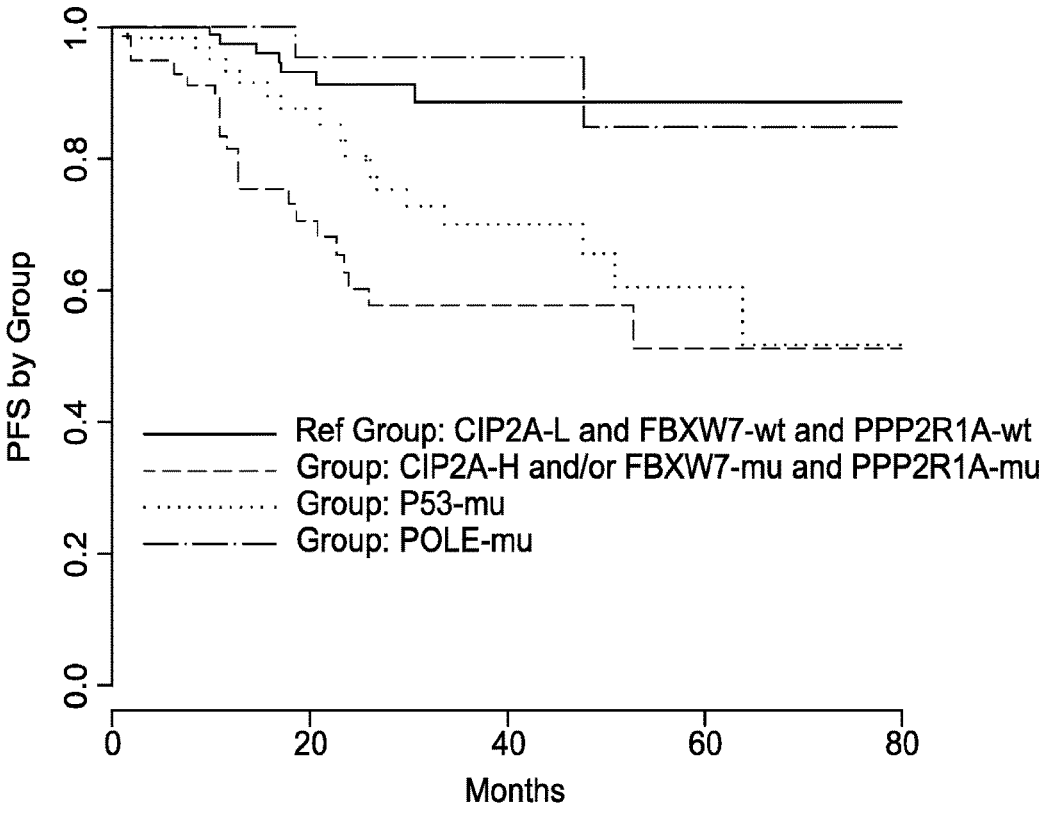
Figure 11:
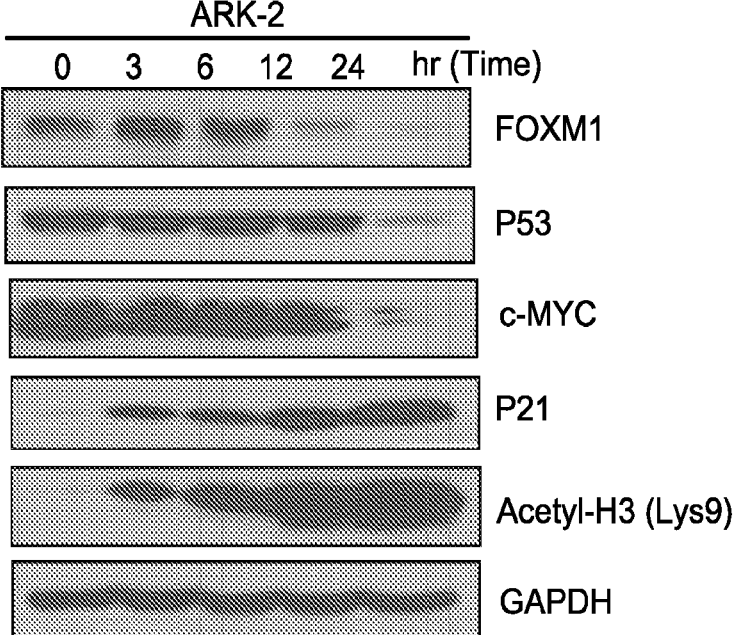
FIG. 11. Panobinostat inhibits the expression of FOXM1, c-Myc and p53, and induces the expression of p21, acetyl-H3 in a time-dependent manner.
Figure 12:
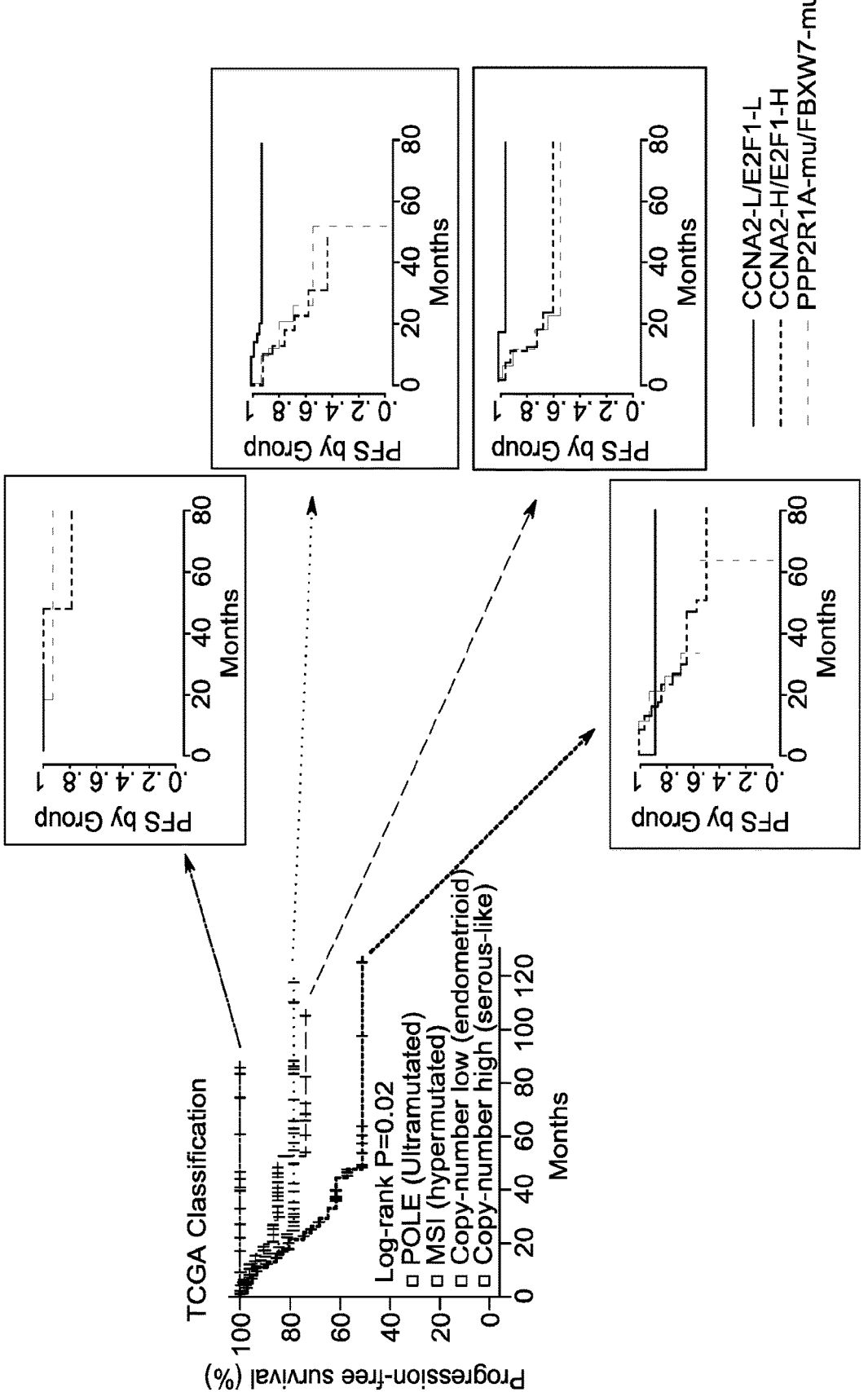
FIG. 12. Molecular classification of sub-stratified MSI-H and CNV-L.

Mutations in FBXW7 and/or PPP2R1A were further stratified in specimens having CIP2A-L or CIP2A-H, and specimens with FBXW7 or PPP2R1A mutations were incorporated with CIP2A-H (FIG. 10A). Progression free survival is shown in FIG. 10B. Of the Stage 1/2 and G1/2 endometrial cancer patients having CIP2A-L/FBXW7-wt/PPP2R1A-wt specimens (N=67), 6 (9%) experienced recurrence of disease, and of the patients having CIP2A-H and/or FBXW7-mu and/or PPP2R1A-mu specimens (N=36), 12 (33.3%) experienced recurrence of disease. Of the Stage 3/4 and G3 endometrial cancer patients having CIP2A-L/FBXW7-wt/PPP2R1A-wt specimens (N=22), 1 (4.5%) experienced recurrence of disease, and of the patients having CIP2A-H and/or FBXW7-mu and/or PPP2R1A-mu specimens (N=24), 10 (41.7%) experienced recurrence of disease. Cox proportional HR survival analysis using CIP2A-L, FBXW7-wt, and PPP2R1A-wt as reference assigned significance for CIP2A-H and/or FBXW7-mu and/or PPP2R1A-mu (HR 5.59; p=0.000) and p53-mu (HR 3.38; p=0.007) (FIG. 10C). Adjusting for age, histology, grade, myometrial invasion (MI), and stage, independent significance (PFS) was associated with CIP2A-H and/or FBXW7-mu and/or PPP2R1A-mu (p=0.000) and stage (p=0.002) (FIG. 10D).

These results demonstrate that a level of CIP2A expression, the presence of one or more POLE mutations, the presence of one or more FBXW7 mutations, the presence of one or more PPP2R1A mutations, and, optionally, the presence of one or more TP53 mutations can be used to determine whether or not patients having endometrial cancer are likely to respond to PbCT.

CCNA2/E2F1 Panel

Figure 6:
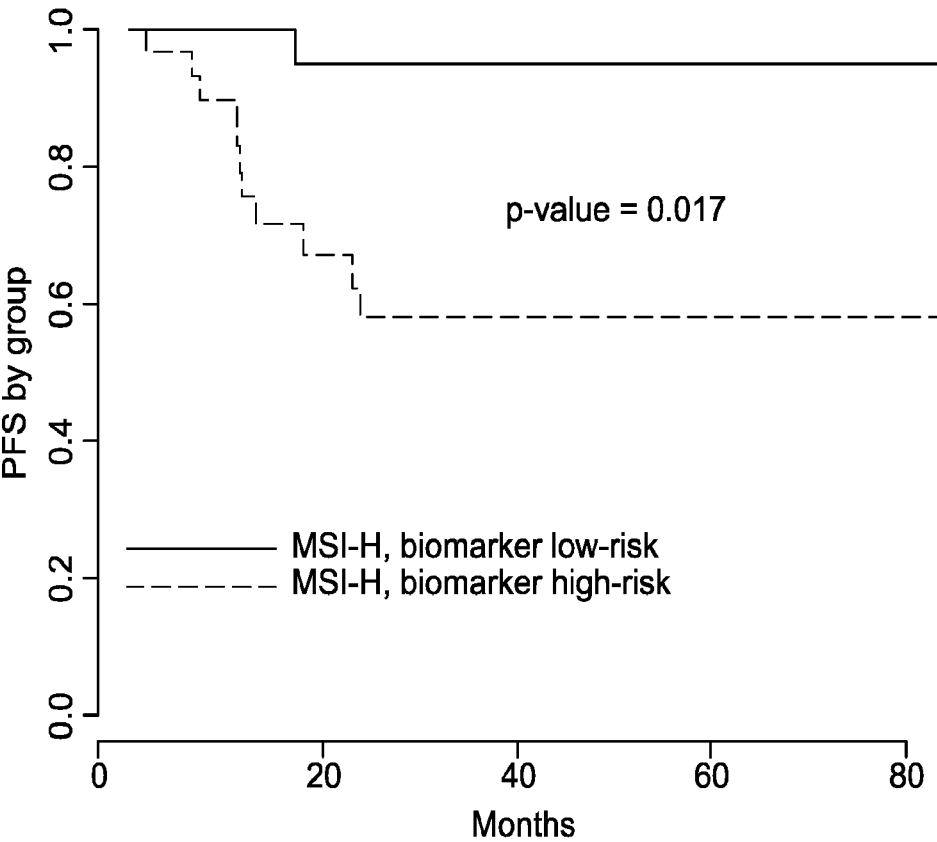
FIG. 6. Progression-free survival determined in patients with high microsatellite instability (MSI-H) EC according to biomarker panel low- and high-risk prognostic profiles. Low-risk biomarker profile characteristics include CCNA2-L, E2F1-L, FBXW7-wt and PPP2R1A-wt (N=28); high-risk profile include CCNA2-H and/or E2F1-H and/or FBXW7-mu and/or PPP2R1A-mu (N=32).
Figure 7:
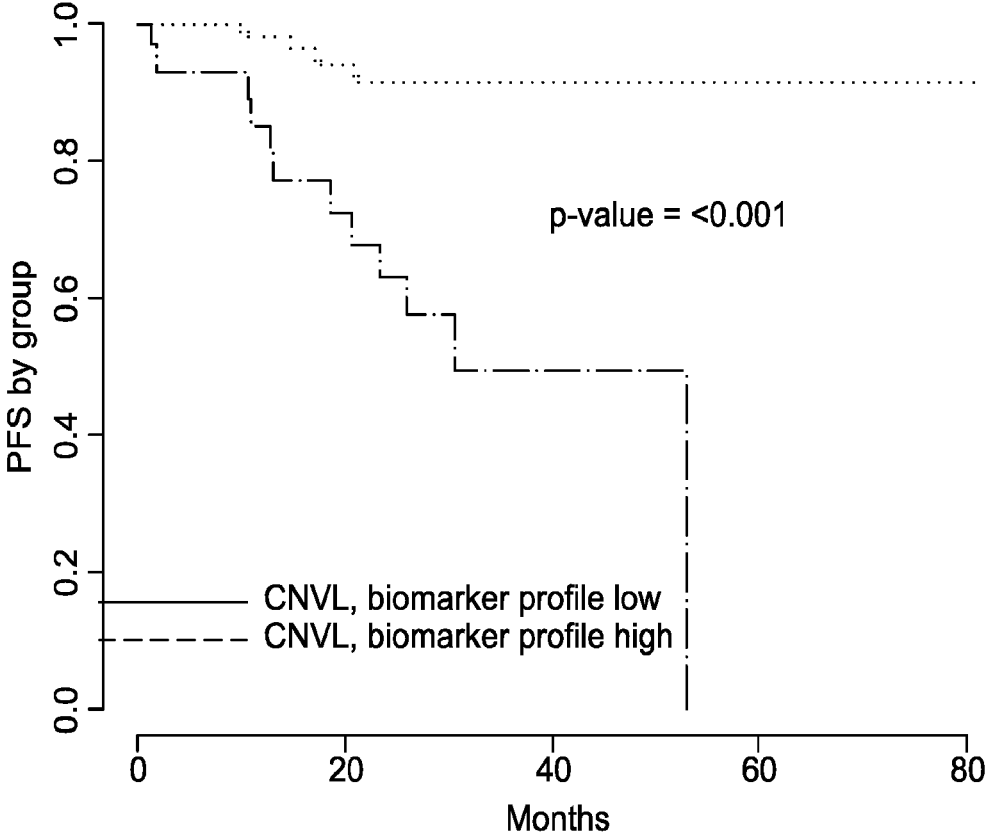
FIG. 7. Progression-free survival in patients with low copy number variation (CNVL) EC assessed according to biomarker panel low- and high-risk profiles. Low-risk biomarker profile characteristics include CCNA2-L, E2F1-L, FBXW7-wt and PPP2R1A-wt (N=63); high-risk profile include CCNA2-H and/or E2F1-H and/or FBXW7-mu and/or PPP2R1A-mu (N=30).

Mutations in FBXW7 and/or PPP2R1A were further stratified in specimens having CCNA2-H and E2F1-H (FIG. 4A). Percent recurrence and correlation with CIP2A and EXO1 mRNA expression are shown in FIG. 6 and FIG. 7.

These results demonstrate that a level of CIP2A expression, a level of E2F1 expression, the presence of one or more POLE mutations, the presence of one or more FBXW7 mutations, and the presence of one or more PPP2R1A mutations can be used to determine whether or not patients having endometrial cancer are likely to respond to PbCT.

Role of Histone Acetylation

The histone variant H2A.Z regulates p21 transcription in a p53 dependent manner. In p53-mu cell lines, histone deacetylase inhibitors (HDACi) induce p21 in an H2A.Z dependent manner. Following exposure of ARK-2 cells to panobinostat (HDACi), western blotting demonstrated a time dependent increase in acetyl-H3 and p21 and a corresponding decrease in FOXM1 and c-MYC. These observations suggest induction of p21 represses elements in the p53-p21-CDE/CH4 pathway and downstream components in the PI3K-AKT-FBW7 axis (e.g., FOXM1 and c-Myc) and are consistent with Example 1. The induction of p21 with corresponding repression of FOXM1 and anticipated restricted induction of homologous recombination (HR) pathway genes signals impaired DNA damage repair and potential enhanced platinum sensitivity in HR-proficient EC.

Example 3: ECPPF Classification: Projecting Occult Extrauterine Disease and Therapeutic Insensitivity in Endometrioid Endometrial Cancer Methods Experiments were performed as described in Example 1 and Example 2.

Results

DNA sequencing and RNA expression were annotated in 192 EEC cases in TCGA EC database to allow weighing molecular aberrations with clinicopathologic risk factors and adverse surveillance events. POLEmu were detected in 28 cases (14.6%) and served as a metric for favorable prognosis but excluded from integrative assessments. The study population of 164 cases had a median age of 61, and included 124 stage I (21 grade (G) 3), 10 stage II (3 G3), 23 stage III (6 G3) and 7 stage IV (6 G3) cases. PPP2R1Amu and FBXW7mu were present in 15 (9.1%) and 9 (5.5%) cases, respectively. TP53mu were detected in 21 (12.8%) cases including 1/63 case in G1, 8/65 in G2 and 12/36 cases in G3 tumors. $\geq 1$ HRmu was present in 34 (20.7%) cases. High microsatellite instability (MSI-H) was assigned to 58 (35.4%) and TCGA NSMP (no specific molecular profile) to 89 cases. Treatment failures were documented in 31 (18.9%) cases, and among the other 133 patients, the median duration of follow-up was 28.6 months (interquartile range, 16.8-46.8).

Figure 13A:
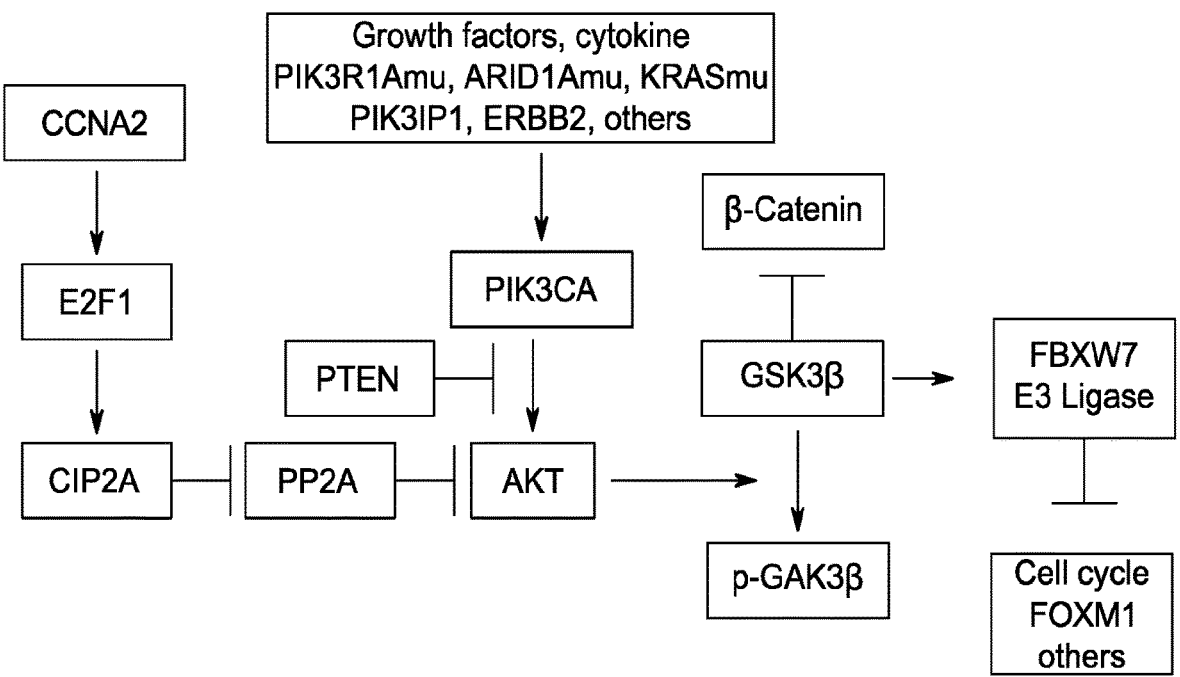
Figure 13B:
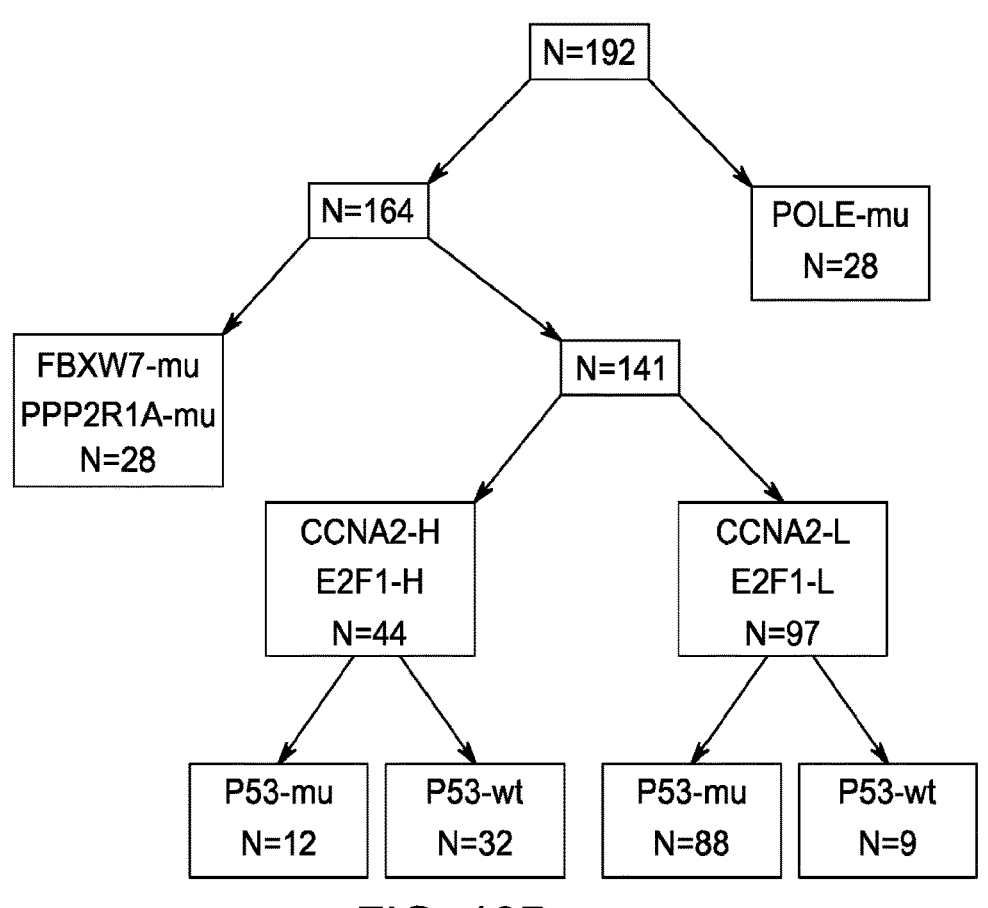
Figure 13C:
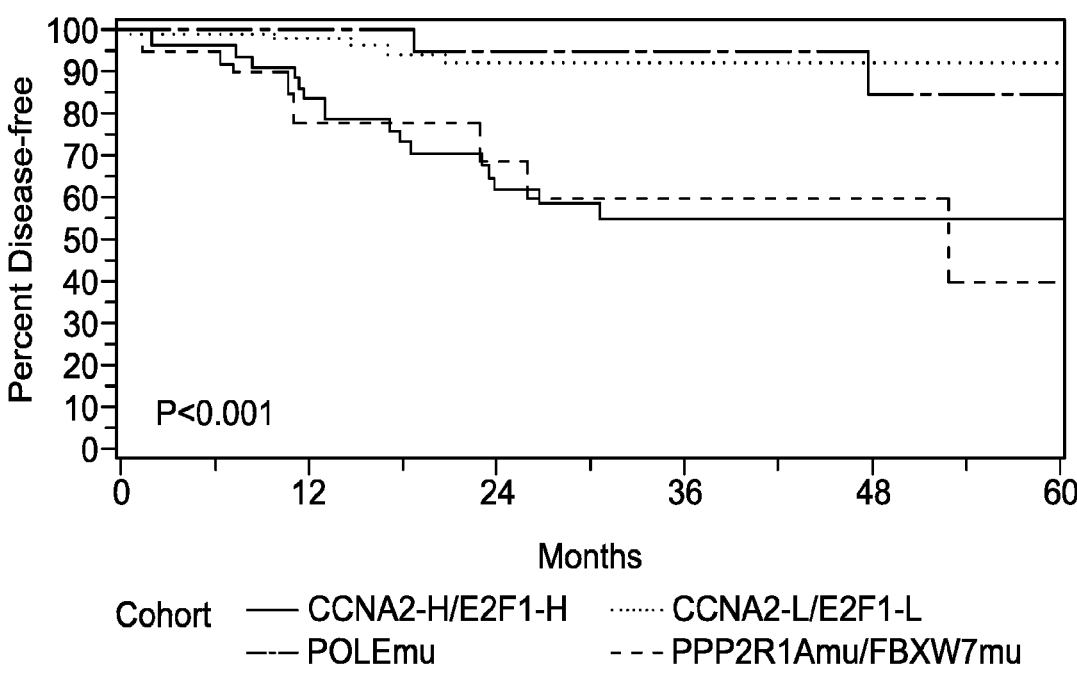

CCNA2-E2F1-CIP2A axis and PI3K-AKT pathway elements form the grid for ECPPF (FIGS. 13A and 13B). PFS was assessed as a function of the previous reported ECPPF discriminating molecular parameters. CCNA2 or E2F1 expression$\geq 2.75$ (CCNA2-H/E2F1-H) versus both <2.75 (CCNA2-L/E2F1-L) and mutations in PPP2R1A or FBXW7 or both. PFS analysis demonstrated ECPPF molecular-based cohorts significantly differentiated EEC clinical outcomes (P<0.001) (FIG. 13C). PFS for cases harboring CCNA2-L/E2F1-L and POLEmu tumors appeared nearly equivalent. These results suggest ECPPF readily discriminates EEC responses to contemporary therapy.

Figure 13D:
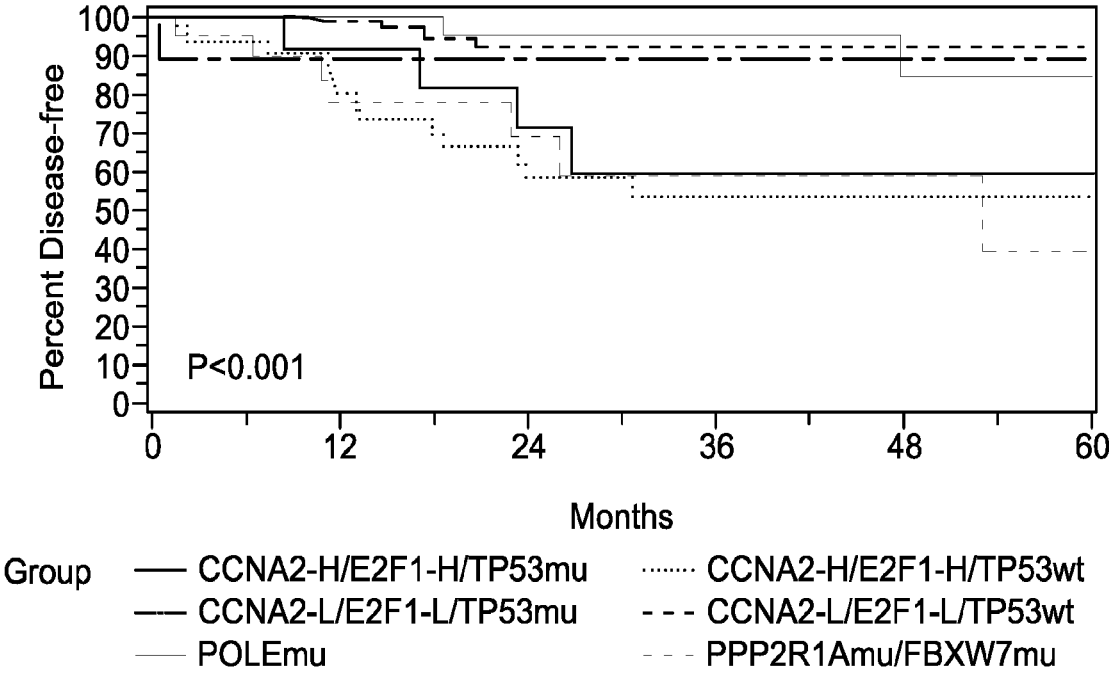

TP53mu was integrated into ECPPF. TP53mu was mutually exclusive to PPP2R1mu and FBXW7mu (p=0.013). Among 21 TP53mu cases, PFS aligned with CCNA2/E2F1 expression (FIG. 13D). Cox proportional modeling strengthened these observations and inferred ECPPF was independent of TP53mu (FIG. 13E). A stepwise multivariate analysis considering variables with p<0.20 (age, grade, depth of myometrial invasion (MI), stage, MSI-H, NSMP, TP53mu, HRmu, CTNNB1 mu, KRASmu, ARID1A mu, PIK3CA mu, PTENmu, PIK3R1mu, CIP2A expression, and ECPPF parameters) demonstrated independent significance for only CCNA2-H/E2F1-H and PPP2R1Amu/FBXW7mu (vs CCNA2-L/E2F1-L) and stage IV disease (FIG. 13F).

Disparate responses of ECPPF subgroups to contemporary therapy suggested potential divergent levels of DNA damage repair (DDR) and cell cycle dysregulation. The expressions of multiple cell cycle and DDR genes were annotated within the CCNA2-HI E2F1-H, PPP2R1Amu/FBXW7mu and CCNA2-L/E2F1-L cohorts (Table 4). Differences in expression of numerous cell cycle, DDR, historic prognostic, and other genes exist between CCNA2-H/E2F1-H and both CCNA2-L/E2F1-L and PPP2R1Amu/FBXW7mu cohorts. Notwithstanding the difference in PFS between CCNA2-L/E2F1-L and PPP2R1Amu/FBXW7mu cohorts (FIG. 13C), their abridged molecular profiles were remarkably similar. The extremely low expression of DDR and cell cycle genes in CCNA2-L/E2F1-L cases portends "functional HR deficiency" and favorable responses to contemporary therapy. By contrast, the exceedingly high expression of these genes in CCNA2-H/E2F1-H suggests enhanced HR proficiency and in the absence of HRmu likely insensitivity to conventional therapy (FIG. 13C).

TABLE 4

| | Cohort A CCNA2-H/ E2F1-H | Cohort B CCCNA2-L/ E2F1-L | Cohort C FBXW7-mu/ PPP2R1A-mu | Gene Expression Comparing Cohorts P values | |
|---|---|---|---|---|---|
| Genes | N = 44 | N = 97 | N = 23 | A to B | B to C |

Gene expression (mean (standard deviation)) as a function of molecular high-and low-risk endometrioid endometrial cancer cohorts.

| | | | | | |
|---|---|---|---|---|---|
| | | CCNA2-E2F1-CIP2A Axis | | | |
| CCNA2 | 3.215 (0.787) | 1.573 (0.829) | 1.910 (0.894) | 8.247E−21 | 0.087 |
| E2F1 | 3.217 (1.055) | 1.378 (0.712) | 1.796 (0.755) | 1.349E−23 | 0.013 |
| CIP2A | 2.400 (0.963) | 0.895 (0.934) | 0.955 (0.994) | 5.303E−15 | 0.782 |
| | | Cell Cycle Genes | | | |
| CCNB1 | 5.297 (0.707) | 3.926 (0.686) | 4.255 (0.722) | 2.473E−20 | 0.043 |
| CCNB2 | 4.706 (0.697) | 3.302 (0.789) | 3.579 (0.839) | 1.993E−18 | 0.138 |
| CCNE1 | 3.251 (1.274) | 2.117 (1.220) | 1.933 (1.013) | 1.392E−06 | 0.504 |
| AURKA | 3.108 (0.837) | 1.644 (0.754) | 1.826 (0.699) | 6.756E−19 | 0.294 |
| TPX2 | 4.226 (0.741) | 2.653 (0.778) | 2.893 (0.761) | 2.259E−21 | 0.185 |
| PLK1 | 4.518 (0.828) | 2.823 (0.795) | 3.186 (0.878) | 4.021E−22 | 0.056 |
| ESPL1 | 1.971 (0.816) | 0.253 (0.844) | 0.429 (0.864) | 2.011E−21 | 0.375 |
| CHEK1 | 2.634 (0.698) | 1.646 (0.494) | 1.881 (0.593) | 4.513E−17 | 0.051 |
| | | FOXM1 and DNA Damage Repair Genes | | | |
| FOXM1 | 4.393 (0.735) | 2.802 (0.709) | 3.024 (0.665) | 9.553E−24 | 0.174 |
| BRCA1 | 1.828 (0.773) | 0.714 (0.774) | 0.994 (0.738) | 6.530E−13 | 0.117 |
| BRCA2 | −0.749 (1.233) | −2.288 (1.269) | −2.090 (1.141) | 4.141E−10 | 0.495 |
| Rad51 | 2.209 (0.748) | 0.811 (0.779) | 1.072 (0.944) | 4.500E−18 | 0.167 |
| BRIP1 | 0.104 (0.893) | −1.148 (0.870) | −0.955 (0.803) | 9.950E−13 | 0.334 |
| EXO1 | 1.487 (0.861) | −0.016 (1.039) | 0.445 (0.968) | 5.303E−14 | 0.055 |
| MRE11A | 1.120 (0.761) | 0.672 (0.730) | 0.530 (0.796) | 0.001 | 0.411 |
| Rad50 | 2.222 (0.780) | 2.069 (0.634) | 1.840 (0.572) | 0.221 | 0.116 |
| NBN | 2.732 (0.830) | 2.387 (0.830) | 2.321 (0.790) | 0.024 | 0.729 |
| ATR | 1.700 (0.574) | 1.669 (0.504) | 1.461 (0.403) | 0.747 | 0.067 |
| ATM | 4.329 (0.708) | 4.316 (0.682) | 4.212 (0.784) | 0.916 | 0.525 |
| SKP2 | 2.916 (0.795) | 1.922 (0.751) | 1.959 (0.710) | 4.500E−11 | 0.828 |
| PARP1 | 5.431 (0.621) | 4.721 (0.795) | 4.886 (0.804) | 5.925E−07 | 0.375 |
| | | Historic Prognostic Markers | | | |
| ATAD2 | 2.337 (0.869) | 0.833 (0.915) | 1.162 (0.754) | 5.173E−16 | 0.112 |
| BIRC5 | 5.883 (0.923) | 4.307 (0.780) | 4.571 (0.733) | 2.581E−19 | 0.143 |
| EZH2 | 2.993 (0.622) | 2.165 (0.628) | 2.103 (0.632) | 2.407E−11 | 0.669 |
| L1CAM | 1.901 (4.754) | 0.306 (0.631) | 0.396 (1.027) | 0.0014 | 0.589 |
| STMN | 7.121 (1.093) | 6.288 (0.951) | 6.479 (1.317) | 9.617E−06 | 0.426 |

Figure 14A:
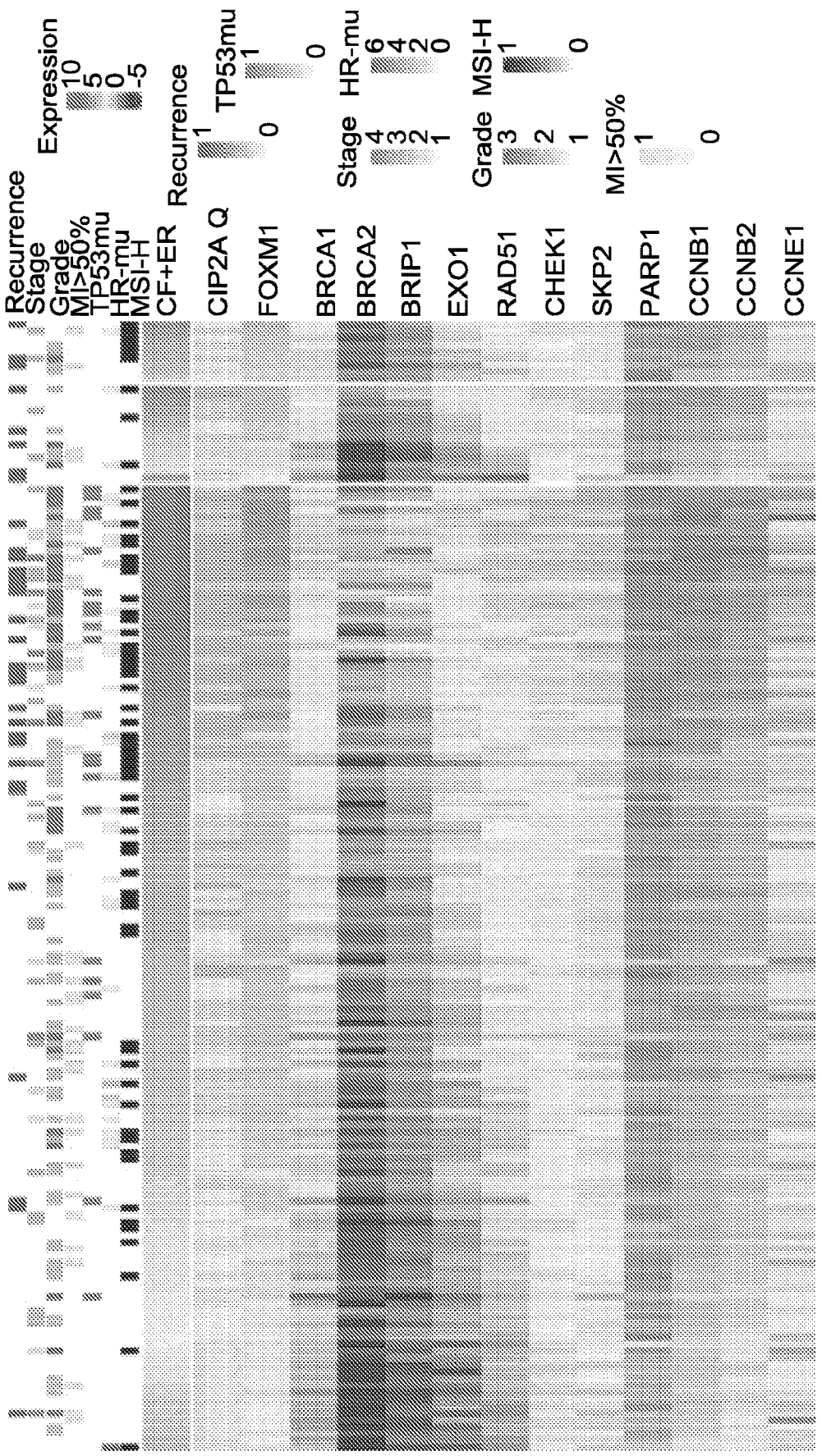
FIGS. 14A-14B. Gene Expression and Treatment Failures.
Figure 14B:
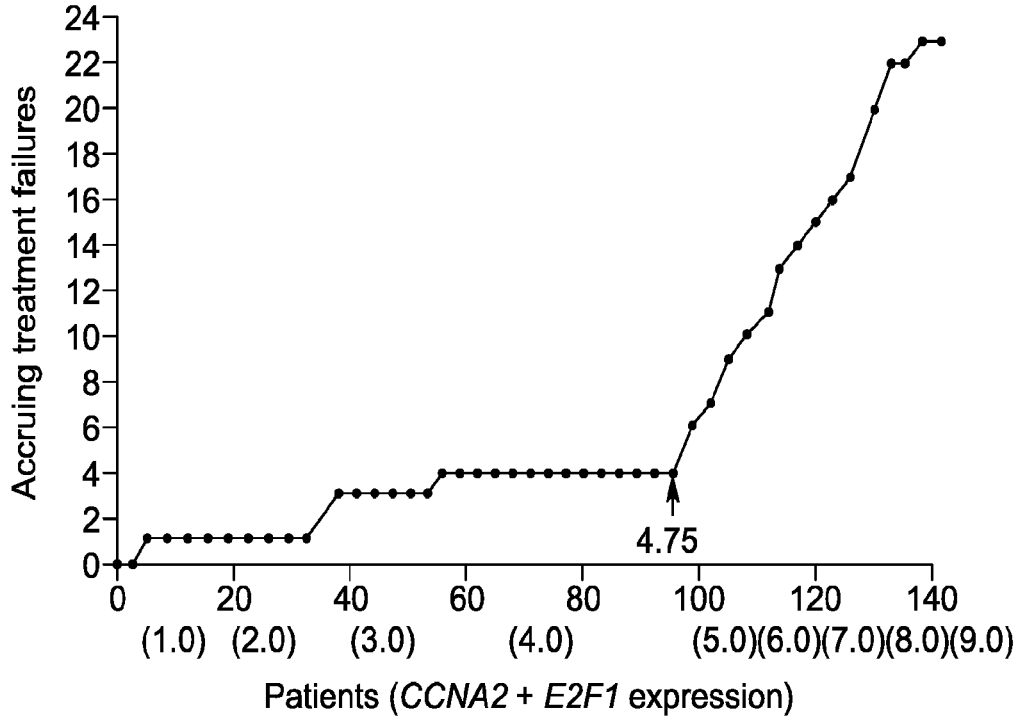

The quantitative expression of CCNA2 and E2F1 (CA2+E2F) was compared with cell cycle and DDR gene expressions to further weigh the interdependence of these transcriptomic markers. As CA2+E2F expression progressively increased, a near parallel increase was witnessed in CIP2A, FOXM1, cell cycle and HR gene expression (FIG. 14A). Pearson's correlation (r) for CA2+E2F and CIP2A was 0.796, was 0.918 for FOXM1, was 0.549-0.859 for cell cycle genes, and was 0.683-0.846 for HR genes. Increasing C2A+E2F appeared associated with an elevated prevalence of G3 histology, TP53mu, MSI-H, HRmu and treatment failures. Excluding PPP2R1Amu/FBXW7mu, cumulative recurrences sharply increased when C2A+E2F expression exceeded 4.75 (FIG. 14B). These results advocate for ECPPF's potential in predicting failure in low-risk and treatment insensitivity in high-risk tumors.

Figure 15A:
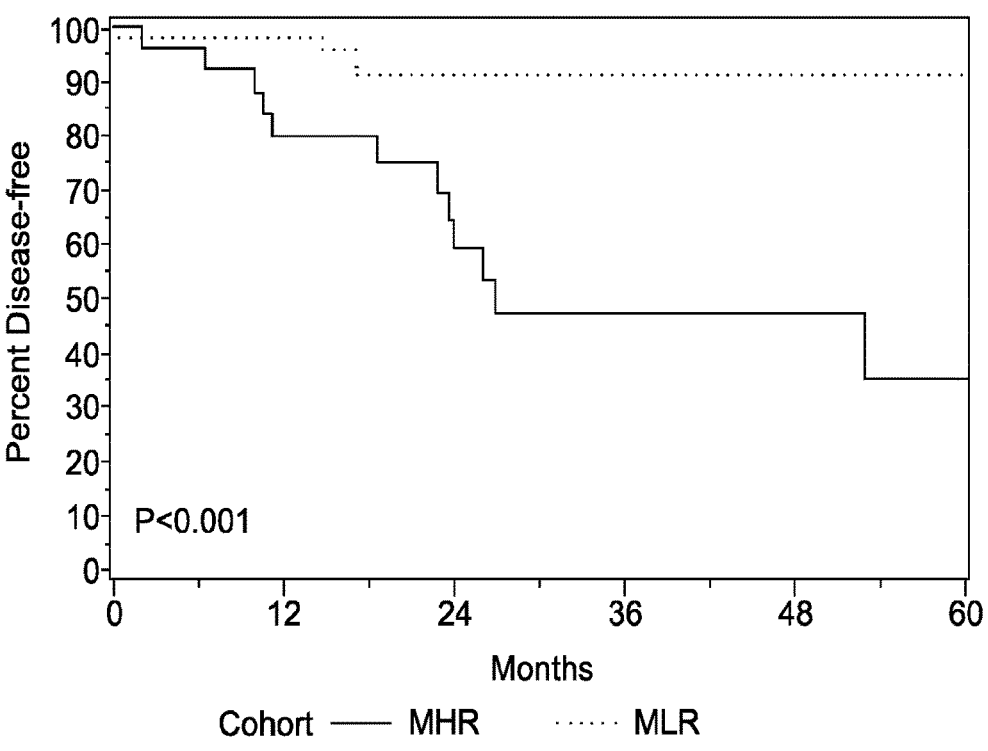
FIGS. 15A-15E. ECPPF stratification of outcomes in endometrioid endometrial cancer.
Figure 15B:
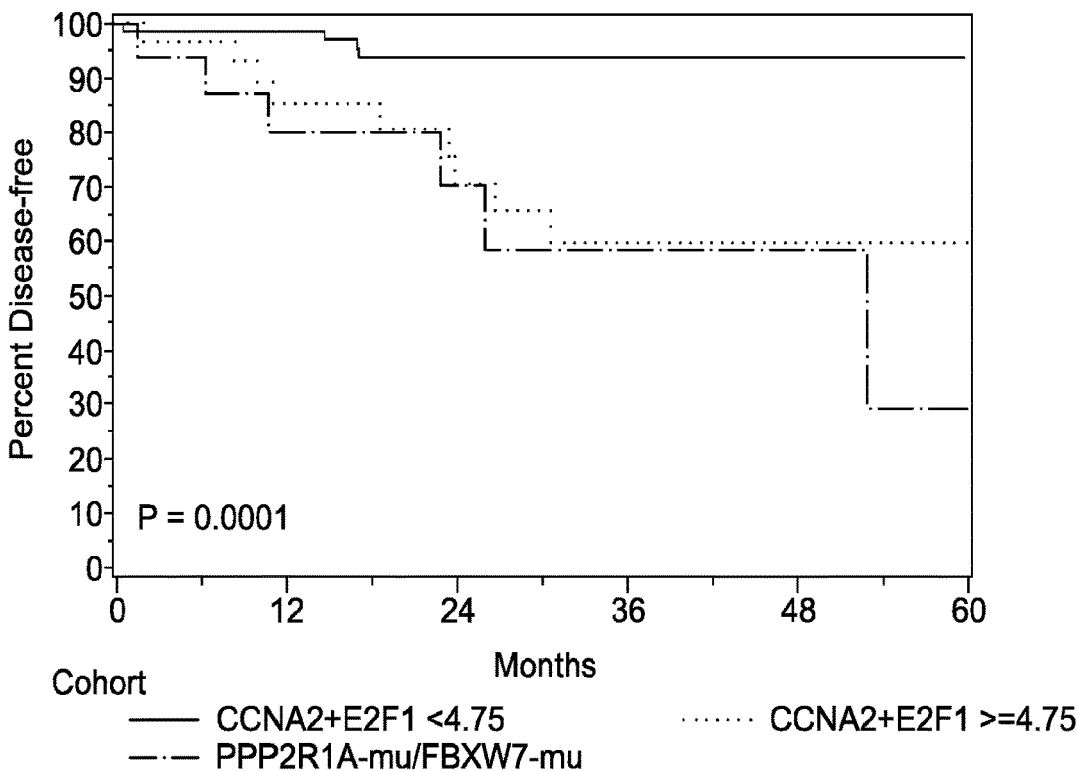

ECPPF's discrimination of EEC clinical outcomes independent of early stage and histologic grade (FIG. 13F) implied ECPPF might distinguish early stage low-grade cases at significant risk for occult extrauterine disease and subsequent recurrence. Recurrences were annotated according to stage, and within stage I by grade, and assessed as a function of ECPPF molecular low risk (MLR; CA2+E2F<4.74) and high risk (MHR; CA2+E2F≥4.75, PPP2R1Amu, and/or FBXW7mu). Among 103 stage I, grade 1 and 2, occult extrauterine disease escaping surgical detection was subsequently documented in 20 (19.4%) cases. 6/52 (11.5%) cases were grade 1 cases and 14/52 (27.5%) cases were grade 2 cases (Table 5). ECPPF MLR was identified in 69/103 (67%) of early stage low-grade cases, and MHR in 34 (33%) of early stage low-grade cases. Recurrences were documented in 4/69 (5.8%) MLR cases and in 16/34 (47%) MHR cases. Amid 85 stage I, G1/2, ≤50% MI cases, rarely candidates for adjuvant therapy, 5-year PFS analysis illustrates divergent outcomes according to ECPPF (p<0.001) (FIG. 15A). Similar ECPPF discrimination was observed when expanding the cohort to stage I/II, G 1/2<75% MI and G3<50% MI (p=0.0001) (FIG. 15B). These results suggest ECPPF identifies early stage, low-risk EEC patients at substantial risk for recurrence (harboring occult extrauterine disease) who are candidates for early therapeutic intervention.

TABLE 5

| | Number and recurrences per cohort | | | | | |
| | MLR + MHR | | MLR | | MHR | |
| Characteristic | No. | Recur (%) | No. | Recur (%) | No. | Recur (%) |
|---|---|---|---|---|---|---|
| Stage I | | | | | | |
| Grade I | 52 | 6 (11.5) | 38 | I (2.6) | 14 | 5 (35.7) |
| Grade 2 | 51 | 14 (27.5) | 31 | 3 (9.7) | 20 | 11 (55.0) |
| | 103 | 20 (19.4) | 69 | 4 (5.8) | 34 | 16 (47.1) |
| Stage I | | | | | | |
| Grade 3 | 21 | 1 (4.8) | 5 | 0 (—) | 13 | 1 (7.7) |
| Stage II | 10 | 0 (—) | 5 | 0 (—) | 5 | 0 (—) |
| Stage III | 23 | 5 (21.7) | 13 | 0 (—) | 10 | 5 (50.0) |
| Stage IV | 7 | 5 (71.4) | 3 | 2 (66.7) | 4 | 3 (75.0) |
| Total | 164 | 31 (18.9) | 98 | 6 (6.1) | 66 | 25 (37.9) |

Figure 15C:
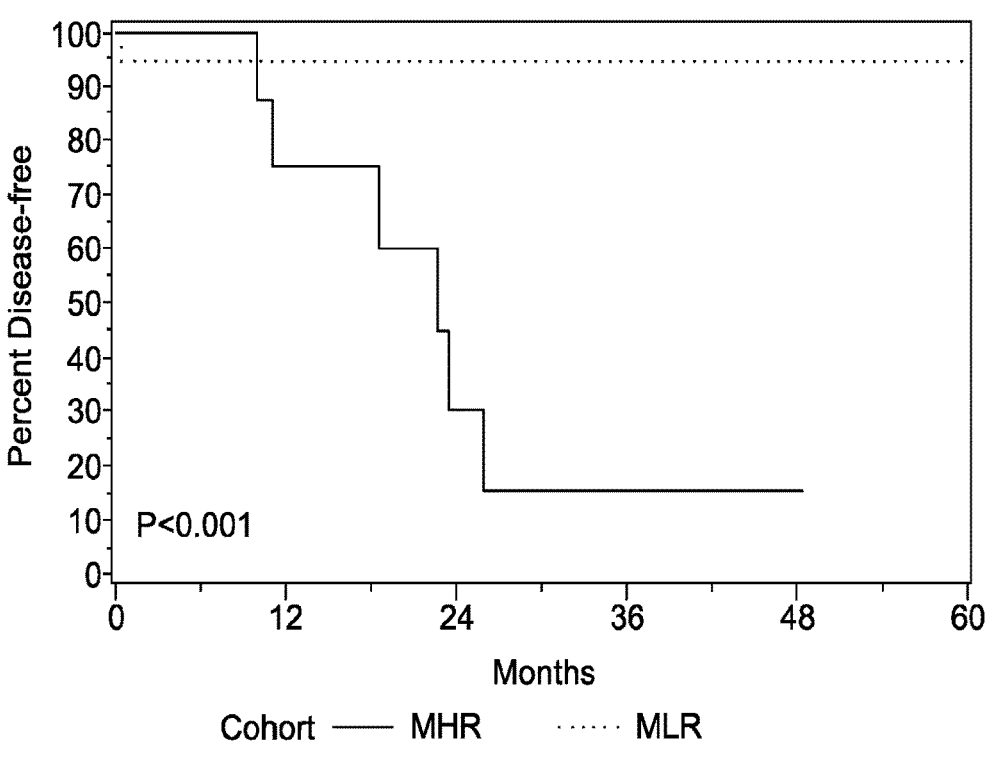

CTNNB1mu in low-risk EEC is reportedly associated with adverse outcomes. CTNNB1mu were identified in 28 early stage low-risk (stage I, G1/2, ≤50% MI) EEC. 7/28 (25%) CTNNB1mu cases had documented recurrences and 6/7 (85%) occurred among the 9 ECPPF MHR cases. ECPPF catalogues early stage low-risk CTTNB1mu cases (p<0.001) (FIG. 15C). These results further underscore the discriminating utility of ECPPF to characterize adverse outcomes in traditional low-risk patients.

Figure 15D:
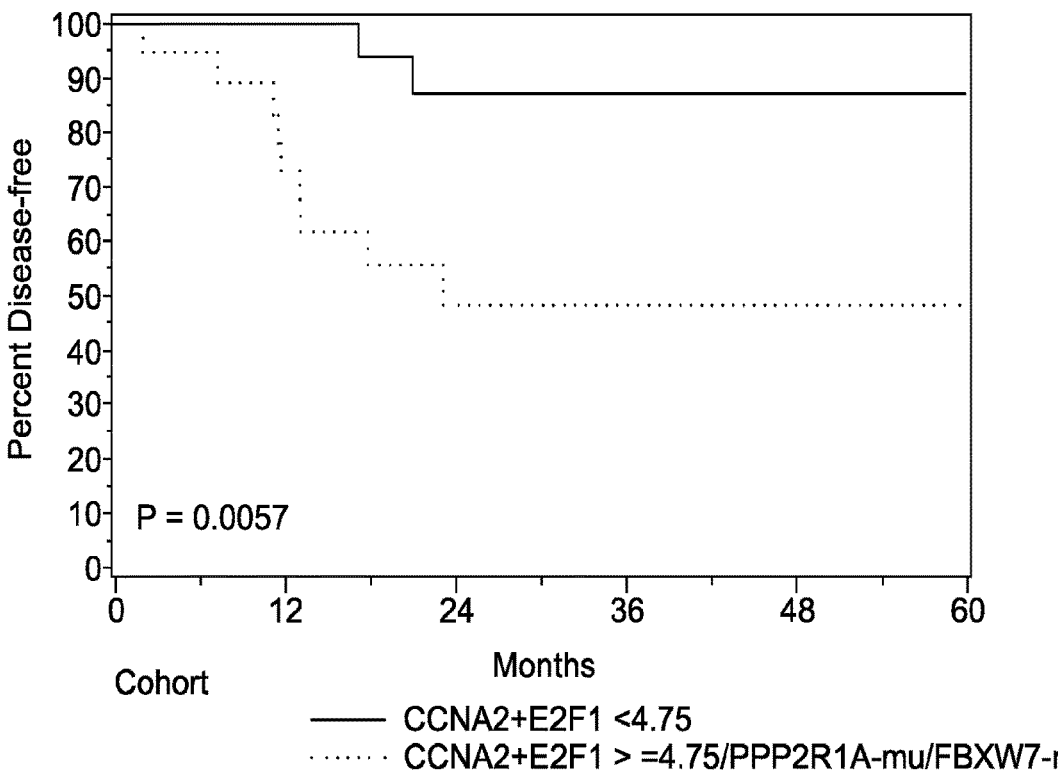
Figure 15E:
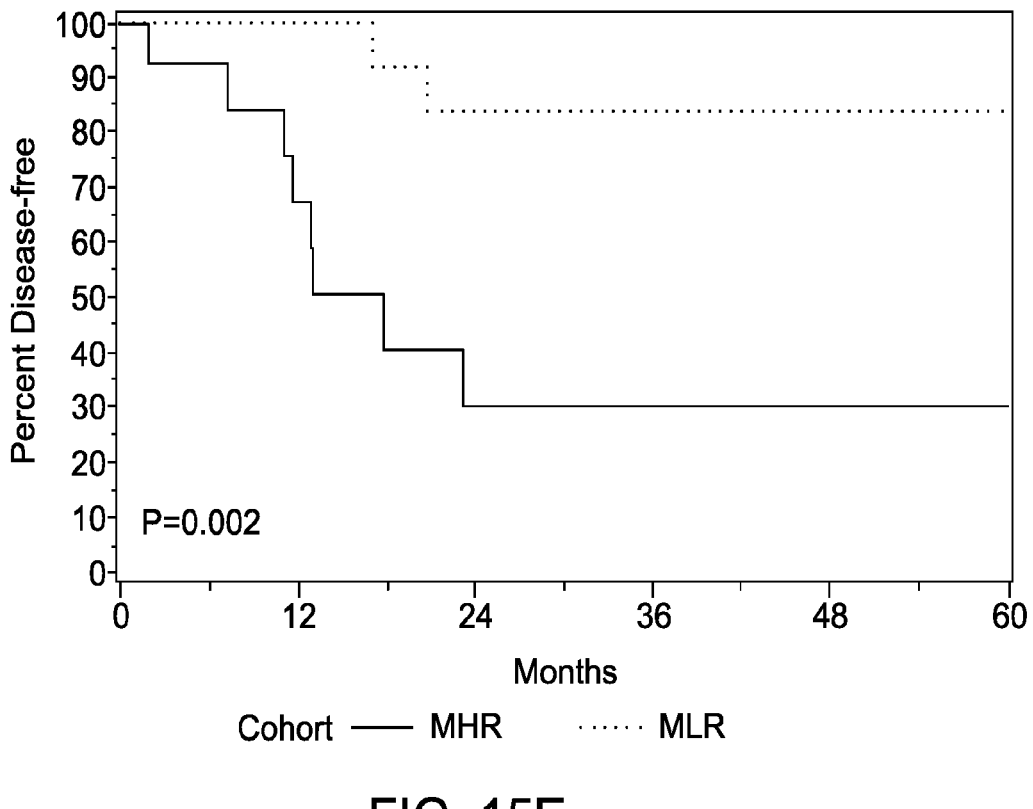

In the absence of HRmu, the marked differential in expression of cell cycle and HR genes among EEC (Table 4) would portend disparate responses to contemporary adjuvant therapies. Among 40 Stages II-IV EEC, 10 (25%) failures were documented with 2/21 (9.5%) being in ECPPF MLR cases and 8/19 (42.1%) being in MHR cases (Table 5). Collectively, stages III/IV and stages I/II G2>75% MI and G3>50% MI invariably receive adjuvant PbCT or RT or both. PFS in this broad at-risk cohort and in stages III/IV alone demonstrated significant divergence (p=0.0057 and p=0.002, respectively) in responses to contemporary therapy as a function of ECPPF MLR and MHR (FIGS. 15D and 15E). These results suggest ECPPF MLR EEC are responsive to contemporary therapy while ECPPF MRH are likely insensitive.

Figure 16A:
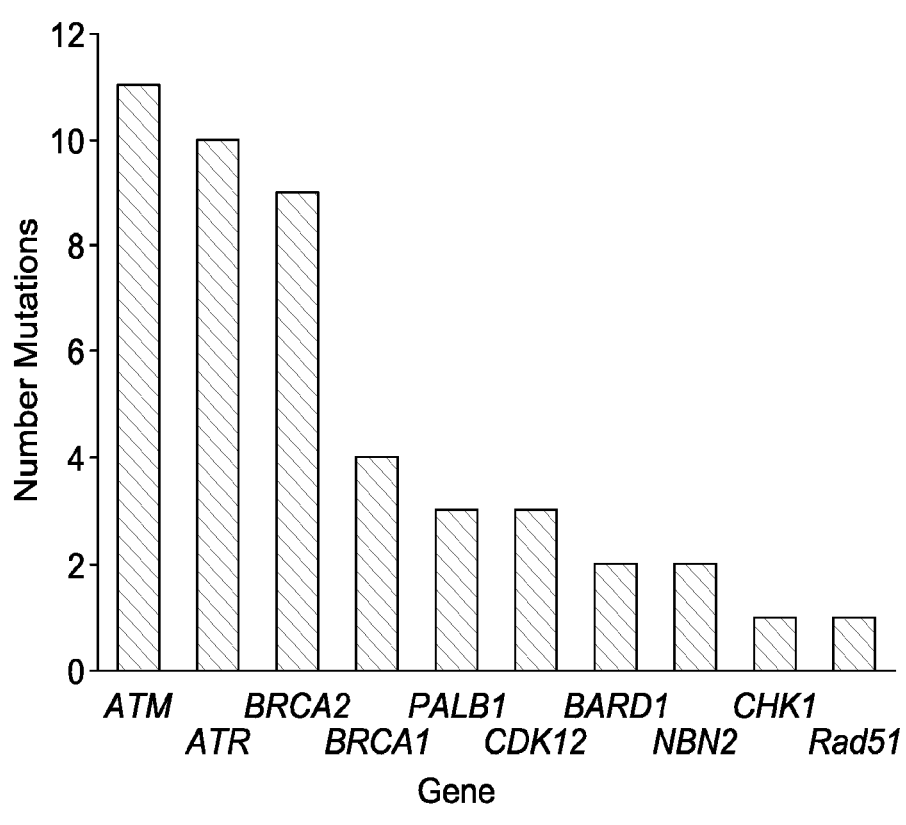
FIGS. 16A-16D. Homologous recombination mutations (HRmu) and ECPPF integration.
Figure 16B:
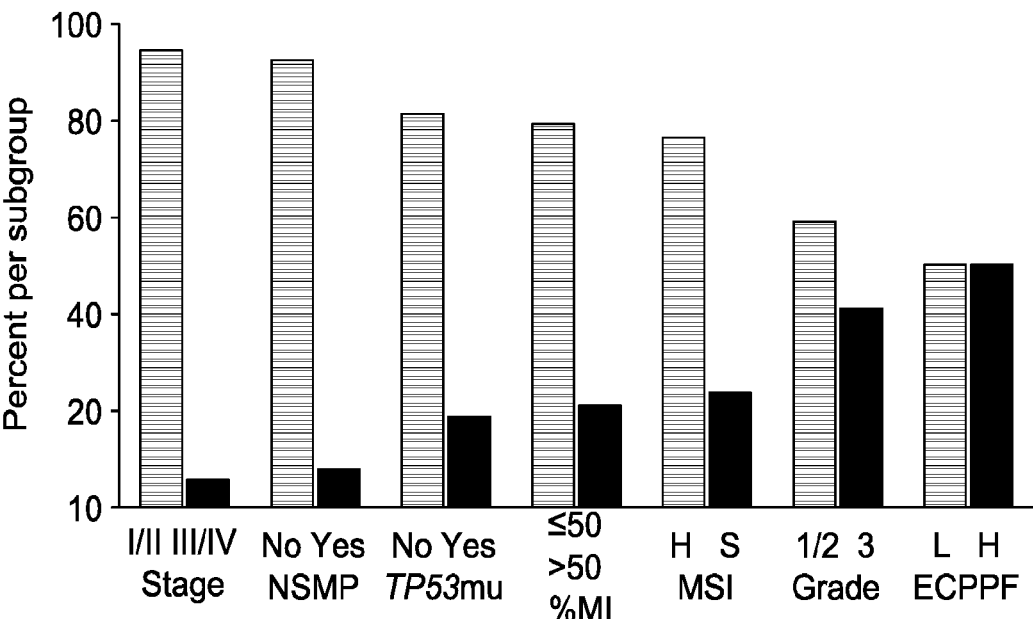
Figure 16C:
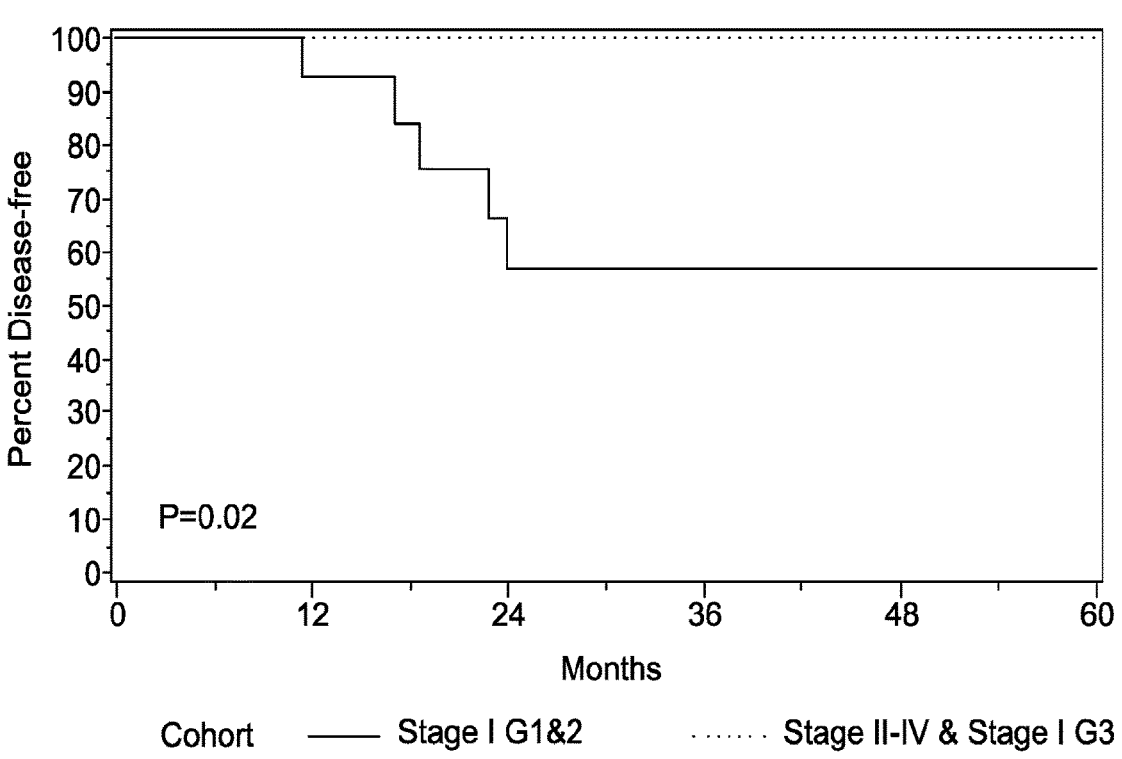
Figure 16D:
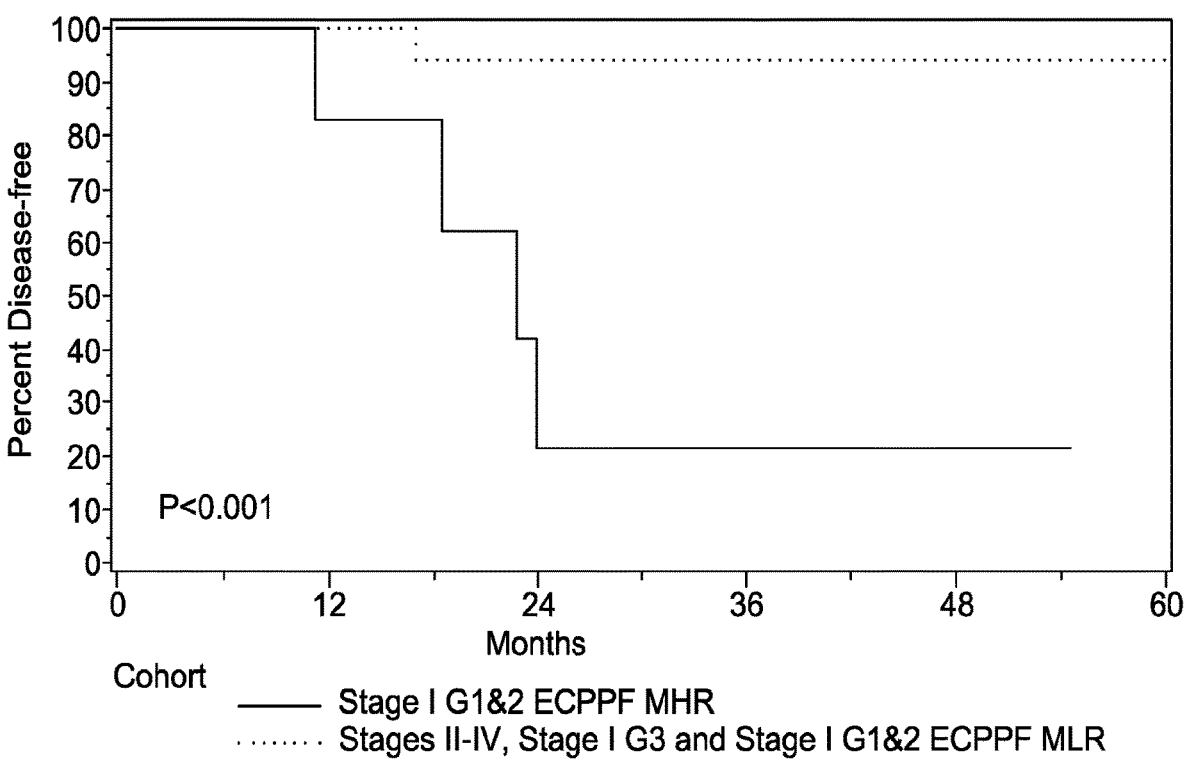

HRmu were detected in 34/164 (20.7%) cases and 7/34 (20.6%) harbored more than one HRmu. AT Rmu, ATMmu, and BRCA2mu were the most prevalent (FIG. 16A). 94% occurred in stage I/II and 76% in MSI-H cases (FIG. 16B). No failures were documented in 18 HRmu at-risk cases (stages I, G3 (13), II (3), III (1) and IV (1)) frequently subjected to contemporary adjuvant treatment including 12 (66%) ECPPF MHR cases (FIG. 16C). By contrast, recurrences were documented in 5 of 16 (31%) likely untreated HRmu stage I, G 1/2 cases. 4/5 were inner third myometrium but 4/5 were ECPPF MHR. A single recurrence was documented among 28 (3.6%) HRmu at-risk likely treated and ECPPF MLR likely untreated cases compared to 4 recurrences in 6 (66%) ECPPF MHR likely untreated cases (p<0.001) (FIG. 16D). Collectively, these results suggest HRmu including ECPPF MHR cases and ECPPF MLR cases are sensitive to contemporary therapies and present a requisite to identify ECPPF MHR/HRmu early stage, low grade cases for definitive treatment. By contrast, ECPPF MHR/HRwt would predictably be insensitive to contemporary therapeutics.

These results demonstrate that ECPPF molecular profiling can be used to identify endometrial cancers likely to respond to a particular cancer treatment (e.g., a platinum based cancer therapy).

Example 4: Exemplary Embodiments

Embodiment 1. A method for assessing a mammal having endometrial cancer, wherein said method comprises:
   (a) detecting (a-i) a presence or absence of a mutation in nucleic acid encoding a F-box/WD repeat-containing protein 7 (FBW7) polypeptide or nucleic acid regulating expression of said FBW7 polypeptide, (a-ii) a presence or absence of a mutation in nucleic acid encoding a protein phosphatase 2A subunit (PPP2R1A) polypeptide or nucleic acid regulating expression of said PPP2R1A polypeptide, and (a-iii) a presence or absence of an increased level of expression of nucleic acid encoding a cyclin-A2 (CCNA2) polypeptide in a sample from said mammal;
   (b) classifying said mammal as not being likely to respond to a platinum based cancer therapy if (b-i) said presence of said mutation of said (a-i) is detected, (b-ii) said presence of said mutation of said (a-ii) is detected, and (b-iii) said presence of said increased level is detected; and
   (c) classifying said mammal as being likely to respond to said platinum based cancer therapy if (c-i) said absence of said mutation of said (a-i) is detected, (c-ii) said absence of said mutation of said (a-ii) is detected, and (c-iii) said absence of said increased level of said expression of said nucleic acid encoding said CCNA2 polypeptide is detected.

Embodiment 2. The method of embodiment 1, wherein said mammal is a human.

Embodiment 3. The method of any one of embodiments 1-2, wherein said sample comprises cancer cells of said endometrial cancer.

Embodiment 4. The method of any one of embodiments 1-3, wherein said method further comprises detecting (a-iv) a presence or absence of a mutation in nucleic acid encoding a DNA polymerase epsilon catalytic subunit A (POLE) polypeptide or nucleic acid regulating expression of said POLE polypeptide, and (a-v) a presence or absence of a mutation in nucleic acid encoding a p53 polypeptide or nucleic acid regulating expression of said p53 polypeptide.

Embodiment 5. The method of embodiment 4, wherein said method comprises detecting (i) said presence of said mutation of said (a-i), (ii) said presence of said mutation of said (a-ii), (iii) said presence of said increased level of expression of said nucleic acid encoding said CCNA2 polypeptide, (iv) said presence of said mutation of said (a-iv), and (v) said presence of said mutation of said (a-v).

Embodiment 6. The method of embodiment 5, wherein said method comprises classifying said mammal as not being likely to respond to said platinum based cancer therapy.

Embodiment 7. The method of embodiment 4, wherein said method comprises detecting (i) said absence of said mutation of said (a-i), (ii) said absence of said mutation of said (a-ii), (iii) said absence of said increased level of expression of said nucleic acid encoding said CCNA2 polypeptide, (iv) said absence of said mutation of said (a-iv), and (v) said absence of said mutation of said (a-v).

Embodiment 8. The method of embodiment 7, wherein said method comprises classifying said mammal as being likely to respond to said platinum based cancer therapy.

Embodiment 9. The method of any one of embodiments 1-3, wherein said method further comprises detecting (a-iv) a presence or absence of a mutation in nucleic acid encoding a POLE polypeptide or nucleic acid regulating expression of said POLE polypeptide, and (a-v) a presence or absence of an increased level of expression of nucleic acid encoding a transcription factor E2F1 (E2F1) polypeptide in a sample from said mammal.

Embodiment 10. The method of embodiment 9, wherein said method comprises detecting (i) said presence of said mutation of said (a-i), (ii) said presence of said mutation of said (a-ii), (iii) said presence of said increased level of expression of said nucleic acid encoding said CCNA2 polypeptide, (iv) said presence of said mutation of said (a-iv), and (v) said presence of said increased level of expression of said nucleic acid encoding said E2F1 polypeptide.

Embodiment 11. The method of embodiment 10, wherein said method comprises classifying said mammal as not being likely to respond to said platinum based cancer therapy.

Embodiment 12. The method of embodiment 9, wherein said method comprises detecting (i) said absence of said mutation of said (a-i), (ii) said absence of said mutation of said (a-ii), (iii) said absence of said increased level of expression of said nucleic acid encoding said CCNA2 polypeptide, (iv) said absence of said mutation of said (a-iv), and (v) said absence of said increased level of expression of said nucleic acid encoding said E2F1 polypeptide.

Embodiment 13. The method of embodiment 12, wherein said method comprises classifying said mammal as being likely to respond to said platinum based cancer therapy.

Embodiment 14. A method for assessing a mammal having endometrial cancer, wherein said method comprises:

(a) detecting (a-i) a presence or absence of a mutation in nucleic acid encoding a FBW7 polypeptide or nucleic acid regulating expression of said FBW7 polypeptide, (a-ii) a presence or absence of a mutation in nucleic acid encoding a PPP2R1A polypeptide or nucleic acid regulating expression of said PPP2R1A polypeptide, and (a-iii) a presence or absence of an increased level of expression of nucleic acid encoding a cancerous inhibitor of protein phosphatase 2A (CIP2A) polypeptide in a sample from said mammal;

(b) classifying said mammal as not being likely to respond to a platinum based cancer therapy if (b-i) said presence of said mutation of said (a-i) is detected, (b-ii) said presence of said mutation of said (a-ii) is detected, and (b-iii) said presence of said increased level of expression of said nucleic acid encoding said CIP2A polypeptide is detected; and (c) classifying said mammal as being likely to respond to said platinum based cancer therapy if (c-i) said absence of said mutation of said (a-i) is detected, (c-ii) said absence of said mutation of said (a-ii) is detected, and (c-iii) said absence of said increased level of expression of said nucleic acid encoding said CIP2A polypeptide is detected.

Embodiment 15. The method of embodiment 14, wherein said mammal is a human.

Embodiment 16. The method of any one of embodiments 14-15, wherein said sample comprises cancer cells of said endometrial cancer.

Embodiment 17. The method of any one of embodiments 14-16, wherein said method further comprises detecting (a-iv) a presence or absence of a mutation in nucleic acid encoding a POLE polypeptide or nucleic acid regulating expression of said POLE polypeptide, and (a-v) a presence or absence of a mutation in nucleic acid encoding a p53 polypeptide or nucleic acid regulating expression of said p53 polypeptide.

Embodiment 18. The method of embodiment 17, wherein said method comprises detecting (i) said presence of said mutation of said (a-i), (ii) said presence of said mutation of said (a-ii), (iii) said presence of said increased level of expression of said to nucleic acid encoding said CIP2A polypeptide, (iv) said presence of said mutation of said (a-iv), and (v) said presence of said mutation of said (a-v).

Embodiment 19. The method of embodiment 18, wherein said method comprises classifying said mammal as not being likely to respond to said platinum based cancer therapy.

Embodiment 20. The method of embodiment 17, wherein said method comprises detecting (i) said absence of said mutation of said (a-i), (ii) said absence of said mutation of said (a-ii), (iii) said absence of said increased level of expression of said nucleic acid encoding said CIP2A polypeptide, (iv) said absence of said mutation of said (a-iv), and (v) said absence of said mutation of said (a-v).

Embodiment 21. The method of embodiment 20, wherein said method comprises classifying said mammal as being likely to respond to said platinum based cancer therapy.

Embodiment 22. A method for treating a mammal having endometrial cancer, wherein said method comprises:

(a) detecting (a-i) a mutation in nucleic acid encoding a FBW7 polypeptide or nucleic acid regulating expression of said FBW7 polypeptide, (a-ii) a mutation in nucleic acid encoding a PPP2R1A polypeptide or nucleic acid regulating expression of said PPP2R1A polypeptide, and (a-iii) an increased level of expression of nucleic acid encoding a CCNA2 polypeptide in a sample obtained from said mammal; and (b) administering a cancer treatment to said mammal, wherein said cancer treatment is not a platinum based cancer therapy.

Embodiment 23. The method of embodiment 22, wherein said method further comprises detecting (a-iv) a mutation in nucleic acid encoding a POLE polypeptide or nucleic acid regulating expression of said POLE polypeptide, and (a-v) a mutation in nucleic acid encoding a p53 polypeptide or nucleic acid regulating expression of said p53 polypeptide.

Embodiment 24. The method of embodiment 22, wherein said method further comprises detecting (a-iv) a mutation in nucleic acid encoding a POLE polypeptide or nucleic acid regulating expression of said POLE polypeptide, and (a-v) an increased level of expression of nucleic acid encoding a E2F1 polypeptide in a sample from said mammal.

Embodiment 25. A method for treating cancer, wherein said method comprises administering a cancer treatment to a mammal identified as having (i) a mutation in nucleic acid encoding a FBW7 polypeptide or nucleic acid regulating expression of said FBW7 polypeptide, (ii) a mutation in nucleic acid encoding a PPP2R1A polypeptide or nucleic acid regulating expression of said PPP2R1A polypeptide, and (iii) an increased level of expression of nucleic acid encoding a CCNA2 polypeptide in a sample obtained from said mammal, wherein said cancer treatment is not a platinum based cancer therapy.

Embodiment 26a. The method of embodiment 25, wherein said mammal is a mammal identified as having (iv) a mutation in nucleic acid encoding a POLE polypeptide or nucleic acid regulating expression of said POLE polypeptide, and (v) a mutation in nucleic acid encoding a p53 polypeptide or nucleic acid regulating expression of said p53 polypeptide.

Embodiment 26b. The method of embodiment 25, wherein said mammal is a mammal identified as having (iv) a mutation in nucleic acid encoding a POLE polypeptide or nucleic acid regulating expression of said POLE polypeptide, and (v) an increased level of expression of nucleic acid encoding a E2F1 polypeptide in a sample from said mammal.

Embodiment 27. The method of any one of embodiments 22-26, wherein said mammal is a human.

Embodiment 28. The method of any one of embodiments 22-27, wherein said sample comprises cancer cells of said endometrial cancer.

Embodiment 29. The method of any one of embodiments 22-28, wherein said cancer treatment comprises surgery.

Embodiment 30. The method of any one of embodiments 22-28, wherein said cancer treatment comprises radiation treatment.

Embodiment 31. A method for treating a mammal having endometrial cancer, wherein said method comprises:

(a) detecting (a-i) an absence of a mutation in nucleic acid encoding a FBW7 polypeptide or nucleic acid regulating expression of said FBW7 polypeptide, (a-ii) an absence of a mutation in nucleic acid encoding a PPP2R1A polypeptide or nucleic acid regulating expression of said PPP2R1A polypeptide, and (a-iii) an absence of an increased level of expression of nucleic acid encoding a CCNA2 polypeptide in a sample obtained from said mammal; and (b) administering a platinum based cancer therapy to said mammal.

Embodiment 32. The method of embodiment 31, wherein said method further comprises detecting (a-iv) an absence of a mutation in nucleic acid encoding a POLE polypeptide or nucleic acid regulating expression of said POLE polypeptide, and (a-v) an absence of a mutation in nucleic acid encoding a p53 polypeptide or nucleic acid regulating expression of said p53 polypeptide.

Embodiment 33. The method of embodiment 31, wherein said method further comprises detecting (a-iv) an absence of a mutation in nucleic acid encoding a POLE polypeptide or nucleic acid regulating expression of said POLE polypeptide, and (a-v) an absence of an increased level of expression of nucleic acid encoding a E2F1 polypeptide in a sample from said mammal.

Embodiment 34. A method for treating endometrial cancer, wherein said method comprises administering a platinum based cancer therapy to a mammal identified as lacking (i) a mutation in nucleic acid encoding a FBW7 polypeptide or nucleic acid regulating expression of said FBW7 polypeptide, (ii) a mutation in nucleic acid encoding a PPP2R1A polypeptide or nucleic acid regulating expression of said PPP2R1A polypeptide, and (iii) an increased level of expression of nucleic acid encoding a CCNA2 polypeptide in a sample obtained from said mammal.

Embodiment 35. The method of embodiment 34, wherein said mammal is a mammal identified as lacking (iv) a mutation in nucleic acid encoding a POLE polypeptide or nucleic acid regulating expression of said POLE polypeptide, and (v) a mutation in nucleic acid encoding a p53 polypeptide or nucleic acid regulating expression of said p53 polypeptide.

Embodiment 36. The method of embodiment 34, wherein said mammal is a mammal identified as lacking (iv) a mutation in nucleic acid encoding a POLE polypeptide or nucleic acid regulating expression of said POLE polypeptide, and (v) an increased level of expression of nucleic acid encoding a E2F1 polypeptide in a sample from said mammal.

Embodiment 37. The method of any one of embodiments 31-36, wherein said mammal is a human.

Embodiment 38. The method of any one of embodiments 31-37, wherein said sample comprises cancer cells of said endometrial cancer.

Embodiment 39. The method of any one of embodiments 31-38, wherein said platinum based cancer therapy is selected from the group consisting of cisplatin, carboplatin, oxaliplatin, nedaplatin, triplatin tetranitrate, phenanthriplatin, picoplatin, and satraplatin.

Embodiment 40. A method for treating a mammal having endometrial cancer, wherein said method comprises:

(a) detecting (a-i) a mutation in nucleic acid encoding a FBW7 polypeptide or nucleic acid regulating expression of said FBW7 polypeptide, (a-ii) a mutation in nucleic acid encoding a PPP2R1A polypeptide or nucleic acid regulating expression of said PPP2R1A polypeptide, and (a-iii) an increased level of expression of nucleic acid encoding a CIP2A polypeptide in a sample obtained from said mammal; and (b) administering a cancer treatment to said mammal, wherein said cancer treatment is not a platinum based cancer therapy.

Embodiment 41. The method of embodiment 40, wherein said method further comprises detecting (a-iv) a mutation in nucleic acid encoding a POLE polypeptide or nucleic acid regulating expression of said POLE polypeptide, and (a-v) a mutation in nucleic acid encoding a p53 polypeptide or nucleic acid regulating expression of said p53 polypeptide.

Embodiment 42. A method for treating cancer, wherein said method comprises administering a cancer treatment to a mammal identified as having (i) a mutation in nucleic acid encoding a FBW7 polypeptide or nucleic acid regulating expression of said FBW7 polypeptide, (ii) a mutation in nucleic acid encoding a PPP2R1A polypeptide or nucleic acid regulating expression of said PPP2R1A polypeptide, and (iii) an increased level of expression of nucleic acid encoding a CIP2A polypeptide in a sample obtained from said mammal, wherein said cancer treatment is not a platinum based cancer therapy.

Embodiment 43. The method of embodiment 42, wherein said mammal is a mammal identified as having (iv) a mutation in nucleic acid encoding a POLE polypeptide or nucleic acid regulating expression of said POLE polypeptide, and (v) a mutation in nucleic acid encoding a p53 polypeptide or nucleic acid regulating expression of said p53 polypeptide.

Embodiment 44. The method of any one of embodiments 40-43, wherein said mammal is a human.

Embodiment 45. The method of any one of embodiments 40-44, wherein said sample comprises cancer cells of said endometrial cancer.

Embodiment 46. The method of any one of embodiments 40-45, wherein said cancer treatment comprises surgery.

Embodiment 47. The method of any one of embodiments 40-46, wherein said cancer treatment comprises radiation treatment.

Embodiment 48. A method for treating a mammal having endometrial cancer, wherein said method comprises:
(a) detecting (a-i) an absence of a mutation in nucleic acid encoding a FBW7 polypeptide or nucleic acid regulating expression on of said FBW7 polypeptide, (a-ii) an absence of a mutation in nucleic acid encoding a PPP2R1A polypeptide or nucleic acid regulating expression of said PPP2R1A polypeptide, and (a-iii) an absence of an increased level of expression of nucleic acid encoding a CIP2A polypeptide in a sample obtained from said mammal; and
(b) administering a platinum based cancer therapy to said mammal.

Embodiment 49. The method of embodiment 48, wherein said method further comprises detecting (a-iv) an absence of a mutation in nucleic acid encoding a POLE polypeptide or nucleic acid regulating expression of said POLE polypeptide, and (a-v) an absence of a mutation in nucleic acid encoding a p53 polypeptide or nucleic acid regulating expression of said p53 polypeptide.

Embodiment 50. A method for treating endometrial cancer, wherein said method comprises administering a platinum based cancer therapy to a mammal identified as lacking (i) a mutation in nucleic acid encoding a FBW7 polypeptide or nucleic acid regulating expression of said FBW7 polypeptide, (ii) a mutation in nucleic acid encoding a PPP2R1A polypeptide or nucleic acid regulating expression of said PPP2R1A polypeptide, and (iii) an increased level of expression of nucleic acid encoding a CIP2A polypeptide in a sample obtained from said mammal.

Embodiment 51. The method of embodiment 50, wherein said mammal is a mammal identified as lacking (iv) a mutation in nucleic acid encoding a POLE polypeptide or nucleic acid regulating expression of said POLE polypeptide, and (v) a mutation in nucleic acid encoding a p53 polypeptide or nucleic acid regulating expression of said p53 polypeptide.

Embodiment 52. The method of any one of embodiments 48-51, wherein said mammal is a human.

Embodiment 53. The method of any one of embodiments 48-52, wherein said sample comprises cancer cells of said endometrial cancer.

Embodiment 54. The method of any one of embodiments 48-53, wherein said platinum based cancer therapy is selected from the group consisting of cisplatin, carboplatin, oxaliplatin, nedaplatin, triplatin tetranitrate, phenanthriplatin, picoplatin, and satraplatin.

Embodiment 55. A method for treating a mammal having endometrial cancer, wherein said method comprises:
(a) detecting (a-i) a mutation in nucleic acid encoding a FBW7 polypeptide or nucleic acid regulating expression of said FBW7 polypeptide, (a-ii) a mutation in nucleic acid encoding a PPP2R1A polypeptide or nucleic acid regulating expression of said PPP2R1A polypeptide, and (a-iii) an increased level of expression of nucleic acid encoding a CCNA2 polypeptide in a sample obtained from said mammal;
(b) administering a platinum based cancer therapy to said mammal; and
(c) administering a histone deacetylase inhibitor to said mammal.

Embodiment 56. The method of embodiment 40, wherein said method further comprises detecting (a-iv) a mutation in nucleic acid encoding a POLE polypeptide or nucleic acid regulating expression of said POLE polypeptide, and (a-v) a mutation in nucleic acid encoding a p53 polypeptide or nucleic acid regulating expression of said p53 polypeptide.

Embodiment 57. The method of embodiment 40, wherein said method further comprises detecting (a-iv) a mutation in nucleic acid encoding a POLE polypeptide or nucleic acid regulating expression of said POLE polypeptide, and (a-v) an increased level of expression of nucleic acid encoding a E2F1 polypeptide in a sample from said mammal.

Embodiment 58. A method for treating endometrial cancer, wherein said method comprises administering a platinum based cancer therapy and a histone deacetylase inhibitor to a mammal identified as having (i) a mutation in nucleic acid encoding a FBW7 polypeptide or nucleic acid regulating expression of said FBW7 polypeptide, (ii) a mutation in nucleic acid encoding a PPP2R1A polypeptide or nucleic acid regulating expression of said PPP2R1A polypeptide, and (iii) an increased level of expression of nucleic acid encoding a CCNA2 polypeptide in a sample obtained from said mammal.

Embodiment 59. The method of embodiment 58, wherein said mammal is mammal identified as having (iv) a mutation in nucleic acid encoding a POLE polypeptide or nucleic acid regulating expression of said POLE polypeptide, and (v) a mutation in nucleic acid encoding a p53 polypeptide or nucleic acid regulating expression of said p53 polypeptide.

Embodiment 60. The method of embodiment 58, wherein said mammal is a mammal identified as having (iv) a mutation in nucleic acid encoding a POLE polypeptide or nucleic acid regulating expression of said POLE polypeptide, and (v) an increased level of expression of nucleic acid encoding a E2F1 polypeptide in a sample from said mammal.

Embodiment 61. The method of any one of embodiments 55-60, wherein said mammal is a human.

Embodiment 62. The method of any one of embodiments 55-61, wherein said sample comprises cancer cells of said endometrial cancer.

Embodiment 63. The method of any one of embodiments 55-62, wherein said platinum based cancer therapy is selected from the group consisting of cisplatin, carboplatin, oxaliplatin, nedaplatin, triplatin tetranitrate, phenanthriplatin, picoplatin, and satraplatin.

Embodiment 64. The method of any one of embodiments 55-63, wherein said histone deacetylase inhibitor is selected from the group consisting of panobinostat, trichostatin A, trapoxin B, phenylbutyrate, valproic acid, vorinostat, belinostat, LAQ824, entinostat, tacedinaline, and mocetinostat.

Embodiment 65. A method for treating a mammal having endometrial cancer, wherein said method comprises:
(a) detecting (a-i) a mutation in nucleic acid encoding a FBW7 polypeptide or nucleic acid regulating expression of said FBW7 polypeptide, (a-ii) a mutation in nucleic acid encoding a PPP2R1A polypeptide or nucleic acid regulating expression of said PPP2R1A polypeptide, and (a-iii) an increased level of expression of nucleic acid encoding a CIP2A polypeptide in a sample obtained from said mammal;
(b) administering a platinum based cancer therapy to said mammal; and
(c) administering a histone deacetylase inhibitor to said mammal.

Embodiment 66. The method of embodiment 65, wherein said method further comprises detecting (a-iv) a mutation in nucleic acid encoding a POLE polypeptide or nucleic acid regulating expression of said POLE polypeptide, and (a-v) a mutation in nucleic acid encoding a p53 polypeptide or nucleic acid regulating expression of said p53 polypeptide.

Embodiment 67. A method for treating endometrial cancer, wherein said method comprises administering a platinum based cancer therapy and a histone deacetylase inhibitor to a mammal identified as having (i) a mutation in nucleic acid encoding a FBW7 polypeptide or nucleic acid regulating expression of said FBW7 polypeptide, (ii) a mutation in nucleic acid encoding a PPP2R1A polypeptide or nucleic acid regulating expression of said PPP2R1A polypeptide, and (iii) an increased level of expression of nucleic acid encoding a CIP2A polypeptide in a sample obtained from said mammal.

Embodiment 68. The method of embodiment 67, wherein said mammal is a mammal identified as having (iv) a mutation in nucleic acid encoding a POLE polypeptide or nucleic acid regulating expression of said POLE polypeptide, and (v) a mutation in nucleic acid encoding a p53 polypeptide or nucleic acid regulating expression of said p53 polypeptide.

Embodiment 69. The method of any one of embodiments 65-68, wherein said mammal is a human.

Embodiment 70. The method of any one of embodiments 65-69, wherein said sample comprises cancer cells of said endometrial cancer.

Embodiment 71. The method of any one of embodiments 65-70, wherein said platinum based cancer therapy is selected from the group consisting of cisplatin, carboplatin, oxaliplatin, nedaplatin, triplatin tetranitrate, phenanthriplatin, picoplatin, and satraplatin.

Embodiment 72. The method of any one of embodiments 65-71, wherein said histone deacetylase inhibitor is selected from the group consisting of panobinostat, trichostatin A, trapoxin B, phenylbutyrate, valproic acid, vorinostat, belinostat, LAQ824, entinostat, tacedinaline, and mocetinostat.

Embodiment 73. A method for treating a mammal having endometrial cancer, wherein said method comprises:
(a) detecting (a-i) a mutation in nucleic acid encoding a FBW7 polypeptide or nucleic acid regulating expression of said FBW7 polypeptide, (a-ii) a mutation in nucleic acid encoding a PPP2R1A polypeptide or nucleic acid regulating expression of said PPP2R1A polypeptide, and (a-iii) an increased level of expression of nucleic acid encoding a CCNA2 polypeptide in a sample obtained from the mammal;
(b) administering a platinum based cancer therapy to said mammal; and
(c) administering an AKT inhibitor to said mammal.

Embodiment 74. The method of embodiment 73, wherein said method further comprises detecting (a-iv) a mutation in nucleic acid encoding a POLE polypeptide or nucleic acid regulating expression of said POLE polypeptide, and (a-v) a mutation in nucleic acid encoding a p53 polypeptide or nucleic acid regulating expression of said p53 polypeptide.

Embodiment 75. The method of embodiment 73, wherein said method further comprises detecting (a-iv) a mutation in nucleic acid encoding a POLE polypeptide or nucleic acid regulating expression of said POLE polypeptide, and (a-v) an increased level of expression of nucleic acid encoding a E2F1 polypeptide in a sample from said mammal.

Embodiment 76. A method for treating endometrial cancer, wherein said method comprises administering a platinum based cancer therapy and an AKT inhibitor to a mammal identified as having (i) a mutation in nucleic acid encoding a FBW7 polypeptide or nucleic acid regulating expression of said FBW7 polypeptide, (ii) a mutation in nucleic acid encoding a PPP2R1A polypeptide or nucleic acid regulating expression of said PPP2R1A polypeptide, and (iii) an increased level of expression of nucleic acid encoding a CCNA2 polypeptide in a sample obtained from said mammal.

Embodiment 77. The method of embodiment 76, wherein said mammal is a mammal identified as having (iv) a mutation in nucleic acid encoding a POLE polypeptide or nucleic acid regulating expression of said POLE polypeptide, and (v) a mutation in nucleic acid encoding a p53 polypeptide or nucleic acid regulating expression of said p53 polypeptide.

Embodiment 78. The method of embodiment 76, wherein said mammal is a mammal identified as having (iv) a mutation in nucleic acid encoding a POLE polypeptide or nucleic acid regulating expression of said POLE polypeptide, and (v) an increased level of expression of nucleic acid encoding a E2F1 polypeptide in a sample from said mammal.

Embodiment 79. The method of any one of embodiments 73-76, wherein said mammal is a human.

Embodiment 80. The method of any one of embodiments 73-77, wherein said sample comprises cancer cells of said endometrial cancer.

Embodiment 81. The method of any one of embodiments 73-80, wherein said platinum based cancer therapy is selected from the group consisting of cisplatin, carboplatin, oxaliplatin, nedaplatin, triplatin tetranitrate, phenanthriplatin, picoplatin, and satraplatin.

Embodiment 82. The method of any one of embodiments 73-81, wherein said AKT inhibitor is selected from the group consisting of GSK2141795, GSK2110183, GSK 690693, VQD-002, perifosine, miltefosine, MK-2206, AZD5363, ipatasertib, and triciribine.

Embodiment 83. A method for treating a mammal having endometrial cancer, wherein said method comprises:

(a) detecting (a-i) a mutation in nucleic acid encoding a FBW7 polypeptide or nucleic acid regulating expression of said FBW7 polypeptide, (a-ii) a mutation in nucleic acid encoding a PPP2R1A polypeptide or nucleic acid regulating expression of said PPP2R1A polypeptide, and (a-iii) an increased level of expression of nucleic acid encoding a CIP2A polypeptide in a sample obtained from the mammal;

(b) administering a platinum based cancer therapy to said mammal; and (c) administering an AKT inhibitor to said mammal.

Embodiment 84. The method of embodiment 83, wherein said method further comprises detecting (a-iv) a mutation in nucleic acid encoding a POLE polypeptide or nucleic acid regulating expression of said POLE polypeptide, and (a-v) a mutation in nucleic acid encoding a p53 polypeptide or nucleic acid regulating expression of said p53 polypeptide.

Embodiment 85. A method for treating endometrial cancer, wherein said method comprises administering a platinum based cancer therapy and an AKT inhibitor to a mammal identified as having (i) a mutation in nucleic acid encoding a FBW7 polypeptide or nucleic acid regulating expression of said FBW7 polypeptide, (ii) a mutation in nucleic acid encoding a PPP2R1A polypeptide or nucleic acid regulating expression of said PPP2R1A polypeptide, and (iii) an increased level of expression of nucleic acid encoding a CIP2A polypeptide in a sample obtained from said mammal.

Embodiment 86. The method of embodiment 85, wherein said mammal is a mammal identified as having (iv) a mutation in nucleic acid encoding a POLE polypeptide or nucleic acid regulating expression of said POLE polypeptide, and (v) a mutation in nucleic acid encoding a p53 polypeptide or nucleic acid regulating expression of said p53 polypeptide.

Embodiment 87. The method of any one of embodiments 83-86, wherein said mammal is a human.

Embodiment 88. The method of any one of embodiments 83-87, wherein said sample comprises cancer cells of said endometrial cancer.

Embodiment 89. The method of any one of embodiments 83-88, wherein said platinum based cancer therapy is selected from the group consisting of cisplatin, carboplatin, oxaliplatin, nedaplatin, triplatin tetranitrate, phenanthriplatin, picoplatin, and satraplatin.

Embodiment 90. The method of any one of embodiments 83-89, wherein said AKT inhibitor is selected from the group consisting of GSK2141795, GSK2110183, GSK 690693, VQD-002, perifosine, miltefosine, MK-2206, AZD5363, ipatasertib, and triciribine.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having endometrial cancer, wherein said method comprises:
   (a) detecting (a-i) a mutation in nucleic acid encoding a FBW7 polypeptide or nucleic acid regulating expression of said FBW7 polypeptide, (a-ii) a mutation in nucleic acid encoding a PPP2R1A polypeptide or nucleic acid regulating expression of said PPP2R1A polypeptide, and (a-iii) an increased level of expression of nucleic acid encoding a CCNA2 polypeptide in a sample obtained from said mammal as compared to the level of expression of nucleic acid encoding said CCNA2 polypeptide in a control sample obtained from a comparable mammal not having endometrial cancer; and
   (b) administering a cancer treatment to said mammal, wherein said cancer treatment is not a platinum based cancer therapy.

2. The method of claim 1, wherein said method further comprises detecting (a-iv) a mutation in nucleic acid encoding a POLE polypeptide or nucleic acid regulating expression of said POLE polypeptide, and (a-v) a mutation in nucleic acid encoding a p53 polypeptide or nucleic acid regulating expression of said p53 polypeptide.

3. The method of claim 1, wherein said method further comprises detecting (a-iv) a mutation in nucleic acid encoding a POLE polypeptide or nucleic acid regulating expression of said POLE polypeptide, and (a-v) an increased level of expression of nucleic acid encoding a E2F1 polypeptide in a sample from said mammal as compared to the level of expression of nucleic acid encoding said E2F1 polypeptide in a control sample obtained from a comparable mammal not having endometrial cancer.

4. The method of claim 1, wherein said mammal is a human.

5. The method of claim 1, wherein said sample comprises cancer cells of said endometrial cancer.

6. The method of claim 1, wherein said cancer treatment comprises surgery or radiation treatment.

7. A method for treating a mammal having endometrial cancer, wherein said method comprises:
   (a) detecting (a-i) an absence of a mutation in nucleic acid encoding a FBW7 polypeptide or nucleic acid regulating expression of said FBW7 polypeptide, (a-ii) an absence of a mutation in nucleic acid encoding a PPP2R1A polypeptide or nucleic acid regulating expression of said PPP2R1A polypeptide, and (a-iii) an absence of an increased level of expression of nucleic acid encoding a CCNA2 polypeptide in a sample obtained from said mammal as compared to the level of expression of nucleic acid encoding said CCNA2 polypeptide in a control sample obtained from a comparable mammal not having endometrial cancer; and
   (b) administering a platinum based cancer therapy to said mammal.

8. The method of claim 7, wherein said method further comprises detecting (a-iv) an absence of a mutation in nucleic acid encoding a POLE polypeptide or nucleic acid regulating expression of said POLE polypeptide, and (a-v) an absence of a mutation in nucleic acid encoding a p53 polypeptide or nucleic acid regulating expression of said p53 polypeptide.

9. The method of claim 7, wherein said method further comprises detecting (a-iv) an absence of a mutation in nucleic acid encoding a POLE polypeptide or nucleic acid regulating expression of said POLE polypeptide, and (a-v) an absence of an increased level of expression of nucleic acid encoding a E2F1 polypeptide in a sample from said mammal as compared to the level of expression of nucleic acid encoding said E2F1 polypeptide in a control sample obtained from a comparable mammal not having endometrial cancer.

10. The method of claim 7, wherein said mammal is a human.

11. The method of claim 7, wherein said sample comprises cancer cells of said endometrial cancer.

12. The method of claim 7, wherein said platinum based cancer therapy is selected from the group consisting of cisplatin, carboplatin, oxaliplatin, nedaplatin, triplatin tetranitrate, phenanthriplatin, picoplatin, and satraplatin.

13. A method for treating a mammal having endometrial cancer, wherein said method comprises:

(a) detecting (a-i) a mutation in nucleic acid encoding a FBW7 polypeptide or nucleic acid regulating expression of said FBW7 polypeptide, (a-ii) a mutation in nucleic acid encoding a PPP2R1A polypeptide or nucleic acid regulating expression of said PPP2R1A polypeptide, and (a-iii) an increased level of expression of nucleic acid encoding a CIP2A polypeptide in a sample obtained from said mammal as compared to the level of expression of nucleic acid encoding said CIP2A polypeptide in a control sample obtained from a comparable mammal not having endometrial cancer; and (b) administering a cancer treatment to said mammal, wherein said cancer treatment is not a platinum based cancer therapy.

14. The method of claim 13, wherein said method further comprises detecting (a-iv) a mutation in nucleic acid encoding a POLE polypeptide or nucleic acid regulating expression of said POLE polypeptide, and (a-v) a mutation in nucleic acid encoding a p53 polypeptide or nucleic acid regulating expression of said p53 polypeptide.

15. The method of claim 13, wherein said mammal is a human.

16. The method of claim 13, wherein said sample comprises cancer cells of said endometrial cancer.

17. The method of claim 13, wherein said cancer treatment comprises surgery or radiation treatment.

18. A method for treating a mammal having endometrial cancer, wherein said method comprises:

(a) detecting (a-i) an absence of a mutation in nucleic acid encoding a FBW7 polypeptide or nucleic acid regulating expression on of said FBW7 polypeptide, (a-ii) an absence of a mutation in nucleic acid encoding a PPP2R1A polypeptide or nucleic acid regulating expression of said PPP2R1A polypeptide, and (a-iii) an absence of an increased level of expression of nucleic acid encoding a CIP2A polypeptide in a sample obtained from said mammal as compared to the level of expression of nucleic acid encoding said CIP2A polypeptide in a control sample obtained from a comparable mammal not having endometrial cancer; and (b) administering a platinum based cancer therapy to said mammal.

19. The method of claim 18, wherein said method further comprises detecting (a-iv) an absence of a mutation in nucleic acid encoding a POLE polypeptide or nucleic acid regulating expression of said POLE polypeptide, and (a-v) an absence of a mutation in nucleic acid encoding a p53 polypeptide or nucleic acid regulating expression of said p53 polypeptide.

20. The method of claim 18, wherein said mammal is a human.

21. The method of claim 18, wherein said sample comprises cancer cells of said endometrial cancer.

22. The method of claim 18, wherein said platinum based cancer therapy is selected from the group consisting of cisplatin, carboplatin, oxaliplatin, nedaplatin, triplatin tetranitrate, phenanthriplatin, picoplatin, and satraplatin.

\* \* \* \* \*

```
                         SEQUENCE LISTING

<160> NUMBER OF SEQ ID NOS: 18

<210> SEQ ID NO 1
<211> LENGTH: 21
<212> TYPE: DNA
<213> ORGANISM: artificial
<220> FEATURE:
<223> OTHER INFORMATION: synthetic primer

<400> SEQUENCE: 1
tgtcactgtc ttgtaccctt g                                              21

<210> SEQ ID NO 2
<211> LENGTH: 19
<212> TYPE: DNA
<213> ORGANISM: artificial
<220> FEATURE:
<223> OTHER INFORMATION: synthetic primer

<400> SEQUENCE: 2
ggcgtttgga gtggtagaa                                                 19

<210> SEQ ID NO 3
<211> LENGTH: 21
```

```
<212> TYPE: DNA
<213> ORGANISM: artificial
<220> FEATURE:
<223> OTHER INFORMATION: synthetic primer

<400> SEQUENCE: 3
gccatctaca agcagtcaca g                                          21

<210> SEQ ID NO 4
<211> LENGTH: 21
<212> TYPE: DNA
<213> ORGANISM: artificial
<220> FEATURE:
<223> OTHER INFORMATION: synthetic primer

<400> SEQUENCE: 4
tcatccaaat actccacacg c                                          21

<210> SEQ ID NO 5
<211> LENGTH: 21
<212> TYPE: DNA
<213> ORGANISM: artificial
<220> FEATURE:
<223> OTHER INFORMATION: synthetic primer

<400> SEQUENCE: 5
ctgcatttgg ctgtgaacta c                                          21

<210> SEQ ID NO 6
<211> LENGTH: 21
<212> TYPE: DNA
<213> ORGANISM: artificial
<220> FEATURE:
<223> OTHER INFORMATION: synthetic primer

<400> SEQUENCE: 6
acaaactctg ctacttctgg g                                          21

<210> SEQ ID NO 7
<211> LENGTH: 20
<212> TYPE: DNA
<213> ORGANISM: artificial
<220> FEATURE:
<223> OTHER INFORMATION: synthetic primer

<400> SEQUENCE: 7
tcttgagcaa caccctcttc                                            20

<210> SEQ ID NO 8
<211> LENGTH: 21
<212> TYPE: DNA
<213> ORGANISM: artificial
<220> FEATURE:
<223> OTHER INFORMATION: synthetic primer

<400> SEQUENCE: 8
ttcttgtgtc gccatatacc g                                          21

<210> SEQ ID NO 9
<211> LENGTH: 19
<212> TYPE: DNA
<213> ORGANISM: artificial
<220> FEATURE:
<223> OTHER INFORMATION: synthetic primer

<400> SEQUENCE: 9
```

-continued

```
tctccgagga cactgacag                                             19

<210> SEQ ID NO 10
<211> LENGTH: 22
<212> TYPE: DNA
<213> ORGANISM: artificial
<220> FEATURE:
<223> OTHER INFORMATION: synthetic primer

<400> SEQUENCE: 10
atcaccataa ccatctgctc tg                                         22

<210> SEQ ID NO 11
<211> LENGTH: 21
<212> TYPE: DNA
<213> ORGANISM: artificial
<220> FEATURE:
<223> OTHER INFORMATION: synthetic primer

<400> SEQUENCE: 11
agtcagtaca aagccgtgaa g                                          21

<210> SEQ ID NO 12
<211> LENGTH: 22
<212> TYPE: DNA
<213> ORGANISM: artificial
<220> FEATURE:
<223> OTHER INFORMATION: synthetic primer

<400> SEQUENCE: 12
atagtcgtgt gagtttctgt cc                                         22

<210> SEQ ID NO 13
<211> LENGTH: 22
<212> TYPE: DNA
<213> ORGANISM: artificial
<220> FEATURE:
<223> OTHER INFORMATION: synthetic primer

<400> SEQUENCE: 13
gccataatta cagaggactc gg                                         22

<210> SEQ ID NO 14
<211> LENGTH: 21
<212> TYPE: DNA
<213> ORGANISM: artificial
<220> FEATURE:
<223> OTHER INFORMATION: synthetic primer

<400> SEQUENCE: 14
ttccgtgaat acatccccaa g                                          21

<210> SEQ ID NO 15
<211> LENGTH: 20
<212> TYPE: DNA
<213> ORGANISM: artificial
<220> FEATURE:
<223> OTHER INFORMATION: synthetic primer

<400> SEQUENCE: 15
accgctactt gacattggac                                            20

<210> SEQ ID NO 16
<211> LENGTH: 21
<212> TYPE: DNA
<213> ORGANISM: artificial
```

-continued

```
<220> FEATURE:
<223> OTHER INFORMATION: synthetic primer

<400> SEQUENCE: 16
gggagttcgg ttttgatggt c                                              21

<210> SEQ ID NO 17
<211> LENGTH: 19
<212> TYPE: DNA
<213> ORGANISM: artificial
<220> FEATURE:
<223> OTHER INFORMATION: synthetic primer

<400> SEQUENCE: 17
acatcgctca gacaccatg                                                 19

<210> SEQ ID NO 18
<211> LENGTH: 22
<212> TYPE: DNA
<213> ORGANISM: artificial
<220> FEATURE:
<223> OTHER INFORMATION: synthetic primer

<400> SEQUENCE: 18
tgtagttgag gtcaatgaag gg                                             22
```